United States Patent [19]

Cayley et al.

[11] Patent Number: 5,770,192
[45] Date of Patent: Jun. 23, 1998

[54] BIOLOGICAL CONTROL AGENTS

[75] Inventors: Patricia Jane Cayley, Berkhamsted; Lorna Mary Dyet Stewart, London; Robert David Possee; Miguel Lopez Ferber, both of Oxford, all of United Kingdom

[73] Assignees: Roussel-Uclaf, Paris, France; Natural Environment Research Council, Swindon, United Kingdom

[21] Appl. No.: 451,472

[22] Filed: May 26, 1995

Related U.S. Application Data

[63] Continuation of Ser. No. 117,125, filed as PCT/GB92/00501, Mar. 22, 1991, abandoned.

[30]     Foreign Application Priority Data

Mar. 22, 1991 [GB] United Kingdom .................... 9106185

[51] Int. Cl.$^6$ ............................. A01N 63/00; C12N 15/86
[52] U.S. Cl. .................. 424/93.2; 435/235.1; 435/320.1; 424/93.6
[58] Field of Search ................................ 435/69.1, 91.32, 435/91.33, 91.4, 91.41, 91.42, 172.1, 172.3, 320.1; 536/23.1, 23.5, 23.7, 23.72; 424/93.2, 93.6

[56]                References Cited

U.S. PATENT DOCUMENTS

| | | | |
|---|---|---|---|
| 4,925,664 | 5/1990 | Jackson et al. | 424/537 |
| 4,960,867 | 10/1990 | Garcia et al. | 530/324 |
| 5,023,328 | 6/1991 | Summers et al. | |

FOREIGN PATENT DOCUMENTS

| | | |
|---|---|---|
| 0 127 839 | 12/1984 | European Pat. Off. . |
| 0 207 165 | 1/1987 | European Pat. Off. . |
| 0 222 279 | 5/1987 | European Pat. Off. . |
| o 225 701 | 6/1987 | European Pat. Off. . |
| 0 321 842 | 6/1989 | European Pat. Off. . |
| 0 327 626 | 8/1989 | European Pat. Off. . |
| 0 337 604 | 10/1989 | European Pat. Off. . |
| 0 345 152 | 12/1989 | European Pat. Off. . |
| 0 359 714 | 3/1990 | European Pat. Off. . |
| 0 374 753 | 6/1990 | European Pat. Off. . |
| 0 397 485 | 11/1990 | European Pat. Off. . |
| 0 417 906 | 3/1991 | European Pat. Off. . |
| 0 421 935 | 4/1991 | European Pat. Off. . |
| 0 572 978 | 12/1993 | European Pat. Off. . |
| 0 608 696 | 8/1994 | European Pat. Off. . |
| 0 621 337 | 10/1994 | European Pat. Off. . |
| 8800-198 | 1/1988 | Netherlands . |
| 2 190 382 | 11/1987 | United Kingdom . |
| WO 86/03779 | 7/1986 | WIPO . |
| 89/01518 | 2/1989 | WIPO . |
| 90/05783 | 5/1990 | WIPO . |
| 90/10075 | 9/1990 | WIPO . |
| 91/00014 | 1/1991 | WIPO . |
| 92/06181 | 4/1992 | WIPO . |
| 92/11363 | 7/1992 | WIPO . |

OTHER PUBLICATIONS

O'Reilly et al, "Overexpression of *Bombyx mori* Prothoracicotropic Hormone Using Baculovirus Vectors", Insect Biochem. Molec. Biol. 25(4):475–485 (1995).

O'Reilly, David R., "Baculovirus–encoded Ecdysteroid UPD–glucosyltransferases", Insect Biochem. Molec. Biol 25(5):541–550 (1995).

Herrmann et al, "The Tolerance of Lepidopterous Larvae to an Insect Selective Neurotoxin", Insect Biochem. 20(6):625–637 (1990).

Dianous et al, "The Effect of the Mode of Application on the Toxicity of *Androctonus australis* Hector Insect Toxin", Pestic. Sci. 23:35–40 (1988).

Bullied et al, "Defective co–translational formation of disulphide bonds in protein disulphide–isomerase–deficient microsomes", Nature 335:649–651 (1988).

Sabatier et al, "Reduction and reoxidation of the neurotoxin II from the scorpion *Androctonus australis* Hector", Int. J. Peptide Protein Res. 30:125–134 (1987).

Bozon et al, "Influence of promoter and signal peptide on the expression and secretion of recombinant porcine LH extracellular domain in baculovirus/lepidopteran cells or the caterpillar system", Journal of Molecular Endocrinology 14:277–284 (1995).

Whitford

OTHER PUBLICATIONS

Merryweather et al, "Construction of genetically engineered baculovirus insecticides containing the *Bacilus thuringiensis* subsp. kurstaki HD–73 delta endotoxin", J. Gen. Virol. 71:1535–1544 (1990).

Martens et al, "Insecticidal Activity of a Bacterial Crystal Protein Expressed by a Recombinant Baculovirus in Insect Cells", Applied and Environmental Microbiology 56(9):2764–2770.

Sanger et al, "DNA sequencing with chain–terminating inhibitors", Proc. Natl. Acad. Sci. USA 74(12):5463–5467 (1977).

Harrap et al, "The Properties of Three Baculoviruses from Closely Related Hosts", Virology 77:14–31 (1977).

Brown and Faulkner "A plaque Assay for Nuclear Polyhedrosis Viruses using a Solid Overlay", J. Gen. Virol. 36:361–364 (1977).

Vaughn et al, The Establishment of Two Cell Lines from the Insect Spodoptera Frugiperda (Lepidoptera; Noctuidae), In Vitro 13(4):213–217.

Martignoni & Iwai, "A Catalogue of Viral Diseases" in Microbiol Control of Pests and Diseases 1970–1980 (ed. H.D. Burges).

Lewis, "Control of the gypsy moth by a baculovirus" in Microbial Control of Pests and Diseases 1970–1980 (ed H.D. Burges).

Couch & Ignoffio, "Formulation of insect pathogens" in Microbial Control of Pests and Diseases 1970–1980 (ed H.D. Burges).

Payne & Kelly, "Identification of Insect and Mite Viruses" in Microbial Control of Pests and Diseases 1970–1980 (ed H.D. Burges).

Hughes & Woods, "A Synchronous Peroral Technique for the Bioassay of Insect Viruses", J. Inv. Path. 37:154–159 (1981).

Grishin, "Structure and Function of *Buthus eupeus* Scorpion Neurotoxins", Int. J. Quant. Chem. XIX, 291–298 (1981).

Smith & Bouse, "Machinery and Factors that Affect the Application of Pathogens" in Microbial Control of Pests and Diseases 1970–1980 (ed H.D. Burges) (1981).

Lester et al, "Purification, Characterization and Action of Two Insect Toxins from the Venom of the Scorpion Buthotus Judaicus", Biochem. Biophys. Acta 701:370–381 (1982).

Lazarovici et al, "Insect Toxic Components from the Venom of a Chactoid Scorpion, Scorpio maurus palmatus (Scorpionidae)", J. Biol. Chem. 257(14):8397–8404 (1982).

Cunningham, "Field Trials with Baculoviruses: Control of Forest Insect Pests", Ch. 8, pp. 335–386 in Microbial and Viral Insecticides (eds Kurstak & Dekker).

Young & Yearian, "Formation of Baculoviruses" Ch. 6 in The Biology of Baculoviruses, vol. II: Practical Application for Insect Control (eds Granados & Federici). (Note: date of publication may be later than 1983; 1983 is date of last cited references.).

Dente et al, "pEMBL: a new family of single stranded plasmids", Nucl. Acids Res. 11(6): 1645–1655 (1983).

Taniguchi et al, "Structure and expression of a cloned cDNA for human interleukin–2", Nature 302:305–310 (1983).

Bystrov et al, ". . . and Scorpion Insectotoxin $I_5A$" in Toxins as Tools in Neurochemistry 19pp (1983).

Ivell & Richter, "Structure and comparison of the oxytocin and vasopressin genes from rat", Proc. Natl. Acad. Sci. USA 81:2006–2010 (1984).

Hunter et al, "Viruses as Pathogens for the Control of Insects", 323–347 in Microbial Methods for Environmental Biotechnology (eds Grainger & Lynch) (1984).

Zlotkin et al, "An Excitatory and a Depressant Insect Toxin from Scorpion Venom both Affect Sodium Conductance and Possess a Common Binding Site", Arch. Bioch. Biophys. 240(2):877–887 (1985).

Yannisch–Perron et al, "Improved M13 phage cloning vectors and host strains: nucleotide sequences of the M13mp18 and pUC19 vectors", Gene 33:103–119 (1985).

Van Hofsten et al, "Molecular cloning, cDNA sequencing , and chemical synthesis of cecropin B from *Hyalophora cecropia*", Proc. Natl. Acad. Sci. USA 82:2240–2243 (1985).

Kunkel, "Rapid and efficient site–specific mutagenesis without phenotypic selection", Proc. Natl. Acad. Sci. USA 82:488–492 (1985).

Hughes et al, "A Modified Droplet Feeding Method for Rapid Assay of *Bacillus thuringiensis* and Baculoviruses in Noctuid Larvae", J. Inv. Path. 48:187–192 (1986).

Possee, "Cell–surface expression of influenza virus haemagglutinin in insect cells using a baculovirus vector", Virus Research 5:43–59 (1986).

Dianous et al, "Re–Examination of the Specificity of the Scorpion Androctonus Australis Hector Insect Toxin Towards Arthropods", Toxicon. 25:411–487 (1987).

Dianous et al, "The Effect of the Mode of Application on the Toxicity of *Androctonus australis* Hector Insect Toxin", Pestic. Sci. 23:35–40 (1988).

Matsuura et al, "Baculovirus Expression Vectors: the Requirements for High Level Expression of Proteins, Including Glycoproteins", J. Gen. Virol. 68:1233–1250 (1987).

Felgner et al, "Lipofection: A highly efficient, lipid–mediated DNA–transfection procedure", Proc. Natl. Acad. Sci. USA 84:7413–7417 (1987).

Sagdiev et al, "A Study of Venom Toxic Components of the Cellar Spider Segestria Florentina", Bioorg. Khim. 13(8):1013–1018 (1987) In Russian but with English Abstract on p. 1018.

Piek et al, "Block of Synaptic Transmission in Insect CNA by Toxins from the Venom of the Wasp Megascolia Flavifrons (FAB.)," Comp. Biochem. Physiol. 87C(2):287–295 (1987).

Piek et al, "The Venom of the Wasp Campsomeris Sexmaculata (F.) Blocks Synaptic Transmission in Insect CNS", Comp. Biochem. Physiol. 87C(2):283–386 (1987).

Nojiri et al, "Cloning and sequence analysis of cDNAs for Neurohypophysial hormones vasotocin and mesotocin for the hypothalmus of toad, *Bufo japonicus*", Proc. Natl. Acad. Sci. USA 84:3043–3042 (1987).

Connick Jr., "Formulation of Living Biological Control Agents with Alginate", Chapter 19 (of what book?), Abstract (1988).

Livingstone & Jones, "Baculovirus expression vectors with single strand capability", Nucl. Acids Res. 17(6):2366 (1989).

Horodyski et al, "Isolation and expression of the eclosion hormone gene from the tobacco hornworm, Manduca sexta", Proc. Natl. Acad. Sci. USA 86:8123–8127 (1989).

Hanzlik et al, "Isolation and Sequencing of cDNA Clones Coding for Juvenile Hormone Esterase from *Heliothis virescens*", J. Biol. Chem. 264(21):12419–12425 (1989).

Adachi et al, "cDNA Structure and Expression of bombyxin, and Insulin–like Brain Secretory Peptide of the Silkmoth *Bombyx mori*", J. Biol. Chem. 264(13):7681–7685 (1989).

Jarvis et al, "Use of Early Baculovirus Promoters for Continuous Expression and Efficient Processing of Foreign Gene Products in Stably Transformed Lepidopteran Cells", Bio/technol. 8:950–955 (1990).

Herrman et al, "The Tolerance of Lepidopterous Larvae to an Insect Selective Neurotoxin", Insect Biochem. 20(6):625–637 (1990).

Dee et al, "Expression and Secretion of a Functional Scorpion Insecticidal Toxin in Cultured Mouse Cells", Bio/technol. 8:339–342 (1990).

Killick, Influence of droplet size, solar ultraviolet light and protectants, and other factors on the efficacy of baculovirus sprays against *Panolis flammea* (Schiff.) (Lepidoptera: Noctuidae), Crop Protection 9:21–28, Abstract.

Bohm et al, "Microencapsulated Biopesticides", Abstr, Pap. Am. Chem. Shell Oil Company. (200 meet., p. 1 AGRO 1990).

Stapleton et al, "Curtatoxins", J. Biol. Chem. 265(4)m: 2054–2057 (1990).

Weyer et al, "Analysis of very late gene expression by *Autographa california* nuclear polyhedrosis virus and the further development of multiple expression vectors", J. Gen. Virol. 71:1525–1534 (1990).

Loret et al, "Neurotoxins Active on Imsects: Amino Acid Sequences, Chemical Modifications, and Secondary Structure Estimation by Circular Dichroism of Toxins from the Scorpion *Androctonus australis* Hector", Biochemistry 29:1492–1501 (1990).

Kawakami et al, "Molecular Cloning of the *Bombyx mori* Prothoracictropic Hormone", Science 247:1333–1335 (1990).

Kitts et al, "Linearization of baculovirus DNA enhances the recovery of recombinant virus expression vectors", Nucl. Acids Res. 18(9):5667–5672 (1990).

Hill–Perkins & Possee, "A baculovirus expression vector derived from the basic protein promoter of *Autograph california* nuclear polyhedrosis virus", J. Gen. Virol. 71:971–976 (1990).

Groebe et al, "Cationic lipid–mediated co–transfection of insect cells", Nucl. Acids Res. 18(13): 4033 (1990).

Advertisement for "Culigel Supersorbent Polymer" (appended to 5. above in 1990 section and 2. above in 1988 section).

McCutchen et al, "Development of a Recombinant Baculovirus Expressing an Insect–Selective neurotoxin: Potential for Pest control", Biotechnol. 9:848–852 (1991).

Tomalski et al, "Insect paralysis by baculovirus–mediated expression of a mite neurotoxin gene", Nature 352:82–85 (1991).

Mante et al, "Agrobacterium–mediated Transformation of Plum (Prunus Domestica L.) Hypocotyl Slices and Regeneration of Transgenic Plants", Bio/technol. 9:853–857 (1991).

Dong et al, "Transformation of Melon (Cucumis Melo L.) and Expression from the Cauliflower Mosaic Virus 35S Promoter in Transgenic Melon Plants", Bio/technol. 9:858–863 (1991).

Lu et al, Agrobacterium–mediated Transformation of Carnation (Dianthus Caryophyllus L.), Bio/technol. 9:864–868 (1991).

Klein et al, "Secretion of Active Bovine Somatotropin in *Escherichia coli*", Bio/technol. 9:869–872 (1991).

Hochberg et al, "Control engineering", Nature 352:16–17 (1991).

"The Use of Viruses for the Control of Insect Pests and Disease Vectors", World Health Organization Technical Report Series No. 531, Geneva (1973).

Cook et al, "Infection of Chicken Erythrocytes with Influenza and Other Viruses", Infection and Immunity 25(1):396–402 (1979).

Hooft van Iddekinge et al, "Nucleotide Sequence of the Polyhedrin Gene of *Autographa californica* Nuclear Polyhedrosis Virus", Virology 131:561–565 (1983).

Kuzio et al, "Nucleotide Sequence of the p10 Polypeptide Gene of *Autographa californica* Nuclear Polyhedrosis Virus", Virology 139:414–418 (1984).

Blissard et al, "Location, Sequence, Transcriptional Mapping, and Temporal Expression of the gp64 Envelope Glycoprotein Gene of the *Orgyia pseudotsugata* Multicapsid Nuclear Polyhedrosis Virus", Virology 170:537–555 (1989).

Smith et al, "Molecular Engineering of the *Autographa californica* Nuclear Polyhedrosis Virus Genome: Delection Mutations Withing the Polyhedrin Gene", Journal of Virology 46(2):584–593 (1983).

Gordon et al, "Phenotypic Characterization and Physical Mapping of a Temperature–Sensitive Mutant of *Autographa californica* Nuclear Polyhedrosis Virus Defective in DNA Synthesis", Virology 138:69–81 (1984).

Fig. 1

```
        MetLeuLeuValAsnGlnSerHisGlnGlyPheAsnLysGluHisThrSerLysMet
        ATGCTACTAGTAAATCAGTCACACCAAGGCTTCAATAAGGAACACACAAGCAAGA
            50        260       270       280       290       300

ValSerAlaIleValLeuTyrValLeuLeuAlaAlaAlaHisSerAlaPheAlaLys
        TGGTAAGCGCTATTGTTTTATATGTGCTTTTGGCGGGCGGCCATTCTGCCTTTGCGA
            310       320       330       340       350       360

LysAsnGlyTyrAlaValAlaAspSerSerGlyLysAlaProGluCysLeuLeuSerAsnTyr
        AAAAAAACGGCTACGCGGGTTGACTCGGGCAAAGCGCCAGAATGTCTACTATCGAACT
            370       380       390       400       410       420

CysAsnAsnGlnCysThrLysValHisTyrAlaAspLysGlyTyrCysCysLeuLeuSer
        ACTGTAACAACCAATGTACTAAAGTTCACTACGCTGACAAAGGCTACTGTTGTCTACTAA
            430       440       450       460       470       480

CysTyrCysPheGlyLeuAsnAspAspLysLysValLeuGluIleSerAspThrArgLys
        GCTGTTACTGTTTTGGCCTAAACGACGACAAAAAGTTCTAGAAATTAGCGGACACTCGTA
            490       500       510       520       530       540

SerTyrCysAspThrThrIleIleAsn *
        AAAGCTACTGTGACACTACTATTATTAACTAA
```

Fig. 2

```
         BamHI                                          AccI
a1. GATCCAAATATGAAAAAAAAACGGCTACGCGGTTGACTCGTCGGGCAAAGCGCCAGAATGT
a2.             GTTTATACTTTTTTTTGCCGATGCGCCAACTGAGCAGCCCGTTTCGCGGTCTTACAGA
              AcNPV

AccI                                              AccI
b3. CTACTATCGAACTACTGTAACAACCAATGTACTAAAGTTCACTACGCTGACAAAGGCTACTGTTGT
b4.      TGATAGCTTGATGACATTGTTGGTTACATGATTTCAAGTGATGCGACTGTTCCGATGACAACAGC

BamHI       AccI                       XbaI
c5. GATCCACGTGACGTGTCTACTAAGCTGTTACTGTTTTGGCCTAAACGACGACAAAAAGTT
c6.      GTGCACTGCACAGATGATTCGACAATGACAAAACCGGATTTGCTGCTGTTTTTCAAGATC

XbaI                                        *  BglIIAccI
d7. CTAGAAATTAGGCGACACTCGTAAAAGCTACTGTGACACTACTATTATTAACTAAAGATCTGG
d8.      TTTAATCGCTGTGTGAGCATTTTCGATGACACTGTGATGATAATAATTGATTTCTAGACCGC
```

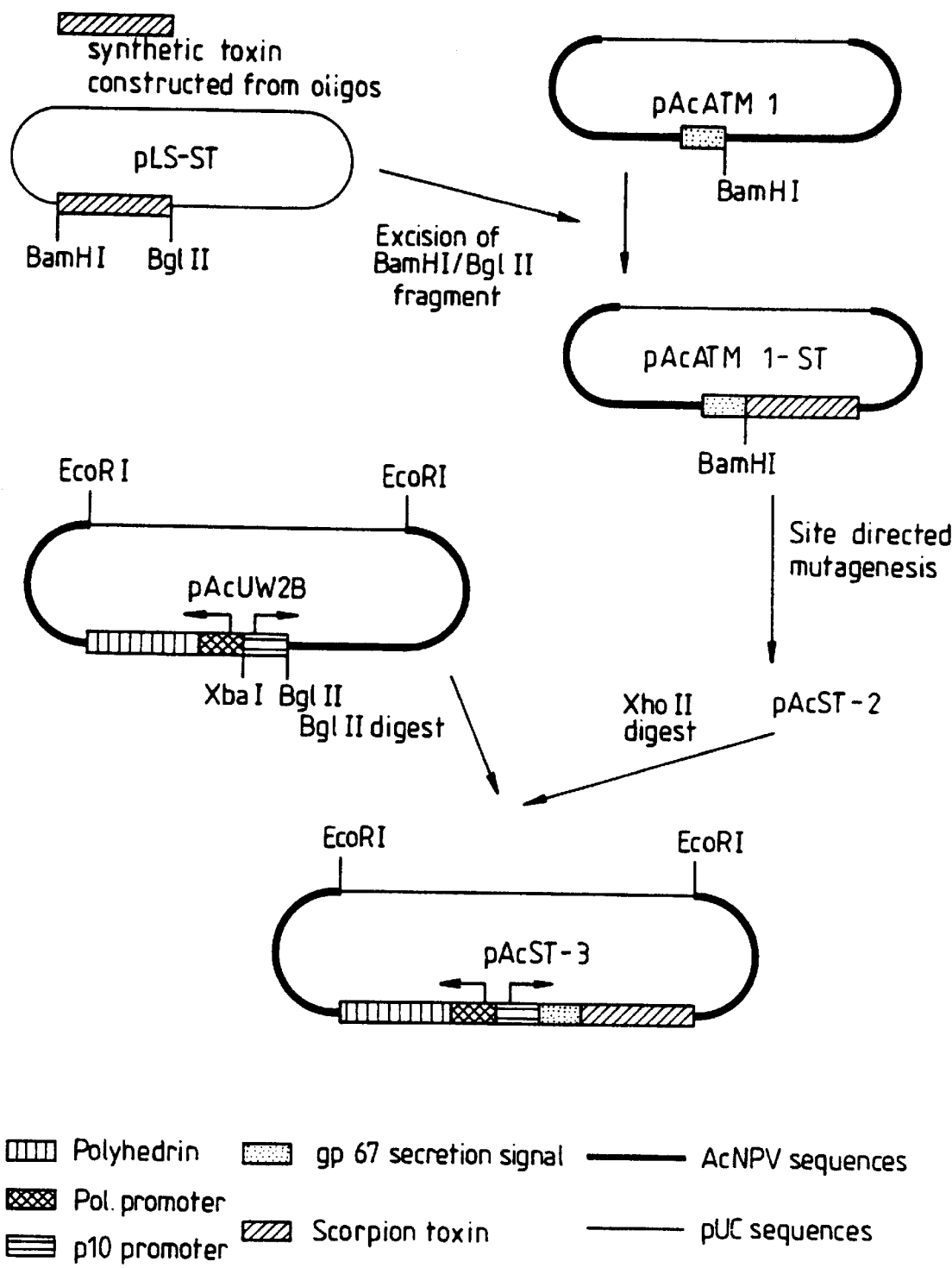

Fig. 4A.

```
TCTAGAGTCGAGCAAGAAAATAAAACGCCAAACGCGTTGGAGTCTTGTGTGCTATTTTAC
Xba I  10        20        30        40        50        60

AAAGATTCAGAAATACGCATCACTTACAACAAGGGGACTATGAAATTATGCATTTGAGG
      70        80        90       100       110       120

ATGCCGGGACCTTTAATTCAACCCAACACAATATATTATAGTTAAATAAGAATTATTATC
      130       140       150       160       170       180

AAATCATTTGTATATTAATTAAAATACTATACTGTAAATTACATTTTATTTACAATCACA
      190       200       210       220       230       240
```

```
         MetLeuLeuValAsnGlnSerHisGlnGlyPheAsnLysGluHisThrSerLysMet
GATCTATGCTACTAGTAAATCAGTCACACCAAGGCTTCAATAAGGAACACACAAGCAAGA
Bgl II  50       260       270       280       290       300
```

```
  ValSerAlaIleValLeuTyrValLeuLeuAlaAlaAlaAlaHisSerAlaPheAlaLys
TGGTAAGCGCTATTGTTTTATATGTGCTTTTGGCGGCGGCGGCATTCTGCCTTTGCGA
       310       320       330       340       350       360
```

```
  LysAsnGlyTyrAlaValAspSerSerGlyLysAlaProGluCysLeuLeuSerAsnTyr
AAAAAAACGGCTACGCGGTTGACTCGTCGGGCAAAGCGCCAGAATGTCTACTATCGAACT
       370       380       390       400       410       420
```

```
  CysAsnAsnGlnCysThrLysValHisTyrAlaAspLysGlyTyrCysCysLeuLeuSer
ACTGTAACAACCAATGTACTAAAGTTCACTACGCTGACAAAGGCTACTGTTGTCTACTAA
       430       440       450       460       470       480
```

```
  CysTyrCysPheGlyLeuAsnAspAspLysLysValLeuGluIleSerAspThrArgLys
GCTGTTACTGTTTTGGCCTAAACGACGACAAAAAGTTCTAGAAATTAGCGACACTCGTA
       490       500       510       520       530       540
```

```
  SerTyrCysAspThrThrIleIleAsn***
AAAGCTACTGTGACACTACTATTATTAACTAAAGATCT
       550       560       570  Bgl II
```

Unmutated sequence at junction.

```
    HisSerAlaPheAla                LysLysAsnGlyTyr
CATTCTGCCTTTGCGgatcaaatatgAAAAAAAACGGCTAC
       350                           370
```

Oligonucleotide GP67-SC.Tox used for mutagenesis.

CATTCTGCCTTTGCGAAAAAAACGGCTAC

Fig. 4c

P10 promoter

```
GAGCAAGAAGAAATAAAACGCCAAACGCGTTGGAGTCTTGTGTGCTATTTTACAAAGATTCA
GGAAATACGCCATCACTTACACAAGGGGACTATGAAATTATGCATTGA GGATGCCGG
GGACCTTTAATTCAACCCACACAATATATT ATAGTTAAAT AAGAATTATTATCAAAT
CATTGTATTATTAATTAAATACTATACTGTAAATTACATTTTATTTACAATCAC
```

Secretion signal gP67

```
            M  L  L  V  N  Q  S  H  Q  G  F  N  K  E  H  T  S  K
agatctATGCTACTAGTAAATCAGTCACACCAAGGCTTCAATAAGGAACACACAAGCAAG
 M  V  S  A  I  V  L  Y  V  L  L  A  A  A  H  S  A  F  A
ATGGTAAGCGCTATTGTTTTATATGTGCTTTTGGCTGCAGCGCATTCTGCCTTTGCG
```

AaIT

```
 K  K  N  G  Y  A  V  D  S  S  G  K  A  P  E  C  L  L  S  N
AAAAAAAACGGCTACGCGGTTGACTCGTCGGGCAAAGCGCCAGAATGTCTACTATCGAAC
 Y  C  N  N  Q  C  T  K  V  H  Y  A  D  K  G  Y  C  C  L  L
TACTGTAACAACC

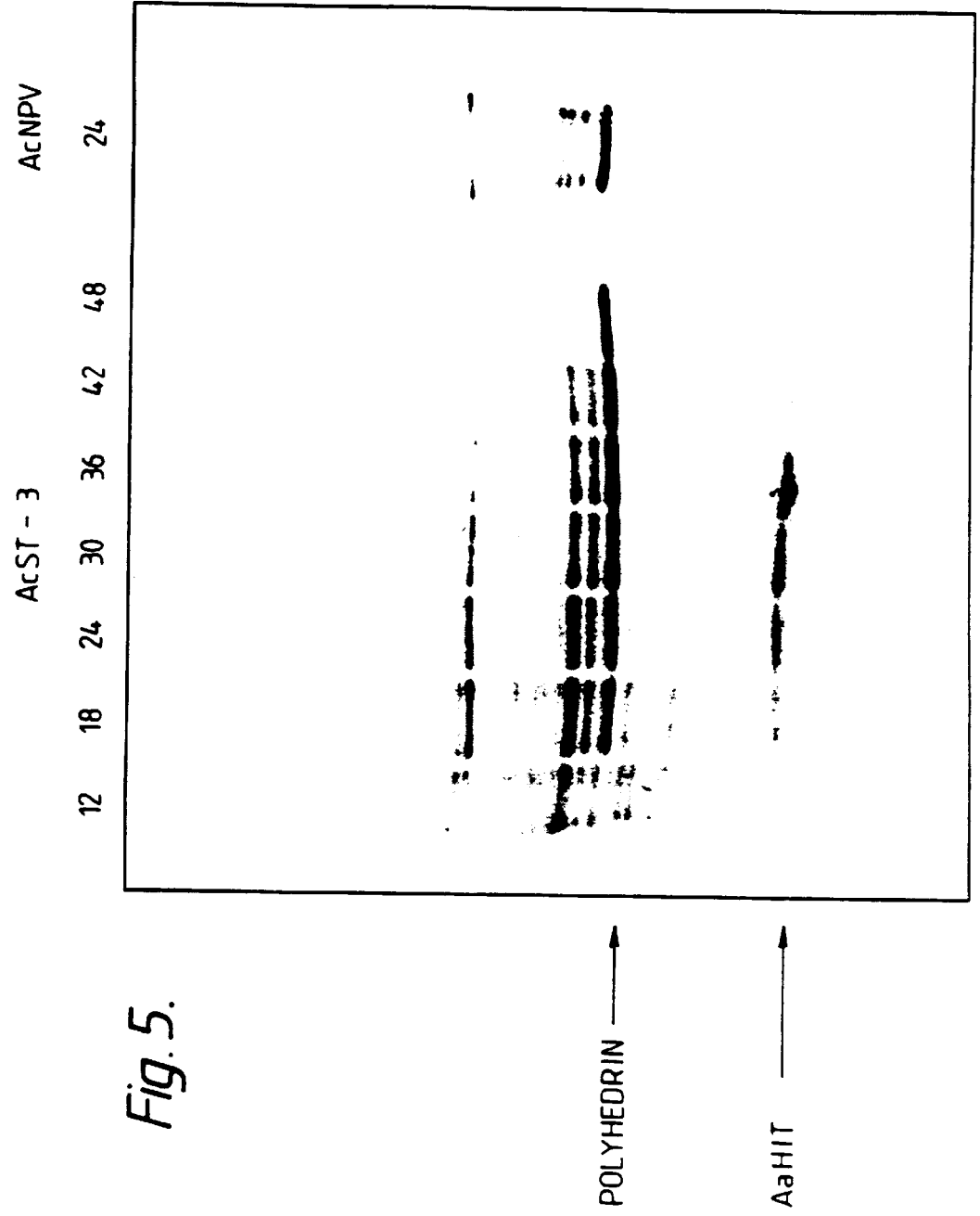

Fig.9a

P10 promoter
GAGCAAGAAAATAAAACGCCCAAACGCGTTGGAGTCTCTTGTGTGCTATTTACAAAGATTCA
GGAAATACGCATCACTTACACAAGGGGACTACTATGAAATTATGCATTTGA GGATGCCGG
GGACCTTTAATTCAACCCAACACAATATATT ATAGTTAAAT AAGAATTATTATCAAAT
CATTGTATTATTAATTAAAATACTATACTGTAAATTACATTTTATTTACAATCAC Insertion IL2 secretion signal +AaIT
IL2 secretion signal
```
        M   Y   R   M   Q   L   L   S   C   I   A   L   S   L   A   L   V   T
ggatccATGTACAGGATGCAACTCCTGTCTTGCATTGCACTAAGTCTTGCACTTGTCACA
   N   S   A
AACAGTGCA
```

AaIT
```
 K   K   N   G   Y   A   V   D   S   S   G   K   A   P   E   C   L   L   S   N
AAAAAAAACGGCTACGCGGTTGACTCGTCGGGCAAAGCGCCAGAATGTCTACTATCGAAC
 Y   C   N   Q   C   T   K   V   H   Y   A   D   K   G   Y   C   C   L   L
TACTGTAACAACCAATGTACTAAAGTTCACTACGCTGACAAAGGCTACTGTTGTCTACTA
 S   C   Y   C   F   G   L   N   D   D   K   K   V   L   E   I   S   D   T   R
AGCTGTTACTGTTTTGGCCTAAACGACGACAAAAAGTTCTAGAAATTAGCGACACTCGT
 K   S   Y   C   D   T   T   I   I   N   *
AAAAGCTACTGTGACACTACTATTATTAACTAAagatct
```

Fig.10a

P10 promoter
GAGCAAGAAATAAAACGCCAAACGCGTTGGAGTCTTGTGTGCTATTTTACAAAGATTCA
GGAAATACGCATCACTTACAACAAGGGGACTATGAAATTATGCATTGA GGATGCCGG
GGACCCTTTAATTCAACCAACACAATATATT ATAGTTAAAT AAGAATTATTATCAAAT
CATTGTATTATTAATTAAAATACTATACTGTAAATTACATTTTATTTACAATCAC Insertion JHE secretion signal +AaIT
JHE secretion signal
         M   T   S   H   V   L   A   F   L   L   H   A   C
agatCTAAATATGACTTCACACGTACTCGCCTTCCTTCTACACGCGTGT
 T   A   L   A
ACAGCGCTGGCA AaIT
    K   K   N   G   Y   A   V   D   S   S   G   K   A   P   E

Fig.11a

P10 promoter
GAGCAAGAAATAAAACGCCAAACGCGTTGGAGTCTTCTGTGTGCTATTTTACAAAGATTCA
GGAAATACGCATCACTTACAACAAGGGGGACTATGAAATTATGCATTTGA GGATGCCGG
GGACCCTTTAATTCAACCCAACACACAATATATT ATAGTTAAAT AAGAATTATTATCAAAT
CATTGTATTATTAATTAAAATAATACTATACTGTAAATTACATTTTATTTACAATCAC Insertion of ST secretion signal + AaHIT
AaHIT natural secretion signal

```
       M   K   F   L   L   L   F   L   V   V   L   P   I   M   G   V   L   G
ggatccATGAAATTTCTCCTATTGTTTCTCGTAGTCCTTCCAATAATGGGGGTGCTTGGC
```

AaHIT
```
  K   K   N   G   Y   A   V   D   S   S   G   K   A   P   E   C   L   L   S   N
AAAAAAAACGGCTACGCGGTTGACTCGTCGGGCAAAGCGCCAGAATGTCTACTATCGAAC
  Y   C   N   Q   C   T   K   V   H   Y   A   D   K   G   Y   C   C   L   L
TACTGTAACCAATGTACTAAAGTTCACTACGCTGACAAAGGCTACTGTTGTCTACTA
  S   C   Y   C   F   G   L   N   D   D   K   K   V   L   E   I   S   D   T   R
AGCTGTTACTGTTTTGGCCTAAACGACGACAAAAAGTTCTAGAAATTAGCGACACTCGT
  K   S   Y   C   D   T   T   I   I   N   *
AAAAGCTACTGTGACACTACTATTATTAACTAAagatct
```

Fig. 12A

P10 promoter
GAGCAAGAAATAAAACGCCAAACGCGTTGGAGTCTTGTGTGCTATTTTACAAAGATTCA
GGAAATACGCATCACTTACAACAAGGGGACTATGAAATTATGCATTTGA GGATGCCGG
GGACCTTTAATTCAACCCAACACACAATATATT ATAGTTAAAT AAGAATTATTATCAAAT
CATTGTATTATTAATTAAAATACTATACTGTAAATTACATTTTATTTACAATCAC Insert of CP2 secretion signal + AaHIT
CP2 secretion signal

```
          M   F   K   F   V   M   I   L   A   V   V   G   V   A   T   A
ggatccATGTGTTTAAATTCGTTATGATTCTAGCGGTTGTTGGCGTTGCCACAGCG
```

AaHIT
```
   K   K   N   G   Y   A   V   D   S   S   G   K   A   P   E   C   L   L   S   N
AAAAAAAACGGCTACGCGGTTGACTCGTCGGGCAAAGCGCCAGAATGTCTACTATCGAAC
   Y   C   N   Q   C   T   K   V   H   Y   A   D   K   G   Y   C   C   L   L
TACTGTAACAACCAATGTACTAAGTTCACTACGCTGACAAAGGCTACTGTTGTCTACTA
   S   C   Y   C   F   G   L   N   D   D   K   K   V   L   E   I   S   D   T   R
AGCTGTTACTGTTTTGGCCTAAACGACGACAAAAAAGTTCTAGAAATTAGCGACACTCGT
   K   S   Y   C   D   T   T   I   I   N   *
AAAAGCTACTGTGACACTACTATTATTAACTAAagatct
```

Fig. 13A

P10 promoter

GAGCAAGAAAATAAAACGCCAAACGCGTTGGAGTCTTGTGTGCTATTTTACAAAGATTCA
GGAAATACGCATCACTTACAACAAGGGGGACTATGAAATTATGCATTTGA GGATGCCGG
GGACCCTTTAATTCAACCAACACACATATATT ATAGTTAAAT AAGAATTATTATCAAAT
CATTGTATTATTAATTAAAATACTATACTGTAAATTACATTTTATTTACAATCAC

Insertion of oxytocin secretion signal + AaHIT
Oxytocin secretion signal

```
             M   A   C   P   S   L   A   C   C   L   L   G   L   L   L   A   L   T   S   A
ggatccATGGCCTGCCCCAGTCTCGCTTGCTGTGGCCTACTGGCTCTGACCTCCGCC
```

AaHIT

```
   K   K   N   G   Y   A   V   D   S   S   G   K   A   P   E   C   L   L   S   N
AAAAAAAACGGCTACGCGGGTTGACTCGTCGGGCAAAGGCCCAGAATGTCTACTATCGAAC
   Y   C   N   Q   C   T   K   V   H   Y   A   D   K   G   Y   C   C   L   L
TACTGTAACCAACCAATGTACTAAAGTTCACTACGCTGACAAAGGCTACTGTTGTCTACTA
   S   C   Y   C   F   G   L   N   D   D   K   K   V   L   E   I   S   D   T   R
AGCTGTTACTGTTTTGGCCTAAACGACGACAAAAAAGTTCTAGAAATTAGGCGACACTCGT
   K   S   Y   C   D   T   T   I   I   N   *
AAAAGCTACTGTGACACTACTATTATTAACTAAagatct
```

Fig. 14.a

Basic Protein Promoter
```
CCAAATTCCGTTTGCCGACGATGCAGAGTTTTGAACAGGCTGCTCAAACACATAGATCC
GTACCCGCTCAGTCGGATGTATTACAATGCAGCCAATACCATGTTTTACACGACTATGGA
AAACTATGCCGTGTCCAATTGCAAGTTCAACATTGAGGATTACAATAACATATTTAAGGT
GATGGAAAATATTAGGAAACACAGCAACAAAAATTCAAACGACCAAGACGAGTTAAACAT
ATATTTGGGAGTTCAGTCGTCGAATGCAAAGCGTAAAAAAATATTAATAAGGTAAAAATTA
CAGCTACATAAATTACACAATTTAAACG
```
P10 Promoter
```
GATCTGATAAGAATTATTATCAAATCATTTGTATATTAATTAAAATACTATACTGTAAAT
TACATTTTATTTACAATCAC
```

Secretion signal gP67
```
                M  L  V  N  Q  S  H  Q  G  F  N  K  E  H  T  S  K
agatctATGCTACTAGTAAATCAGTCACACGTCACACCAAGGCTTCAATAAGGAACACACAAGCAAG
 M  V  S  A  I  V  L  Y  L  V  L  L  A  A  A  H  S  A  F  A
ATGGTAAGCGCTATTGTTTTATATGTGCTTTTGGCGGCGGCCATTCTGCCTTTGCG
```

AaIT
```
 K  K  N  G  Y  A  V  D  S  S  G  K  A  P  E  C  L  L  S  N
AAAAAAAACGGCTACGCGGTTGACTCGTCGGCAAAGCGCCAGAATGTCTACTATCGAAC
 Y  C  N  N  Q  C  T  K  V  H  Y  A  D  K  G  Y  C  C  L  L
TACTGTAACAACCAATGCACTAAAGTTCACTACGCT

Fig. 16.

```
gp67 signal
         MetLeuLeuValAsnGlnSerHisGlnGlyPheAsnLysGluHisThrSerLys
AGATCTATGCTACTAGTAAATCAGTCACACCAAGGCTTCAATAAGGAACACAAGCAAG
         10        20        30        40        50        60

MetValSerAlaIleValLeuTyrValLeuLeuAlaAlaAlaHisSerAlaPheAla
ATGGTAAGCGCTATTGTTTTATATGTGCTACTAGCGGCGGCCCATTCTGCCTTTGCA
         70        80        90       100       110       120
SefIT
ArgGlnAspMetValAspGluSerValCysTyrIleThrAspAsnAsnCysAsnGlyGly
CGTCAAGACATGGTTGACGAGAGCGTTTGTTACATTGACAACAACTGCAACGGCGGC
        130       140       150       160       170       180

LysCysLeuArgSerLysAlaCysHisAlaAspProTrpGluLeu *
AAATGCTTGCGTAGCAAAGCATGCCACGCGGACCCATGGGAGCTATAG
        190       200       210       220
```

Fig. 17.

```
OS 3711         CCGTCAAGACATGGTTGACGAGAGCGTTTGTTACATTACTGACAACAACTGCAACGGCGGC
OS 3712 GTACGGCAGTTCTGTACCAACTGCTCTCGCAAACAATGTAATGACTGTTGTTGACGTTGCCGCCG
        Sph I

OS 3711 AAATGCTTGCGTAGCAAAGCATGCCACGCGGACCCATGGGAGCTATAG
OS 3712 TTTACGAACGCATCGTTTCGTACGGTGCGCCTGGGTACCCTCGATATCCTAG
                                                    BamHI
```

Fig.18.

p10 promoter
<u>TCTAGA</u>GTCGAGCAAGAAAATAAAACGCCAAACGCGTTGGAGTCTTGTGTGCTATTTTAC
Xba I    10        20        30        40        50        60

AAAGATTCAGAAATACGCATCACTTACAACAAGGGGGACTATGAAATTATGCATTTGAGG
        70        80        90       100       110       120

ATGCCGGGACCTTTAATTCAACCCAACACAATATATTATAGTTAAATAAGAATTATTATC
      130       140       150       160       170       180

AAATCATTTGTATATTAATTAAAATACTATACTGTAAATTACATTTTATTTACAATCACA
      190       200       210       220       230       240
    gp67
    <u>MetLeuLeuValAsnGlnSerHisGlnGlyPheAsnLysGluHisThrSerLysMet</u>
GATCTATGCTACTAGTAAATCAGTCACACCAAGGCTTCAATAAGGAACACACAAGCAAGA
      250       260       270       280       290       300
                                                          SefIT
   <u>ValSerAlaIleValLeuTyrValLeuLeuAlaAlaAlaAlaHisSerAlaPheAlaArg</u>
TGGTAAGCGCTATTGTTTTATATGTGCTACTAGCGGCGGCGGCGCATTCTGCCTTTGCAC
      310       320       330       340       350       360

GlnAspMetValAspGluSerValCysTyrIleThrAspAsnAsnCysAsnGlyGlyLys
GTCAAGACATGGTTGACGAGAGCGTTTGTTACATTACTGACAACAACTGCAACGGCGGCA
      370       380       390       400       410       420

CysLeuArgSerLysAlaCysHisAlaAspProTrpGluLeu *
AATGCTTGCGTAGCAAAGCATGCCACGCGGACCCATGGGAGCTATAG
      430       440       450       460

Fig.19a

Inserted sequences: gP67 secretion signal +Segestria toxin gP67 secretion signal gatctATGCTACTAGTAAATCAGTCACACCAAGGCTTCAATAAGGAACACACAAGCAA
GATGGTAAGCGCTATTGTTTTATATGTGCTACTAGCGGGGCGGCATTCTGCCTTT
GCA Segestria toxin CGTCAAGAATGGTTGACGAGAGCGTTTGTTACATTACTGACAACAACTGCAACGGCG
GCAAATGCTTGCCTAGCAAAGCATGCCACGCCGACCCATGGGAGCTATAG

BIOLOGICAL CONTROL AGENTS

This is a continuation of application Ser. No. 08/117,125, filed as PCT/GB92/00501 Mar. 22, 1991, now abandoned.

The present invention relates to baculovirus insecticides.

Insect-specific baculoviruses provide an alternative to the use of chemical agents in the control of pests in agriculture. They have been used for this purpose for many years. Baculoviruses have the advantages of selectivity with respect to target organisms and being non-polluting to the environment. They are considered to be safe for use in pest control programmes in the field (WHO, 1973). Their major disadvantage is that they are relatively slow to kill the target insect, thus precluding a rapid cessation of feeding damage. The advent of techniques for the genetic manipulation of baculoviruses has suggested that the effectiveness of these agents might be improved by expressing insect-specific toxins, hormones or enzymes in the host and thus reducing the time required to kill the insect, or at least, preventing it from feeding.

Attempts to modify the effectiveness of baculovirus insecticides have so far met with limited success. Carbonell et al. (1988) expressed an insect specific scorpion toxin from *Buthus eupeus* using *Autographa californica* Nuclear Polyhedrosis Virus (AcMNPV), but failed to detect biological activity of the recombinant toxin. Maeda (1989) inserted a diuretic hormone gene from *Manduca sexta* into *Bombyx mori* MNPV and reduced the time taken to kill the host by 20%. Hammock et al. (1990) expressed juvenile hormone esterase in *Trichoplusia ni* larvae using a polyhedrin-negative AcMNPV and detected a significant reduction in weight gain at high doses of virus. Finally, Merryweather et al. (1990) and Martens et al. (1990) inserted the *Bacillus thuringiensis* delta endotoxin gene into AcMNPV and produced authentic bacterial toxin, which although toxic for insect larvae per se, did not modify the effectiveness of the virus.

We have now placed a synthetic gene encoding an insect-specific toxin under the control of a baculovirus promoter in a recombinant ACMNPV. We found that there was a marked increase in pathogenicity to insects if the toxin coding sequence was fused to a sequence encoding a signal peptide which mediates protein secretion. This finding has general applicability.

Accordingly, the present invention provides a recombinant baculovirus which, in insect cells infected therewith, expresses a foreign protein comprising an insecticidal toxin, or a functional derivative thereof, provided with a signal peptide such that the toxin or derivative thereof is secreted from the insect cells.

The invention also provides a method of controlling insects at a locus, which method comprises providing at the locus an effective amount of a recombinant baculovirus according to the invention. The insect ingests the recombinant baculovirus, the viral DNA multiplies inside the insect and the toxin is expressed and secreted to kill the insect. Kill occurs more quickly than by use of a recombinant baculovirus in which no secretory signal sequence is provided. This has the important benefit of decreasing the amount of crop damage caused by insect pests prior to their death.

The invention may be applied to any suitable baculovirus of the family Baculoviridae, for example of the genus Baculovirus. The recombinant baculovirus may therefore be an occluded baculovirus. The baculovirus may be a nuclear polyhedrosis virus (NPV), for example AcMNPV, *Bombyx mori* NPV, *Heliothis zea* NPV and *Buzura suppressuria* NPV. The genome of a recombinant NPV according to the invention includes a functional polyhedrin gene. Expression of polyhedrin protein is therefore typically driven by the natural baculovirus polyhedrin promoter. So that the recombinant baculovirus is functional in the environment, the virus must be viable and have the ability to manufacture its protective coat.

The recombinant baculovirus genome also includes a chimaeric gene encoding an insecticidal toxin, or functional derivative thereof, and a signal peptide which mediates secretion of the structural gene from insect cells infected with the recombinant baculovirus. The genome of the recombinant baculovirus therefore may consist of a wild-type genome having inserted therein a chimaeric gene and transcriptional and translational control elements therefor. Generally, the genetic machinery of the wild-type genome is unaffected by the addition of the chimaeric gene with its control sequences. Expression of the proteins naturally encoded by the wild-type genome is not altered. In this way, a viable, stable, infectious recombinant baculovirus is provided.

The toxin can be a neurotoxin, generally a neurotoxin affecting cellular ion channels. A suitable toxin is a toxin which is secreted by the cells which normally produce the toxin. The toxin typically is a polypeptide toxin of a poisonous animal or microorganism. Suitably the toxin, when purified to homogeneity, is toxic to an insect by injection. Preferably the toxin acts selectively against insects and should have no effect on mammals. The recombinant baculovirus may express and secrete two or more toxins.

A preferred class of toxins are polypeptides which are secreted from the cells in which they are synthesised within an animal to a venom sac, from which the toxin is injected into another animal by biting or stinging. The toxin may be a scorpion toxin, spider toxin, a toxin from another class or order of Arthropoda or a toxin of microbial origin, especially a scorpion toxin or a spider toxin. Appropriate toxins therefore are:

1. Insect specific scorpion toxins. (Phylum Arthropoda Class Arachnida Order Scorpionida) *Buthus eupeus* (Middle-Asian scorpion) $I_1A$ (Int. J. Quantum Chemistry 19 (1981) 291–298) (SEQ. ID NO:1)

Met—Cys—Met—Pro—Cys—Phe—Thr—Thr—Arg—Pro—Asp—Met—Ala—Gln—Gln—Cys—Arg—Ala—Cys—Cys—Lys—Gly—Arg—Gly—Lys—Cys—Phe—Gly—Pro—Gln—Cys—Leu—Cys—Gly—Tyr—Asp $I_2A$ (Int. J. Quantum Chemistry 19 (1981) 291–298) (SEQ. ID NO:2)

Ala—Asp—Gly—Tyr—Val—Lys—Gly—Cys—Lys—Ile—Ser—Cys—Phe—Leu—
Asp—Asn—Asp—Leu—Cys—Asn—Ala—Asp—Cys—Lys—Tyr—Tyr—Gly—Gly—
Lys—Leu—Asn—Ser—Trp—Cys—Ile—Pro—Asp—Lys—Ser—Gly—Tyr—Cys—
Trp—Cys—Pro—Asn—Lys—Gly—Trp—Asn—Ser—Ile—Lys—Ser—Glu—Thr—
Asn—Thr—Cys $I_5A$ Toxins as tools in Neurochemistry, Walter de Gruyter, Berlin & New York, 1983, 291–309. Eds Hucho, F. and Ovchinnikov, Y. A. (SEQ. ID NO:3)

Met—Cys—Met—Pro—Cys—Phe—Thr—Thr—Asp—Pro—Asn—Met—Ala—Lys—
Lys—Cys—Arg—Asp—Cys—Cys—Gly—Gly—Asn—Gly—Lys—Cys—Phe—Gly—
Pro—Gln—Cys—Leu—Cys—Asn—Arg

The sequences of $I_3A$ and $I_4A$ are related to $I_1A$.

*Androctonus australis* Hector (AaH IT): see FIG. 1. Two other insect-specific toxins with related amino acid sequences have been isolated from this species, AaH IT1 and AaH IT2 (Loret, 1990).

Leiurus quinquestriatus aquinquestriatus (LqqIT2) (SEQ. ID NO:4)

Asp—Gly—Tyr—Ile—Arg—Lys—Arg—Asp—Gly—Cys—Lys—Leu—Ser—Cys—
Leu—Phe—Gly—Asn—Glu—Gly—Cys—Asn—Lys—Glu—Cys—Lys—Ser—Tyr—
Gly—Gly—Ser—Tyr—Gly—Tyr—Cys—Trp—Thr—Trp—Gly—Leu—Ala—Cys—
Trp—Cys—Glu—Gly—Leu—Pro—Asp—Glu—Lys—Thr—Trp—Lys—Ser—Glu—
Thr—Asn—Thr—Cys—Gly (Zlotkin, E., Kadouri, D., Gordon, D., Pelhate, M., Martin, M. F., Rochat, H., Arch. Biocyhem. Biophys. 240, 877, 1985)

*Buthotus judaicus* (BjIT2) (SEQ. ID NO:5)

Asp—Gly—Tyr—Ile—Arg—Lys—Lys—Asp—Gly—Cys—Lys—Val—Ser—Cys—
Ile(val)—Ile—Ile—Gly—Asn—Glu—Gly—Cys—Arg—Lys—Glu—Cys—Val—
Ala—His—Gly—Gly—Ser—Phe—Gly—Tyr—Cys—Trp—Thr—Trp—Gly—Leu—
Ala—Cys—Trp—Cys—Glu—Asn—Leu—Pro—Asp—Ala—Val—Thr—Trp—Lys—
Ser—Ser—Thr—Asn—Thr—Asn—Gly This toxin has been found to have two isoforms 1 containing Ile at position 15 and 2 Val. (Lester, D., Lazarovici, P., Pelhate, M., Zlotkin, E., Biochim. Biophys. Acta 701, 370, 1982).

L. quinquestriatus habraeus (LqhIT2) (SEQ. ID NO:6)

Asp—Gly—Tyr—Ile—Lys—Arg—Arg—Asp—Gly—Cys—Lys—Val—Arg—Cys—
Leu—Ile—Gly—Asn—Glu—Cys—Asp—Lys—Glu—Cys—Lys—Ala—Tyr—Gly—
Gly—Ser—Tyr—Gly—Tyr—Cys—Trp—Thr—Trp—Gly—Leu—Ala—Cys—Trp—
Cys—Glu—Gly—Leu—Pro—Asp—Asp—Lys—Thr—Trp—Lys—Ser—Glu—Thr—
Asn—Thr—Cys—Gly

Scorpio maurus palmatus (SmpIT2) (SEQ. ID NO:7)

Ala—Leu—Pro—Leu—Ser—Gly—Glu—Tyr—Glu—Pro—Cys—Val—Arg—Pro—
Arg—Lys—Cys—Lys—Pro—Gly—Leu—Val—Cys—Asn—Lys—Gln—Gln—Ile—
Cys—Val—Asp—Pro—Lys (Lazarovici, P., Yanai, P., Pelhate, M., Zlotkin, E., J. Biol. Chem 257 8397, 1982)
2. Insect specific spider toxins (phylum Arthropoda class Arachnida order Araneida) Funnel-web (Agelenid) spider, Hololena curta Curtatoxins CT-I (SEQ. ID NO:8)

Ser—Cys—Val—Gly—Glu—Tyr—Gly—Arg—Cys—Arg—Ser—Ala—Tyr—Glu—
Asp—Cys—Cys—Asp—Gly—Tyr—Tyr—Cys—Asn—Cys—Ser—Gln—Pro—Pro—
Tyr—Cys—Leu—Cys—Arg—Asn—Asn—Asn—NH₂

CT-II (SEQ. ID NO:9)

Ala—Asp—Cys—Val—Gly—Asp—Gly—Gln—Arg—Cys—Ala—Asp—Trp—Ala—
Gly—Pro—Tyr—Cys—Cys—Ser—Gly—Tyr—Tyr—Cys—Ser—Cys—Agr—Ser—
Met—Pro—Tyr—Cys—Arg—Cys—Arg—Ser—Asp—Ser—NH₂

CT-III (SEQ. ID NO:9)
Arg to Lys at position 9 Ala to Phe at position 14 (Stapleton, A., Blankenship, D. T. Ackermann, B. L., Chen, T- M., Gorder, G. W., Manley, G. D. Palfreyman, M. G., Coutant, J. E., Cardin, A. D., J Biol. Chem. 265, 2054, 1990) Cellar spider Segestria florentina (SefIT) (SEQ ID NO:10)

Arg—Gln—Asp—Met—Val—Asp—Glu—Ser—Val—Cys—Tyr—Ile—Thr—Asp—
Asn—Asn—Cys—Asn—Gly—Gly—Lys—Cys—Leu—Arg—Ser—Lys—Ala—Cys—
His—Ala—Asp—Pro—Trp—Glu—Leu (Sagdiev, N. ZH., Valieva, L. A., Korneev, A. S., Sadykov, A. A., Salikhov, SH.I., Bioorg Khim 13, 1013, 1987)
3. Other insect toxin components from Arthropoda Class Insecta Order Hymenoptera The venoms of wasps for example *Campsomeris sex-maculata* and *Megascolia flavifrons* have been shown to contain components which paralyses insects (Piek, T., Hue, B., Mony, L., Nakajaima, T., Pelhate, M., Yasuhara, T., Comp. Biochem. Physiol. 87C, 287, 1987; Piek, T., Hue, B., Pelhate, M., Mony, L., Comp./ Biochem. Physiol. 87C, 283, 1987).
4. Toxins of microbial origin Toxins are produced by microbes which are toxic to insects. Among naturally-occurring toxins are the polypeptide toxins of *Bacillus thuringiensis* var. kurstaki, and var aizawai which are active against lepidoptera. A 40 kdalton toxin has been isolated from *Xenorhabdus luminescens* strain NC-19 which is toxic to *Manduca sexta*. B.t. var israelensis and *B. sphaericus* are active against diptera. Other toxins include those of entomopathogenic fungi, such as beauverin of *Beauveria bassiana* and destruxins of Metarhizium spp..

The toxins which are produced by the microbes may be a precursor or proform of the toxin which requires processing to be toxic by injection in the insect. The genes for toxin crystals from many bacteria have been isolated and sequenced. These include the following:

*Bacillus thuringiensis* var. kurstaki HD-1 and HD-73
*Bacillus thuringiensis* var. aizawai ICI and IPL7
*Bacillus thuringiensis* var. berliner 1715
*Bacillus thurinaiensis* var. israelensis
*Bacillus thuringiensis* var. sotto

*Bacillus thuringiensis* var. morrisoni
*Bacillus sphaericus* 1593

The endotoxin gene may be isolated from plasmids carrying the gene harboured by a B.t. The U.S. Department of Agriculture's *Bacillus thuringiensis* culture collection contains a large number of suitable B.t. varieties.

A functional derivative of an insecticidal toxin may be expressed by a recombinant baculovirus. A "functional derivative" of the toxin is a substance which possesses a biological activity (either functional or structural) which is essentially similar to a biological activity of the toxin. The expression "functional derivative" is to be understood as including "fragments", "variants", "analogues" or "chemical derivatives" of a molecule.

By a "fragment" of a molecule such as the toxin, any polypeptide fragment of the molecule is meant. The term "variants" of a molecule such as the toxin means that it refers to a molecule which is essentially similar in structure and function either to the "essentially similar" to another molecule when both molecules have essentially the same structure and/or when both molecules have essentially the same biovariant when they exhibit a similar activity, even if the structure of one molecule is not reflected in the other, or when the amino acid sequences are not identical. By the "analogues" of the molecule such as the toxin is meant a molecule which is essentially similar in function either to the whole molecule or to a fragment. Here and hereinafter, a molecule is considered to be a "chemical derivative" of another molecule when it contains additional chemical fractions which normally do not form part of the molecule.

The signal peptide enables the toxin to be secreted from the cells in which they are produced. The signal sequence may be a sequence capable of mediating protein secretion from mammalian or insect cells. It may therefore be a mammalian sequence such as the secretory signal sequence for interleukin 2 (IL-2) or an insect sequence such as the secretory signal sequence of juvenile hormone esterase, eclosion hormone or Drosophila cuticle protein. A baculovirus signal sequence is particularly useful such as the secretory signal sequence of the gp67 protein. Suitable signal sequences may therefore be:

1) (SEQ ID NO:11) MetLeuLeuValAsnGlnSerHisGlnGlyPheAsnLysGluHisThrSerLys MetValSerAlaIleValLeuTyrValLeuLeuAlaAlaAlaAlaHisSerAlaPheAla
2) (SEQ. ID NO:12) MetThrSerHisValLeuAlaLeuAlaPheLeuLeuHisAlaCysThrAlaLeuAla
3) (SEQ. ID NO:13) MetAlaGlyLysValThrValAlaPhePheMetPheAlaMetIleAlaPheLeu AlaAsnPheGlyTyrValGluCys
4) (SEQ. ID NO:14) MetLysIleLeuLeuAlaIleAlaLeuMetLeuSerThrValMetTrpvalSerThr
5) (SEQ. ID NO:15) MetIleThrArgProIleIleLeuValIleLeuCysTyrAlaIleLeuMetIle ValGlnSerPheValProLysAlaValAlaLeu
6) (SEQ. ID NO:16) MetAsnPheSerArgIlePhePhePheValPheAlaLeuValLeuAlaLeuSer ThrValSerAlaAlaProGluPro
7) (SEQ. ID NO:17) MetPheLysPheValMetIleLeuAlaValValGlyValAlaThrAla
8) (SEQ. ID NO:18) MetLysPheLeuLeuLeuPheLeuValValLeuProIleMetGlyValLeuGly
9) (SEQ. ID NO:19) MetSerTyrThrAlaLeuAlaValThrPhePheGlyTrpLeuAlaLeuSerSerAla
10) (SEQ. ID NO:20) MetTyrArgMetGlnLeuLeuSerCysIleAlaLeuSerLeuAlaLeuValThr AsnSer
11) (SEQ. ID NO:21) MetAlaCysProSerLeuAlaCysCysLeuLeuGlyLeuLeuAlaLeuThrSer Ala.

References

1) Gp 67 from AcNPV. Whitford, M. et al., 1989.
2) JHE of *Heliothis viriscens*. Hanzlik, T., et al., 1989.
3) Eclosion hormone of *Manduca sexta*. Horodyski, F. M. et al., 1989.
4) Bombyxin (4k-PTTH) of *Bombyx mori*, Adachi, T. et al., 1989.
5) PTTH of *Bombyx mori*, Kawakami, A., et al. 1990.
6) Cecropin B of *Hyalophora cecropia*. van Hofsten, P., et al., 1985
7) CP2 of *Drosophila melanogaster.* Snyder, M. et al., 1982.
8) AaHIT. Bougis, P. E., et al., 1989.
9) Mesotocin of *Bufo japonicus.* Nojiri, H., et al., 1987.
10) IL-2. Taniguchi, T., et al., 1983.
11) Oxytocin of rat. Ivell, R. and Tichter, D., 1984.

The signal peptide is cleavable from the toxin so that the toxin can be secreted. The signal peptide may therefore be fused to the N-terminal or C-terminal amino acid residue of the toxin either directly or via a linker sequence. The linker sequence may have from 1 to 10 amino acid residues, for example from 1 to 5 residues.

A recombinant baculovirus of the invention may be prepared by:

(i) cloning a chimeric gene encoding the foreign protein comprising the toxin, or a functional derivative thereof, and the signal peptide into a baculovirus transfer vector at a restriction site downstream of a promoter capable of directing expression of the foreign protein in insect cells; and (ii) co-transfecting cells susceptible to baculovirus infection with the recombinant transfer vector from step (i) and intact wild-type baculovirus DNA.

Homologous recombination occurs, resulting in a recombinant baculovirus harbouring the chimaeric gene operably linked to a promoter. The chimeric gene is typically isolated for use in the cloning step (i). The recombinant baculovirus may also comprise an expressible polyhedrin gene. This may be achieved by utilising in step (ii) a wild-type baculovirus which incorporates such a gene. Alternatively, a transfer vector may be used in step (i) which further comprises a polyhedrin coding sequence operably linked to a polyhedrin promoter. In that event, a wild-type baculovirus lacking an expressible polyhedrin gene may be used in step (ii). Preferably the recombinant baculovirus incorporates the natural polyhedrin gene therefor. In other words, the polyhedrin coding sequence and polyhedrin promoter are the natural ones for the recombinant baculovirus.

The chimeric gene comprises the coding sequence for the toxin, or a functional derivative thereof. This coding sequence, or the entire chimeric gene, may be synthesised. Oligonucleotides which, in total, correspond to the desired sequence are synthesised and annealed. For this purpose, the codon preferences for the particular baculovirus into which the coding sequence is to be inserted are preferably adopted. The coding sequence, or the entire structural gene, may be synthesised with an additional 3'-terminal codon for glycine, or an equivalent sequence, which can be post-translationally modified to —$NH_2$. A translational stop codon is provided. The toxin gene may be cloned using techniques available in the art. If the toxin gene is synthesised alone, it is ligated to an appropriate secretory signal coding sequence.

The secretory signal sequence is present to ensure that the toxin is secreted from cells of an insect infected with a recombinant baculovirus of the invention. A candidate signal sequence may be tested by constructing a recombinant baculovirus, infecting *Spodoptera frugiperda* cells therewith and testing the supernatant from cultures of infected *S. frugiperda* cells for secreted toxin. Alternatively the haemolymph may be recovered from insects infected with the recombinant baculovirus, injected into sensitive insects and toxicity assessed. The toxin may be injected into larvae or adults. For a toxin active against Diptera, the test insects may be *M. domestica*. Other appropriate insects may be selected as test species for other toxins as necessary.

The chimeric gene is provided with transcriptional and translational control sequences, including a promoter. The promoter is selected so that it can direct protein expression in the cells of an insect infected with a recombinant baculovirus. The promoter may therefore be a baculovirus promoter, for example a baculovirus promoter selected from the four phases of virus gene expression in infected cells (Blissard and Rohrmann, 1990): Phase 1 (immediate early gene promoter). 1. Immediate early gene 1, 2, Immediate early gene N. Phase 2. (Delayed early gene promoters). 1. The 39K gene Phase 3 (late gene promoters) 1. gp67 gene. 2. Basic protein gene. 3. Capsid protein gene. Phase 4. (Very late gene promoters). 1. Polyhedrin gene. 2. P10 gene.

Preferably the baculovirus promoter is a promoter for a gene which is not essential for infectious virus particle formation, but a copy of a promoter from an essential gene may also be used. We have found the P10 promoter useful. Two promoters may be provided in tandem.

The chimaeric gene and promoter therefor are provided in a baculovirus transfer vector. An appropriate transfer vector of the type also comprising an expressible polyhedrin gene is pAcUW2B (Weyer et al, 1990). This vector comprises a complete copy of the polyhedrin gene and, in the opposite orientation, a copy of the P10 promoter and a BglII cloning site with SV40 transcription termination sequences. In general, a class of suitable transfer vectors in which two baculovirus promoters are used for gene expression is disclosed in WO 89/01518.

Cells susceptible to baculovirus infection are transfected with the recombinant transfer vector incorporating the chimeric gene and are infected with a wild-type baculovirus in step (ii) above. The susceptible cells are typically cells of an insect cell line, suitably *Spodoptera frugiperda* cells. After homologous recombination has occurred, a recombinant baculovirus according to the invention can be isolated.

The recombinant baculovirus is stable. In other words, the recombinant baculovirus is sufficiently stable for practical use. A polyhedrin-negative NPV does not have sufficient stability for practical use. The recombinant baculovirus is also infectious. The recombinant baculovirus can infect any susceptible insect. The foreign protein comprising the toxin is expressed within and secreted from cells of the insect. The toxin causes the death of the insect.

The recombinant baculovirus is therefore used to control insect pests. An effective amount is applied to a locus, such as to a crop or to a weed species which acts as a host for the insect pests and in particular a crop suffering from infestation by an insect pest. Alternatively, the recombinant baculovirus may be applied to insects, for example trapped or laboratory bred insects, which are then released at the locus to infect subsequent generations. Dose levels of recombinant virus are typically from $10^8$ to $10^{13}$ PIB's per acre. An appropriate baculovirus is selected depending upon the insect to be eradicated. The recombinant baculovirus is typically supplied by spraying but may be applied as a bait or dust. The recombinant baculovirus is ingested by insect larvae so therefore should be applied to an appropriate locus during a period in which hatching of insect eggs is predicted. This period typically lasts for from two to four weeks. The virus may be used alone or in combination with other biological control agents or chemical insecticides.

Depending on the baculovirus chosen this method of control can be applied to insects from the orders:

Coleoptera

Diptera

Hymenoptera

Neuroptera

Trichoptera and particularly Lepidoptera.

By selection of an appropriate baculovirus, many important crop and forest pests can be controlled using this method, including the following:

*Neodiprion sertifer*

*Estigmene acrea*

*Pectinophora gossypiella*

*Plutella xylostella*

*Aryresthia conjugella*

*Cydia molesta*

*C. pomonella*

*Pieris brassicae*

*Manduzca sexta*

*Heliothis armigera*, zea, virescens

*Mamestra brassicae*

*Spodoptera littoralis*, exigua, litura, exempta, mauritia

*Trichoplusia ni*

*Diparopsis watersi*

The recombinant baculovirus of the invention may consequently be themselves used as insecticides in the general manner in which the unmodified native viruses may be used, i.e. by application of an effective amount to the locus of insects susceptible to infection by the virus. The recombinant viruses have been found viable or competent for such purposes by containing native DNA sequences for reproduction, lethal infestation and expression of toxin polypeptide. The recombinant viruses may be constructed to express and secrete two or more toxins.

Insecticidal compositions containing the recombinant baculovirus in an insecticidally effective amount will typically comprise inert carriers such as clay, lactose and proteinaceous materials such as defatted soybean powder to assist in application, particularly those carriers such as proteinaceous materials which are feeding attractants and which may enhance stability of the contained baculoviruses. Such compositions are desirably stored at lower temperatures, e.g. 14° C. to −20° C., to enhance preservation of the viruses.

The compositions provided by the invention may be particulate compositions in that the compositions may be composed of a multiplicity of fine particles in which the baculovirus is secured in a clay and/or protein matrix. The term "secured" as used herein in connection with such particles embraces an imbedding in the matrix with some portion of the baculovirus exposed at the surface of the particle and also embraces a complete encapsulation of the baculovirus in the matrix, the latter condition being preferred and also predominant in the particles of the invention. The particles in the composition are advantageously characterised by a fine size not exceeding 150 microns up to 150 microns and it is a further feature of the invention that satisfactory compositions having particle size of from 5 to 100, preferably 5 to 50 microns and particularly 5 to 25 microns, can be readily produced.

The matrix material constitutes 65 to 99.9 percent by weight of the total weight of the baculovirus and matrix material in this embodiment of the compositions of the invention, preferably 85% to 99% by weight. The clay employed in the composition may be any of the commercially available processed clays of a fine, essentially powdered nature including, by way of illustration, Kaoline clays, Olancha clays, Attapulgus clays and Betonite clays. The preferred clays are Olancha and Attapulsites. The vegetable protein employed as matrix material may also be from any of a wide variety of sources of protein which have been processed into a fine, essentially powdered form. The materials are preferably defatted or otherwise substantially fat-free. Vegetable protein sources which may be mentioned by way of illustration include soybeans, cottonseeds, sunflower seeds and extracts of various yeasts. The preferred vegetable proteinaceous materials are soy protein and cottonseed protein, preferably those from a defatted source, more preferably defatted soybean protein. Representative of animal proteins are skim milk, casein and egg albumin. The proteinaceous material as obtained from a natural source may contain substantial amounts of non-proteinaceous material and the terms "protein" and "proteinaceous material" as used herein generally contemplate materials containing as little as about at least 25% by weight of actual protein. Very suitable materials such as the preferred vegetable proteins usually contain between 40% to 75% actual protein.

While individual particles and the overall composition may have relatively low concentrations of the baculovirus, it is desirable from a minimum practical standpoint that the compositions contain the active equivalent of an LD50 of at least 1.0 microgram/milliliter ($\mu$g/ml). The potency of the compositions may suitably range from 0.001 μg/ml up to 1.0 μg/ml, and is usually in the range of from 0.003 μg/ml to 0.4 μg/ml. The measurement of insecticidal activity or potency used and referred to is based on determination of the LD50 value reported micrograms per ml (μg/ml) of diet required to provide a level dose for 50 percent of the first instar larvae grown at a temperature of 30° C. The method is basically described in J. Insect Pathology; 6, 737–45 (1965) in connection with *Trichopusia ni* NPV potency estimation.

The particulate compositions provided by the invention exhibit a desired amount of insecticidal potency and are generally characterised by improved resistance to potency degradation by photo-inactivation and heat denaturation. Other properties of the compositions, particularly the physical properties, will vary depending upon various factors including particularly the materials employed for the matrix. Compositions in which the matrix is composed only of a clay are generally characterised by good wettability but tend to have less stickability and may, in some cases, be composed of softer particle. On the other hand, compositions in which the matrix is composed only of a vegetable protein may be generally characterised by good stickability and hardness but tend to be less wettable. Compositions containing large amounts of animal protein tend to have good stickability but poor wettability and hardness. Accordingly, the particularly preferred matrix materials are selected from the group consisting of vegetable protein, clay and mixtures thereof. It has also been found that compositions in which the matrix is composed of an intimate mixture of both a vegetable protein and clay have the advantage of offering good wettability, stickability and hardness as well as other desirable properties. Accordingly, the especially preferred compositions of the invention are those in which the matrix is composed of a mixture of both a vegetable protein and clay. The ratio by weight of vegetable protein to clay may range from 0.1 to 10 parts of protein per parts by weight of clay and is preferably in the range of from 0.3 to 4 parts of vegetable protein per part of clay, more preferably 0.5 to 3 parts by weight of clay.

The baculovirus of the invention may be encapsulated in a biodegradable polymer, for example an alginate of Culigel (Trade Mark). An ultraviolet light screen and/or a feeding stimulant may be incorporated in the polymer. A particulate sun-shield such as carbon, carbon-based dyes, aluminium oxide, titanium dioxide, a clay, flour or a fluorescent material may be present in the polymer, therefore.

The following Example illustrates the invention. In the accompanying drawings:

BRIEF DESCRIPTION OF THE DRAWINGS

FIG. 1 (SEQ ID NO:22 and SEQ. ID NO:23) shows the AcMNPV gp67 signal sequence and AaHIT coding sequence. The gp67 signal peptide is underlined with the two potential translation initiation codons in bold type face.

FIG. 2 shows the sequence of the synthetic oligonucleotides used in the construction of the AaHIT gene. The nucleotide sequences are shown in the 5'-3' direction (a1, b3, c5 and d7) (SEQ. ID NOS:24, 26, 28 and 30) and in the 3'-5' direction (a2, b4, c6 and d8) (SEQ. ID NOS:27, 29, 31). Restriction enzyme sites critical for the assembly of the toxin gene are shown above the sequence. The translation initiation codon is underlined and the translation stop codon (TAA) is indicated by an asterix above the second nucleotide. The 'stuffer' region between the BamH1 and Acc1 sites was inserted to facilitate a double digest of these two sites needed in the construction. The oligonucleotides were inserted sequentially into pUC18 polycloning site. d7/d8 were inserted between the Acc1 and Xba1 sites in pUCIS (the Acc1 site was constructed to be destroyed on insertion) forming pSTD. c5/c6 were inserted between the BamH1 and Xba1 site of pSTD to form pSTDC. This was digested with BamH1 and Acc1 to release the 'stuffer' region and a1/a2 were cloned into these sites to form PSTDCA. This was digested with Acc1 and b3/b4 were inserted to form pLS-ST.

FIG. 3 (Parts A–B)

FIG. 3b shows the construction of pAcST-3. The synthetic AaHIT was removed from pLS-ST and inserted at the BamH I site of pAcATM1 to derive pAcATM-1-ST. Site directed mutagenesis was performed on the junction between the gp67 secretion signal and the AaHIT coding region to provide a favorable protease cleavage site within the modified plasmid pAcST-2. The modified gp67 - AaHIT coding region was removed from pAcST-2, and inserted within pAcUW2B to derive pAcST-3.

FIG. 5 demonstrates the expression of proteins in virus infected *S. frugiperda* (Sf) cells. Cells were infected with AcST-3 or wild type virus and pulse labelled with $^{35}$S-Cysteine for 1 hour at various times post infection as described in the methods. Proteins were separated on a 10–30% polyacrylamide gradient gel before exposure to X-ray film. The position of AaHIT and polyhedrin protein are indicated.

Figure 10:
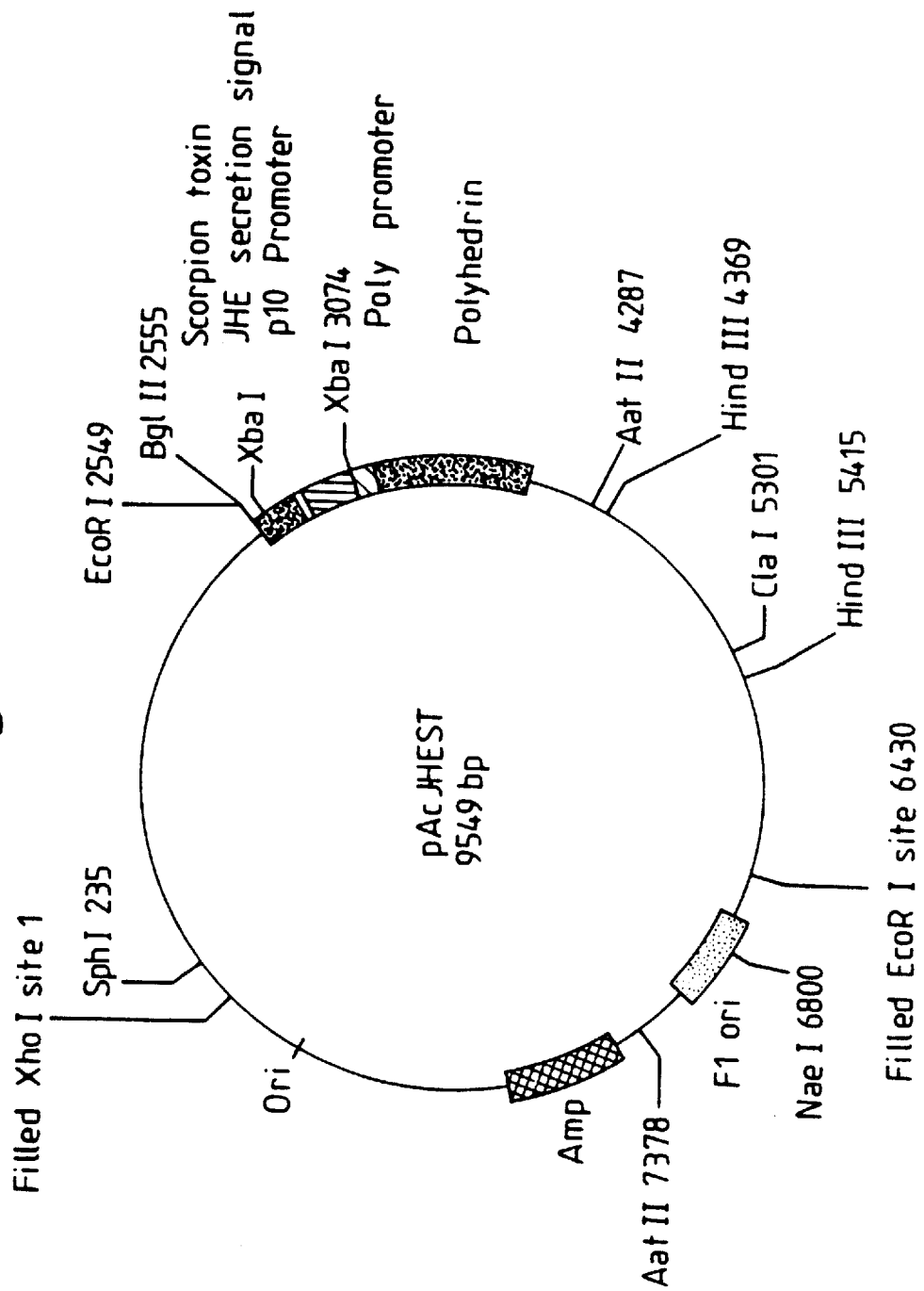

FIG. 10 shows the nucleotide sequence of the AcMNPV p10 gene promoter (SEQ. ID NO:38) in association with the juvenile homrone esterase signal peptide coding region (SEQ. ID NO:45 and 46) and AaHIT coding region (SEQ. ID NOS:41 and 42). Above the sequence is a plasmid restriction map of the transfer vector (pAcJHEST) used to derive the recombinant virus.

Figure 11:
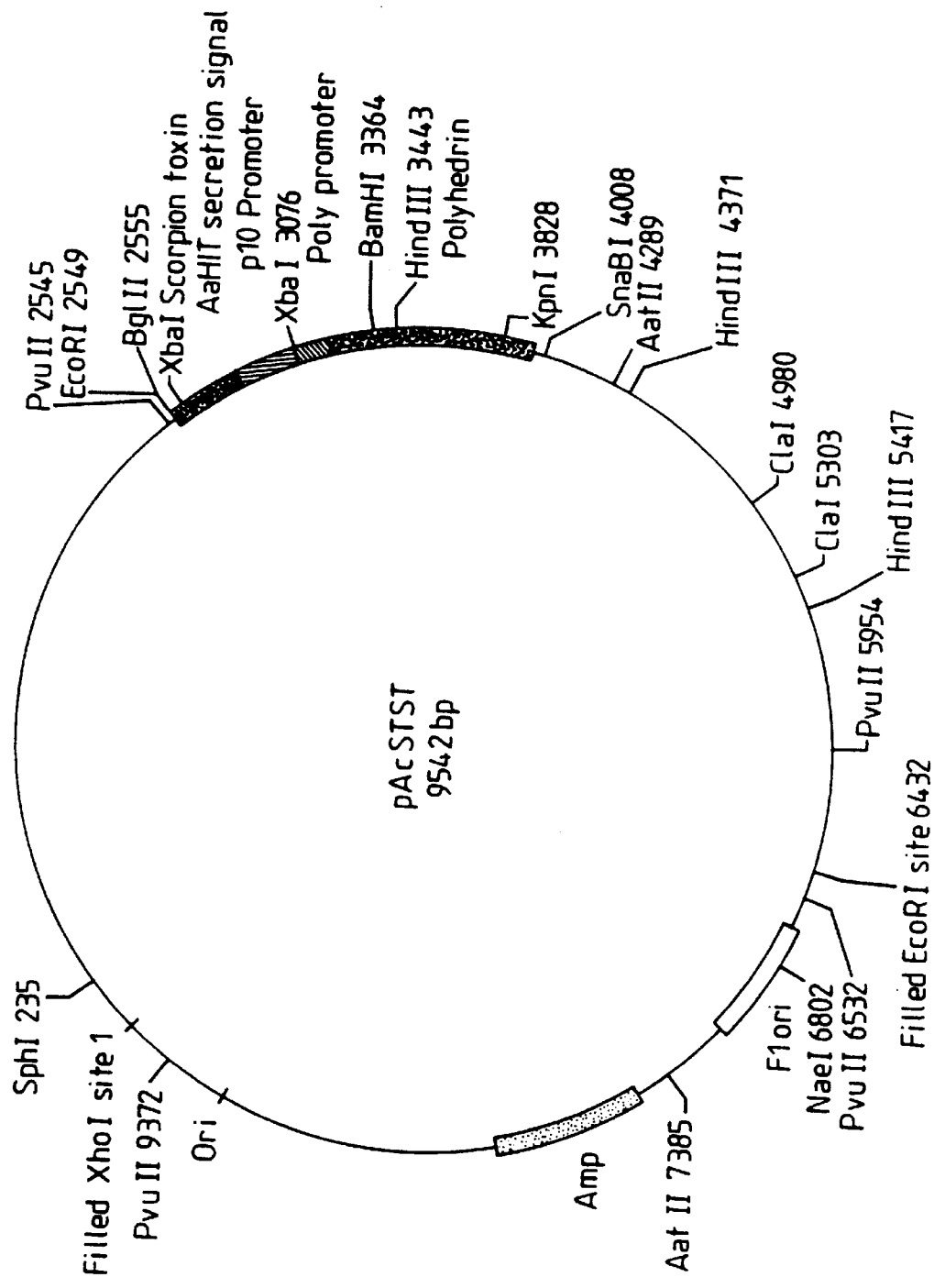

FIG. 11 shows a restriction map of pAcSTST and the sequences of the p10 promoter (SEQ. ID NO:38), AaHIT signal peptide (SEQ. ID NO:47) and AaHIT coding region (SEQ. ID NO:41 and 42).

Figure 12:
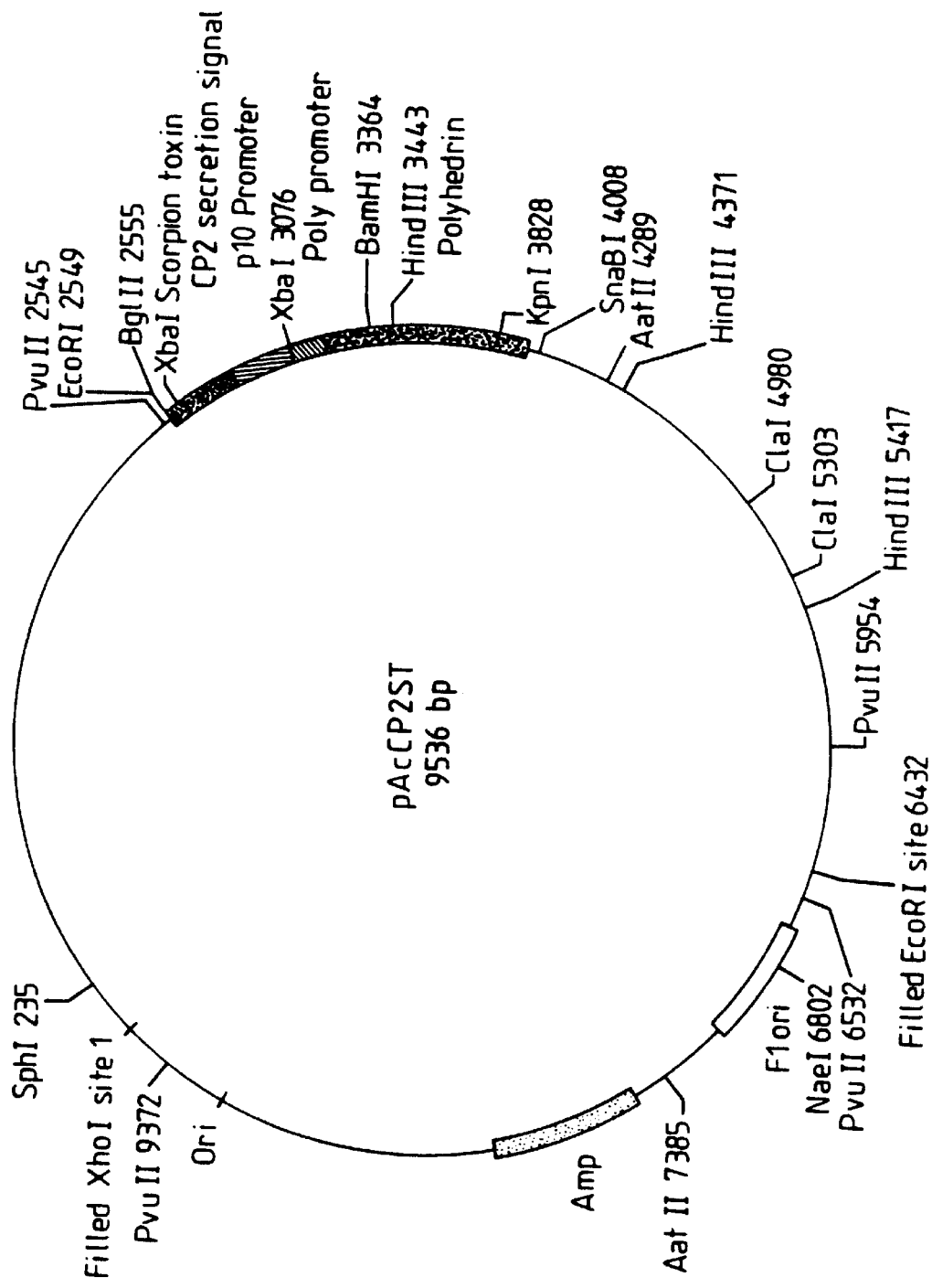

FIG. 12 shows a restriction map of pAcCP2ST and the sequences of the p10 promoter (SEQ. ID NO:38), CP2 signal peptide (SEQ. ID NO:49 and 50) and AaHIT coding region (SEQ. ID NO:41 and 42).

Figure 13:
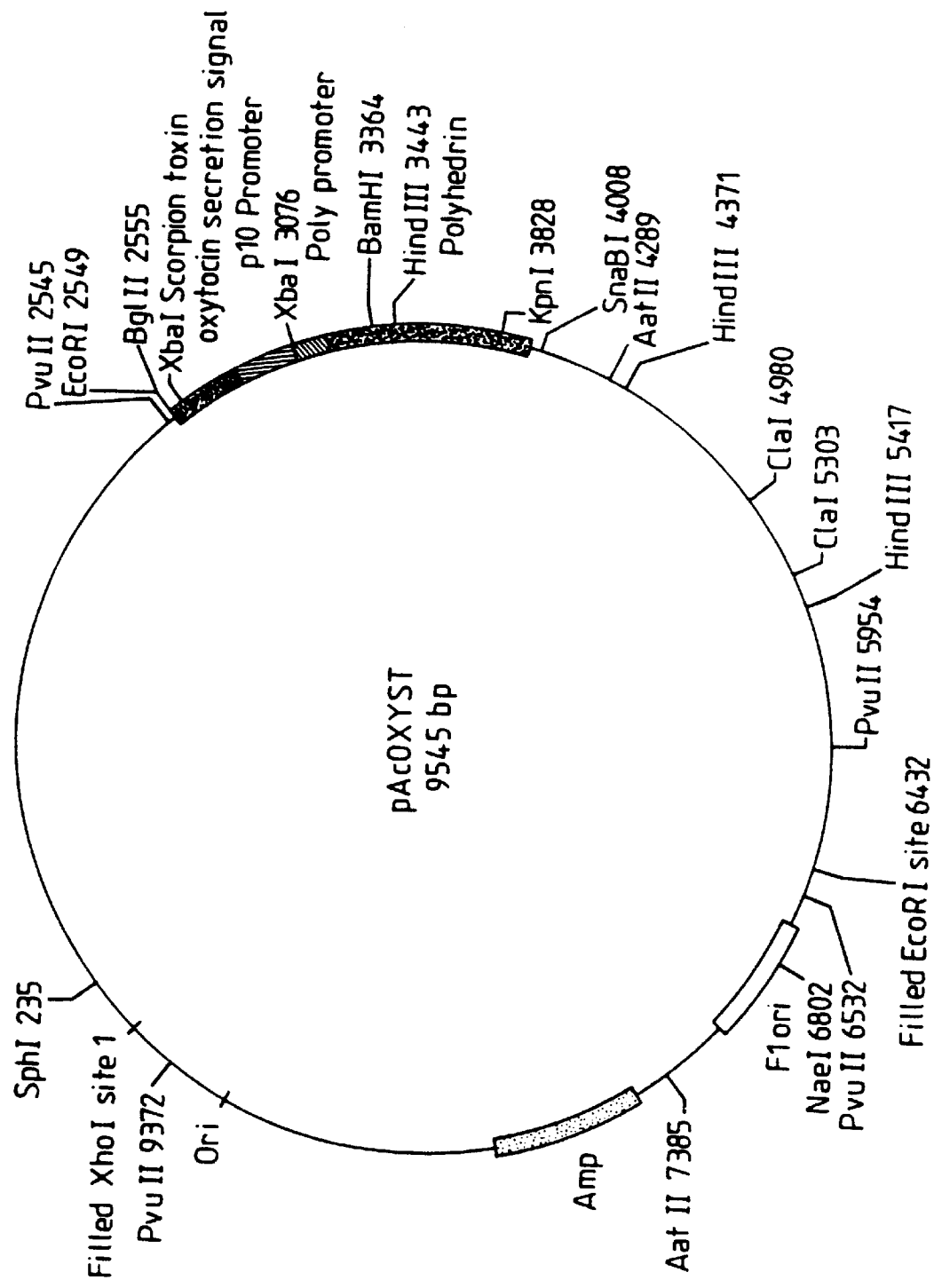

FIG. 13 shows a restriction map of pAcOXYST and the sequences of the p10 promoter (SEQ. ID NO:38), oxytocin signal peptide (SEQ. ID NOS:51 and 52) and AaHIT coding region (SEQ. ID NOS:41 and 42).

Figure 14:
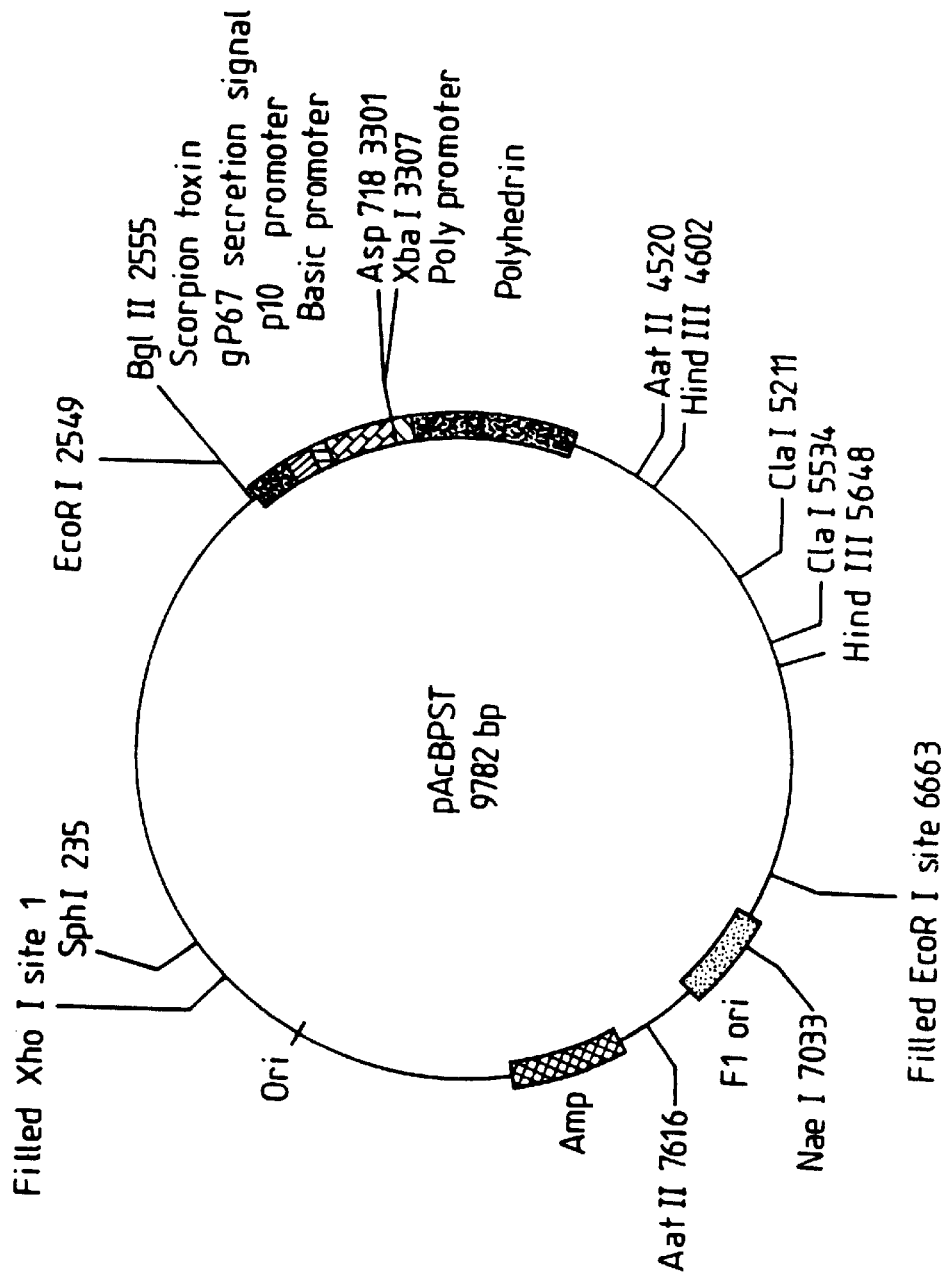

FIG. 14 shows the nucleotide sequence of the AcMNPV basic protein gene promoter and p10 gene promoter (SEQ. ID NO:38) arranged in tandem in association with the gp67 signal peptide coding region (SEQ. ID NO:53) and AaHIT coding region (SEQ. ID NOS:41 and 42). Above the sequence is a plasmid restriction map of the transfer vector (pAcBPST) used to derive the recombinant virus.

Figure 15A:
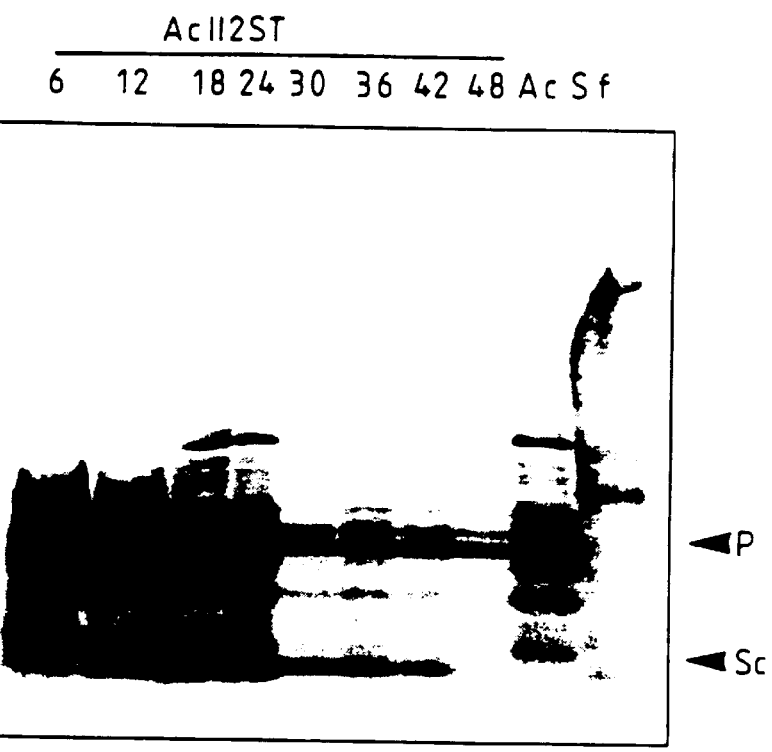
Figure 15B:
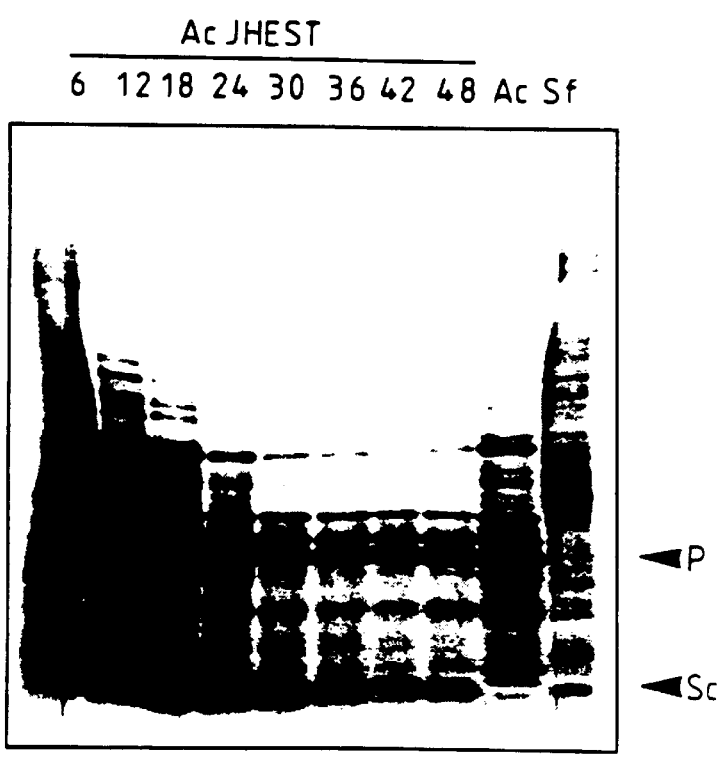

FIG. 15 (Parts A–C) FIG. 15 demonstrates the synthesis of proteins in virus-infected Sf cells as described for FIG. 5 (a) ACI12ST; (b) ACJHEST; (c) AcBPST.

FIG. 16 shows the AcMNPV gp67 signal sequence and SefIT coding sequence (SEQ. ID NO:54). The gp67 signal peptide is underlined with the two potential translation initiation codons in bold type face.

FIG. 17 shows the sequence of the synthetic oligonucleotides used in the construction of the SefIT gene. The nucleotides are shown in the 5'-3' direction (OS 3711) (SEQ. ID NOS:56, 57 and 58) and in the 3'-5' direction (OS 3712) (SEQ. ID NOS:59, 60, 61, and 62). Restriction enzyme sites used for subcloning of the pair of oligonucleotides into plasmids are shown beneath the sequence. The translation initiation codon is underlined and the translation stop codon (TAG) is indicated by an asterix above the second nucleotide. After annealing, the oligonucleotides were inserted within pDH7, between the Sph I and BamH I sites. pDH7 is a derivative of pEMBL19 that has the secretion signal of the ACNPV gp67 between a unique Bgl II site located in lieu of the Hind III site of the polylinker, and Sph I.

FIG. 18 (SEQ. ID NO:63 and 64) shows the nucleotide sequence of the AcMNPV p10 promoter (1–240) in association with the gp67 signal peptide coding region (246–359). The remaining sequence is the coding region for SefIT. The sequence is shown after mutagenesis of the junction between the gp67 region and the SefIT region.

Figure 19:
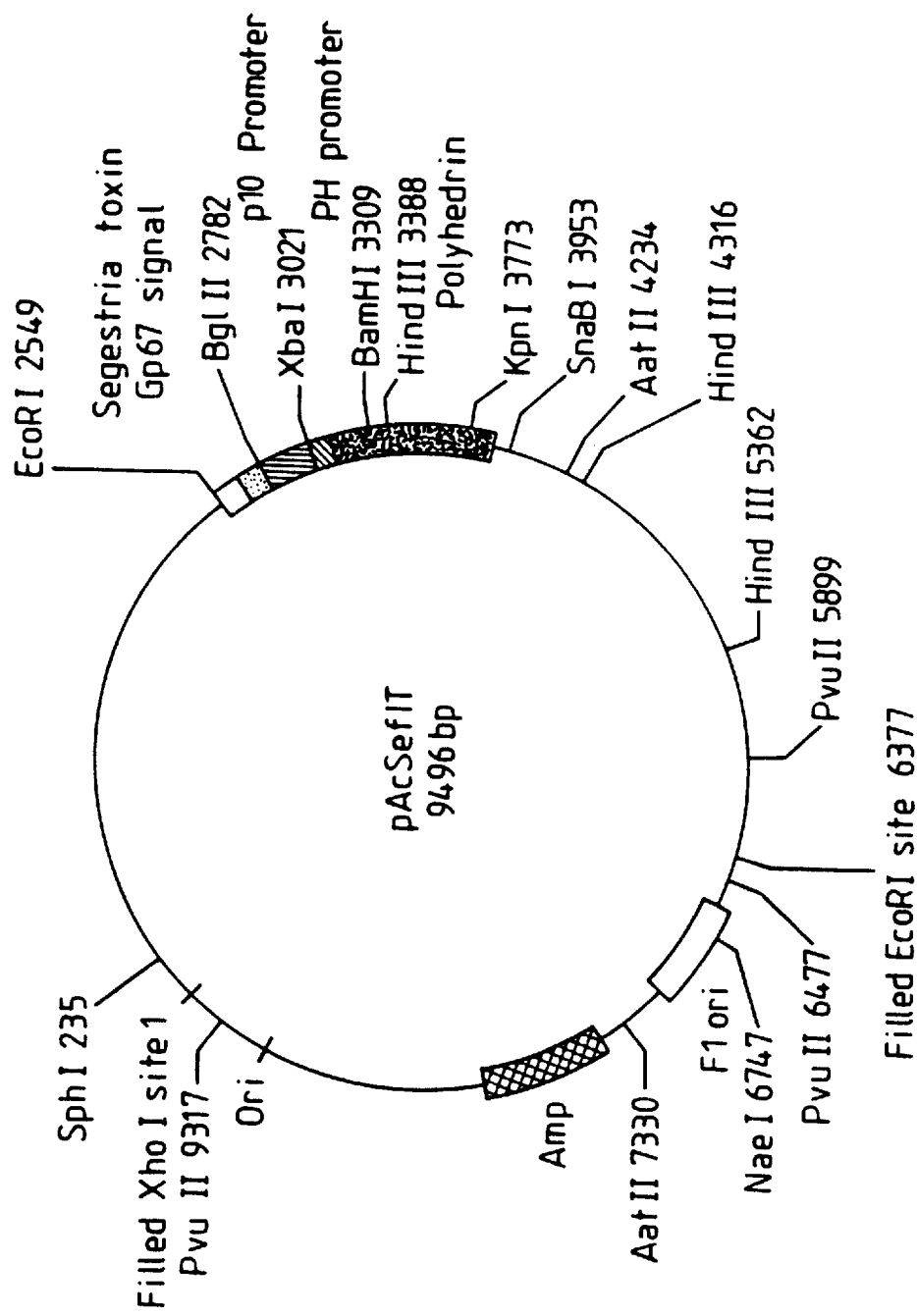

FIG. 19 shows the nucleotide sequence of the AcMNPV p10 gene promoter in association with the gp67 signal peptide coding region (SEQ. ID NO:65) and the SefIT coding region (SEQ. ID NO:66). Above the sequence is a plasmid restriction map of the transfer vector (pAcSefIT) used to derive the recombinant virus.

EXAMPLE

1. Materials and Methods (A) Viruses and cells.

AcMNPV C6 (Possee, 1986) and all recombinant viruses were propagated in *Spodoptera frugiperda* (IPLB-Sf-21) cells (Vaughn et al., 1977) at 28° C. in TC100 supplemented with 5% or 10% foetal calf serum (FCS) in the presence of penicillin and streptomycin. Virus infectivity was estimated using a plaque assay as described by Brown and Faulkner (1977).

Virus purification: Polyhedra were purified from infected cells or insects as described by Harrap et al. (1977), but with the addition of 0.1%(w/v) SDS to all solutions. The SDS was removed by washing the polyhedra with water at the end of purification. Polyhedra were counted using the dry counting method of Wigley (1976)

(B) Construction of synthetic AaHIT and SefIT coding sequences.

The protein sequence of the AaHIT was converted into a nucleotide sequence using the preferred codon bias of the AcMNPV polyhedrin (Hooft van Iddenkinge et al., 1983) and p10 (Kuzio et al., 1984) genes. The predicted DNA sequence was analysed on a VAX mainframe computer using the Staden molecular biology programmes to identify restriction enzyme sites. These were used to design four complementary pairs of synthetic oligonucleotides which were produced on an Applied Biosystem Automated Synthesiser. The sequence was designed so that the four nucleotides before the ATG codon matched those of the AcMNPV polyhedrin gene, thus preserving the integrity of the initiation of translation environs; a translation termination codon was incorporated at the 3' end of the coding region. Appropriate restriction enzyme sites were included to facilitate the insertion of the synthetic oligonucleotides into pUC18 and their subsequent excision as the complete AaHIT coding region with BamHI and Bgl II for later manipulation. The oligonucleotides were assembled into the complete AaHIT coding sequence within pUC18 (Yanisch-Perron et al, 1985) using standard protocols (Sambrook et al., 1989). Further details of this procedure are described above in relation to FIGS. 2, 3a and 3b. The AaHIT coding region in the final plasmid construction, pLS-ST, was sequenced using dideoxynucleotide chain terminators (Sanger et al., 1977) to confirm its authenticity.

In a similar manner, the protein sequence of SefIT was converted into nucleotide sequence information. Two complementary oligonucleotides were synthesized, OS 3711 and OS 3712 (FIG. 17). After annealing, these oligonucleotides were inserted in the plasmid pDH7, between the Sph I and BamH I sites. pDH7 is a derivative of pEMBL19 (Dente et al, 1983) that contains the secretion signal of the AcMNPV gp67 between a unique Bgl II site located in lieu of the Hind III site of the polylinker, and Sph I. The SefIT coding region in the plasmid construction, pDH7-SefIT, was sequenced as described above to confirm its authenticity.

(C) Construction of baculovirus transfer vectors.

Figure 3A:
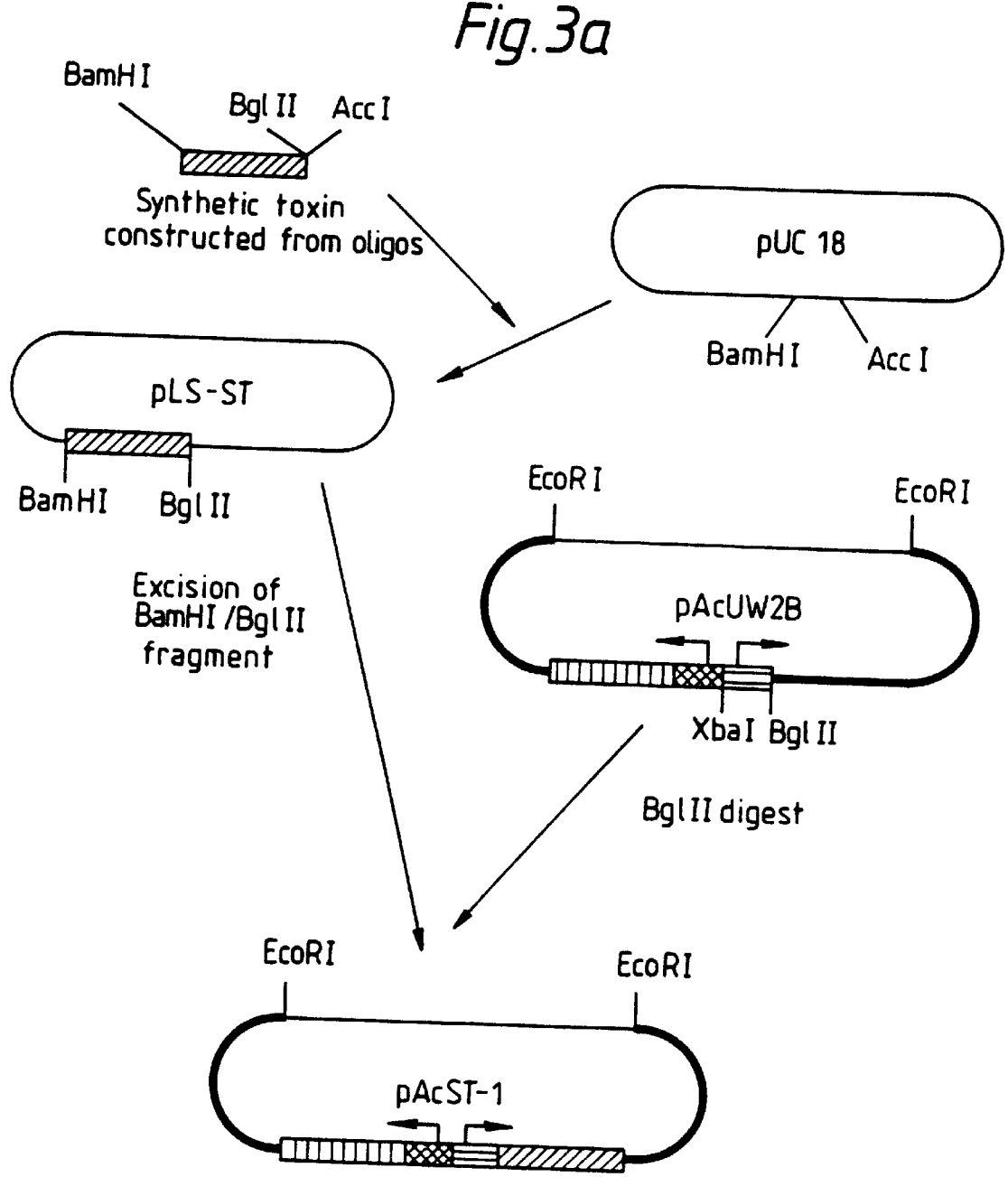
FIG. 3a shows the construction of pAcST-1. The synthetic oligonucleotides encoding the AaHIT were assembled within pUC18 as described in FIG. 2 to derive pLS-ST. The complete AaHIT coding region was then removed from pLS-ST and inserted at the Bgl II site of pAcUW2B, a baculovirus transfer vector containing a copy of the p10 promoter located upstream of the complete AcMNPV polyhedrin gene. The resulting transfer vector pAcST-1, contains the complete AaHIT coding sequence without a signal peptide.

(i) pAcST-1 (comparison): To produce a practical virus insecticide required that the AaHIT coding sequence be inserted into a baculovirus which retained a functional polyhedrin gene. The transfer vector pAcUW2B (Weyer et al. 1990) satisfies this criterion. It is based on the AcMNPV EcoR I-I fragment, which encompasses the polyhedrin gene. It has a complete copy of the polyhedrin gene, a copy of the p10 promoter and a Bgl II cloning site with SV40 transcription termination sequences, inserted at a position 90 nucleotides upstream from the polyhedrin ATG codon and in the opposite orientation. The AaHIT coding region was excised from pLS-ST using BamH I and Bgl II, purified after fractionation in a low gelling temperature agarose gel, and inserted into the Bgl 11 site of the transfer vector pAcUW2B (Weyer et al., 1990) to derive pAcST-1 (FIG. 3a).

Figure 4B:
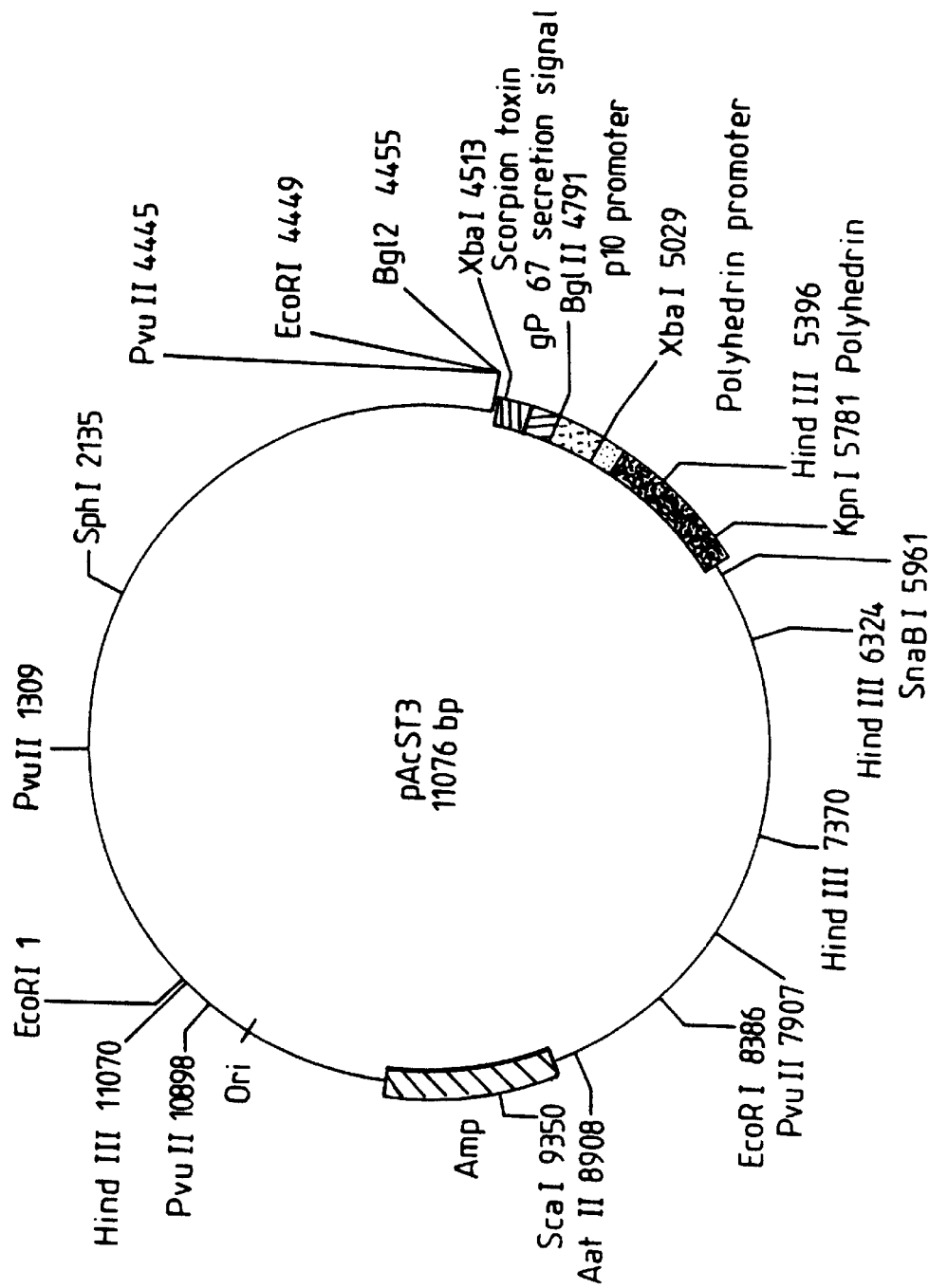
FIG. 4 (Parts A–C).
FIG. 4A shows the nucleotide sequence of the AcMNPV p10 promoter (1–240) in association with the gp67 signal peptide coding region (246–359) and AaHIT coding region (360–569) (SEQ. ID NO:32 and 33). The site of transcription initiation from the p10 promoter (position 167–170; TAAG) is indicated in bold typeface. The junction between the signal peptide and the toxin is shown prior to mutagenesis (SEQ. ID NO:34, 35, and 36). The nucleotides which were removed are shown in lower case (see also SEQ. ID NO:37).
FIG. 4c shows the nucleotide sequence of the AcMNPV p10 gene promoter (SEQ. ID NO:38) in association with the gp67 signal peptide coding region (SEQ. ID NOS:39 and 40) and AaHIT coding region (SEQ. ID NOS:41 and 42). A plasmid restriction map of the transfer vector (pAcST3) (FIG. 4B) is used to derive the recombinant virus.

(ii). pAcST-2: To produce a virus which potentially could secrete the AaHIT the coding region was inserted into pAcATM1, a transfer vector with a copy of the gp67 signal peptide sequence (Whitford et al., 1989) after the polyhedrin promoter. The toxin coding region was excised from pLS-ST with BamH I and Bgl II and inserted into the BamHI site in pAcATM1, producing the transfer vector pAcST-2 (FIG. 3b). pAcATM1 is a derivative of pAcCL29 (Livingstone and Jones 1989), a polyhedrin promoter-based transfer vector containing the M13 intergenic region which facilitates production of single stranded DNA via the use of an M13 helper phage (Livingstone and Jones 1989). The junction between the gp67 signal sequence and the AaHIT was modified using M13 oligonucleotide directed mutagenesis (Kunkel, 1985) using GP67-SC.Tox shown in FIG. 4A to derive the appropriate DNA sequence encoding a favourable protease recognition site; this step also removed the original ATG translation initiation codon of the AaHIT. The changes made to the gp67 junction are shown in FIG. 4A, together with the sequence of the p10 promoter.

(iii). pAcST-3 (invention): The gp67 signal sequence and the AaHIT were removed from pAcST-2 by Xho II digestion and placed into the Bgl II site in pAcUW2B to produce pAcST-3 (FIG. 3b).

Figure 9:
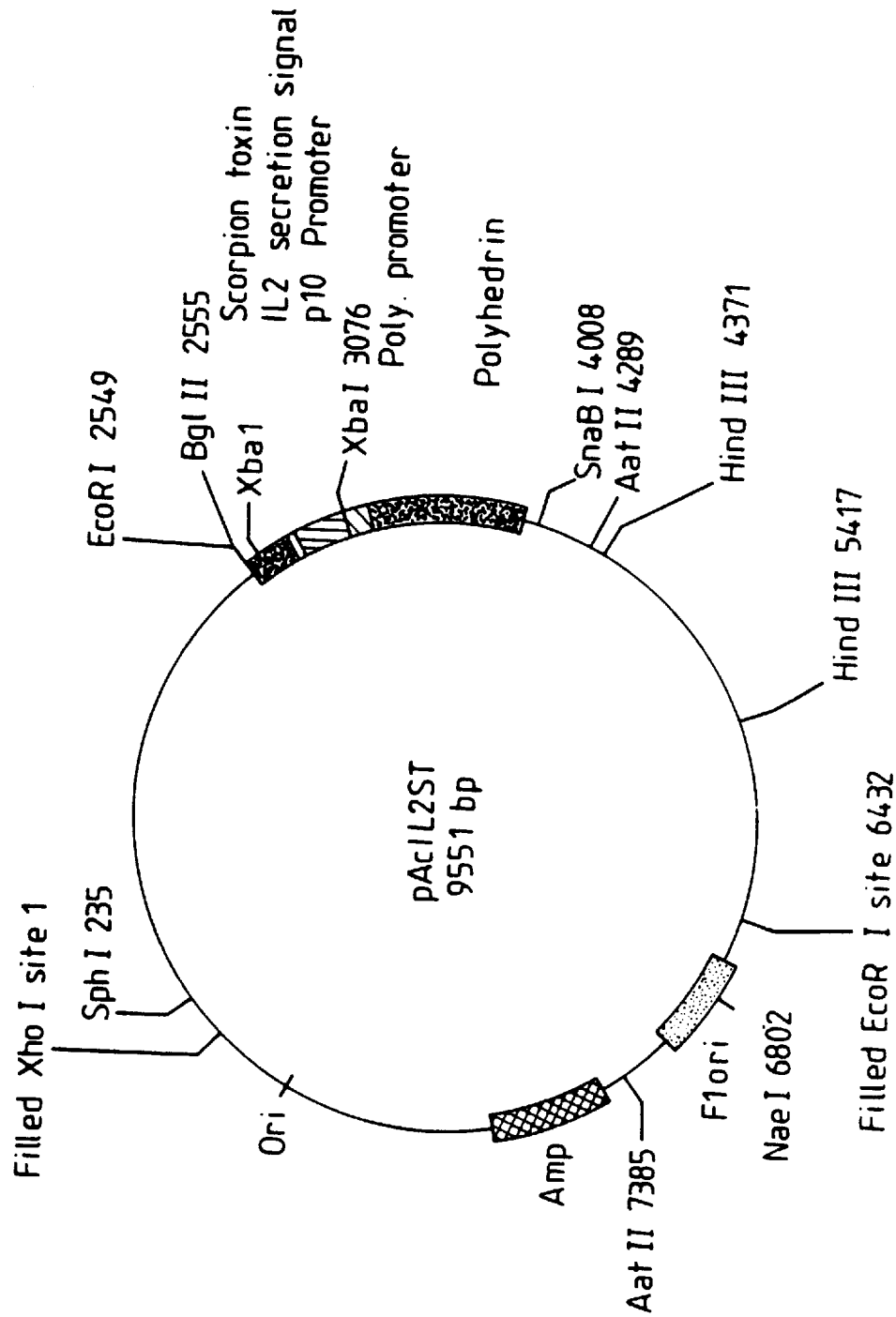
FIG. 9 shows the nucleotide sequence of the AcMNPV p10 gene promoter (SEQ. ID NO:38) in association with the interleukin 2 signal peptide coding region (SEQ. ID NOS:43 and 44) and AaHIT coding region (SEQ. ID NOS:41 and 42). Above the sequence is a plasmid restriction map of the transfer vector (pAcI12ST) used to derive the recombinant virus.

(iv). pAcI12ST (invention). The AaHIT synthetic coding region was inserted as a BamH I/Bgl II-digested DNA fragment into the BamH I site within the polylinker region of the BLUESCRIPT M13 phagemid (Stratagene). The orientation of the coding region was confirmed by restriction enzyme mapping. The IL-2 signal peptide coding sequences (Taniguchi et al, 1983) were inerted between the EcoR V/Pst I sites upstream of the translation initiation codon of the toxin sequences. The junction between the signal peptide and toxin coding sequences was altered using oligonucleotide-directed mutagenesis (Kunkel, 1985) to provide an optimal protease recognition site for cleavage of the secretory peptide. The sequence was confirmed using chain termination methods. The DNA fragment containing the signal peptide and toxin coding regions was excised with Xho II and inserted at the Bgl II site of the baculovirus transfer vector pAcUW21, to derive pAcI12ST. pAcUW21 is a development from pAcUW2B and has reduced virus sequences flanking the polyhedrin gene and p10 gene promoter; it also has the appropriate regulatory sequences to enable single stranded DNA production in bacteria, after super-infection with M13 KO7, pAcUW21 was constructed by excising a 5408 nucleotide DNA fragment from pAcUW2B and inserting this into pEMBL19 which had been digested with Hind III and EcoR I, the ends of the DNA repaired with DNA polymerase, treated with calf intestinal phosphatase prior to ligation. The sequence of the I1-2 signal peptide coding region in association with the AaHIT coding sequence is shown in FIG. 9.

(v). pAcJHEST (invention): A synthetic DNA encoding the JHE signal peptide was constructed by inserting two pairs of overlapping oligonucleotides into the polylinker of a modified version of pEMBL19 (the Hind III site had been altered to a Bgl II) between the Bgl II and EcoR I sites. This plasmid was then digested with BamH I (within the 3' region of the JHE sequences) and the toxin coding region inserted as a BamHI/Bgl II-digested DNA fragment. The junction between the JHE signal peptide and toxin coding regions was altered using oligonucleotide-directed mutagenesis as described above. The sequences were then recovered by Bgl II digestion and inserted within pAcUW21 at the Bgl II site to derive pAcJHEST. The sequence of the JHE signal peptide coding region in association with the AaHIT coding sequence is shown in FIG. 10.

(vi). pAcSTST (invention): The polymerase chain reaction method was used to make a copy of the AaHIT gene with the signal peptide sequence for the natural AaHIT (Bougis, P. E., et al., 1989) at the 5' and and Bgl II sites at both ends. The 5' primer was (SEQ. ID NOS:67 and 68):

```
                 Met Lys Phe Leu Leu Leu Phe Leu Val Val Leu
TATATAAGATCT ATG AAA TTT CTC CTA TTG TTT CTC GTA GTC CTT
Pro Ile Met Gly Val Leu Gly
CCA ATA ATG GGG GTG CTT GGC AAA AAA AAC GGC TAC GCG GTT GAC
TC
```

The 3' primer was: (SEQ. ID NO:69) TATATAAGATCT TTA GTT AAT AAT AGT AGT GTC

The Bgl II digested fragment was then inserted into pAcUW21 at the unique Bgl II site. The vector was designated pAcSTST. The sequence of the AaHIT signal peptide and AaHIT coding region is shown in FIG. 11.

(vii). pAcCP2ST (invention): This vector was prepared as for pAcSTST except that the signal peptide sequence for CP2 from *Drosophila melongaster* (Syder, M. et al., 1982) was added instead of the natural AaHIT signal peptide. The 5' primer was: (SEQ. ID NOS:70 and 71)

```
                 Met Ala Cys Pro Ser Leu Ala Cys Cys Leu Leu
TATATAAGATCT ATG GCC TGC CCC AGT CTC GCT TGC TGC CTG CTT
Gly Leu Leu Ala Leu THr Ser Ala
GGC CTA CTG GCT CTG ACC TCC GCC AAA AAA AAC GGC TAC GCG GTT
GAC TC
```

The 3' primer was: (SEQ. ID NO:69) TATATAAGATCT TTA GTT AAT AAT AGT AGT GTC. The sequence of CP2 signal peptide and AaHIT coding region is shown in FIG. 12.

(viii). pAcOXYST (invention): This vector was prepared as for pAcSTST except that the signal peptide sequence for oxytocin from rat (Ivell, R. and Tichter, D., 1984) was added instead of the natural AaHIT signal peptide. The 5' primer was: (SEQ. ID NO:72 and 73)

```
                    Met Phe Lys Phe Val Mey Ile Leu Ala Val Val
TATATAAGATCT ATG TTT AAA TTC GTT ATG ATT CTA GCG GTT GTT
Gly Val Ala Thr Ala
GGC GTT GCC ACA GCG AAA AAA AAC GGC TAC GCG GTT GAC TC.
```

The 3' primer was: (SEQ. ID NO:69) TATATAAGATCT TTA GTT AAT AAT AGT AGT GTC. The sequence of oxytocin signal peptide and AaHIT coding region is shown in FIG. 13 (SEQ. ID. NO:51 and 52).

(ix). pAcUW21BP (invention): The basic protein gene promoter was excised from pAcMP1 (Hill-Perkins et al, 1990) with Asp 718 and BamH I and inserted between the same sites in pDH7 to derive pDH7BP. The polymerase chain reaction method was then used to make a copy of the basic protein gene promoter and also add an Xba I site at the 5' end of the promoter fragment. This fragment was then inserted in lieu of the p10 gene promoter within pAcUW21 and designated pAcUW21BP. The DNA sequence containing the gp67 signal peptide and toxin coding regions was excised from pAcST-3 using Xho II and inserted at the Bgl II site of pAcUW21BP to derive pAcBPST. The sequences of the basic protein and p10 gene promoters in association with the gp67 and AaHIT coding regions are shown in FIG. 14.

(x). pAcSefIT (invention): The gp67 coding region was put in frame with the SefIT coding region (in pDH7-SefIT) using site directed mutagenesis as described above. The alteration was verified by sequencing. The complete coding region (gp67 and SefIT) was excised from pDH7-SefIT with Bgl II and BamHI and inserted at the Bgl II site of pAcUW21 to derive pAcSefIT. The sequence of the SefIT coding region in association with the gp67 signal peptide region and p10 gene promoter is shown in FIGS. 18 and 19.

(D) Production of recombinant viruses.

(i). AcST-1 (comparision): *Spodoptera frugiperda* cells were co-transfected with pAcST-1 and polyhedrin negative AcRP6-SC (Kitts et al 1990) infectious virus DNA using the calcium phosphate procedure (Smith et al., 1983). Recombinant viruses were selected as a polyhedrin-positive phenotype in a standard plaque assay.

(ii) AcST-3 (invention): pAcST-3 was co-transfected with AcRP6-SC using the lipofectin method (Felgner et al, 1987; Groebe et al, 1990) and viruses were screened as for the previous co-transfection.

(iii) AcI12ST, AcJHEST, ACBPST, AcSTST, AcCP2ST, ACOXYST, AcSefIT (all invention): as described for AcST-3.

Recombinant viruses were purified by five sequential plaque assays and authenticated by Southern hybridisation of EcoR I digests of DNA from infected cells using a [$^{32}$P] radiolabelled oligonucleotide, specific for the AaHIT gene, as a probe.

(E) Analysis of proteins in virus-infected cells

*S. frugiperda* cells ($10^6$ per 35 mm dish) were inoculated with virus at a multiplicity of infection (moi) of 10 pfu per cell and incubated at room temperature for 1 hour. The inoculum was removed and replaced with 2 mls of TC100/ 10% FCS and the dishes were incubated at 28° C. until 15 minutes prior to the time of radiolabelling. The media was then removed, 0.5 mls of starvation medium (cysteine-free TC100 with 2% dialysed FCS) added and the plates incubated at 28° C. for 15 mins. After this, 0.5 mls of starvation medium supplemented with 20 µCi [$^{35}$S] cysteine was added and incubated for 1 hour. Protein extracts were separated in denaturing 10–30% polyacrylamide gradient gels (Cook et al., 1979). The gels were then stained with Coomassie blue, dried and exposed to X-ray film.

(F) Immunoblot analysis of infected cell proteins or HPLC fractions

Protein extracts from unlabelled, virus-infected cells (see E above, or G below) were separated in 10–30% denaturing polyacrylamide gels, and transferred to nitrocellulose filters using a Bio-Rad electroblot apparatus for two hours at 100V in 25 mM-Tris, 5.3M-glycine and 20% methanol as transfer buffer. The filter was incubated in PBS containing 0.05% Tween-20 (PBST) with 3–5% low fat milk powder as a blocking agent. This was gently shaken for 1 hour at room temperature, then incubated for a further 2 hours with guinea-pig serum raised against a synthetic AaHIT peptide diluted 1/1000 in PBST (titre greater than 1:10,000 in an indirect ELISA against homologous peptide). The filter was then washed several times in PBST to remove unbound antibody. Bound antibody was detected using anti-guinea-pig IgG-alkaline phosphatase conjugate.

(G) HPLC of AaH total toxin and infected cellular supernatants and in vivo assay in *Musca domestica:* test for toxicity by injection Total crude AaH venom obtained from Sigma as a freeze dried sample (1 mg), was resuspended in 20 µl of DMSO then diluted to 100 µl in H$_2$O. Precipitated material was removed by centrifugation at 15,000 g for 5 minutes. Purification of supernatant (20 µl) was carried out by HPLC using an LCD system with a Spectroflow 783 detector set at 280 nm. A Spherisorb, $C_8$, 5 $\mu$m particle size, 25 cm column was used for separation. Solvent A was 0.15M ammonium formate. pH 2.7 and solvent B was acetonitrile. A linear gradient was run from 15% to 40% B in A over 40 minutes at a flow rate of 1 ml/minute and 40×1 ml fractions were collected. The fractions were freeze dried to remove acetonitrile and ammonium formate, then were resuspended in 200 $\mu$l of 0.1 mg/ml BSA in water. 0.5 $\mu$l of each of the fractions were injected into 10 adult *M. domestica* (male and female) using a 25 gauge syringe needle.

Analysis of supernatants from infected cells was carried out using the supernatant from 2 dishes of infected *S. frugiperda* cells as starting material (ie 2mls). This was concentrated 4× using the Centricon filtration system (3K) by centrifugation at 5000 × g for three hours on a Sorvall RC5 centrifuge. 100 $\mu$l of the concentrated material was loaded onto the HPLC column and treated in the same way as the total venom. After the sample had been run on the HPLC the fractions were freeze dried and resuspended in 100 $\mu$l of 0.1 mg/ml BSA. 4 $\mu$l of each fraction was used to inject *M.domestica.*

(H) Preparation of viruses in insects

*T. ni* were maintained in the laboratory on a semi-synthetic diet (Hunter et al., 1984). All assays were carried out using polyhedra which has been passaged once through insects. For the initial passage, third instar *T. ni* larvae consumed diet plugs which contained a crude extract of infected cells, after which the larvae were transferred onto fresh diet. Immediately after death insects were harvested and pooled. Polyhedra were purified and these were used for all other assays.

(I) Biological activity of haemolymph recovered from infected larvae

The biological activity of the toxin was assessed by the injection of 4 $\mu$l of serial dilutions of a given sample into the dorso lateral area of the abdomen of *M. domestica,* between sclerites. Fractions containing the toxin obtained from HPLC of AaH total venom were used to construct standards in order to estimate the amount of toxin recovered from the haemolymph. The fractions were freeze dried and resuspended to a concentration of 90 ng/100 µl water. This was further diluted in PBS to facilitate the injection of 4 µl containing 18, 9, 4.5, 2.25 or 1.125 ng of toxin into the insect (18 ng was shown to be in excess of the LD50 for the toxin).

(J) LD50 measurements 50 second instar larvae of T.ni (approx. 0.6–0.7 mg) were individually fed five serial dilutions of a known titre of virus on a small plug of artificial diet in a microtitre plate. The maximum dose of the virus should ideally give over 90% mortality, and the minimum dose should give 10% mortality. Non-engineered strains of AcMNPV fulfilled these conditions with 120, 60, 30, 15 and 7.5 PIB's per larvae. The larvae consumed the dose within 24 hours and those which did not were excluded from the assay. The others were transferred to individual containers of artificial diet and were kept at 24 hours in a dark incubator. Larvae were examined daily and cadavers were removed, smeared on a slide and the cause of death confirmed after staining and microscopic examination. The data obtained were analysed using probit analysis to determine the LD50 values (Finney, 1971).

(K) ST50 measurements,

To produce the neonate larvae which were used in these studies, adults were reared in cages containing filter papers for oviposition. The filters carrying the eggs were surface sterilised and retained in plastic containers. After hatching, the neonates were starved for 3–6 hours prior to droplet feeding with the various virus suspensions. The suspensions were coloured with 5% blue food dye to enable visualisation of feeding. Small droplets of this suspension were placed on a petri dish in concentric rings. The larvae were introduced to the centre of these concentric rings after which they moved through the droplets taking in a small volume of liquid before crawling on to the lid of the dish. Larvae which were damaged in handling remained in the centre allowing synchronous feeding and the selection of healthy individuals. Previous work has shown that in these type of experiments, larvae of *T. ni* consume 0.0087 (+/−0.0023) µl. (Hughes and Wood, 1981. Hughes et al. 1986) and in these ST50 assays the virus suspensions contain $2\times10^6$ polyhedra/ml. After feeding, the larvae were maintained in individual containers with artificial diet. After 24 hours, the larvae were checked and any deceased individuals removed since these deaths were due to handling. After a further 48 hours the larvae were checked once again and thereafter at frequent intervals. All dead larvae were removed and the cause of death assessed by appearance and microscopic examination. ST50 calculations were carried out using the Vistat programme (Boyce Thompson Institute, Ithaca, N.Y.).

(L) Reduction in feeding damage by insects infected with AcST-3

Third instar larvae (*T. ni*) were fed individually overnight with a plug of artificial diet inoculated with $10^4$ polyhedral inclusion bodies (PIB's). This high dose ensured 100% mortality. After feeding, the larvae were enclosed in groups of 5, with cabbage leaves from plants which had been grown in a controlled environment. Prior to feeding the leaves had been soaked overnight to ensure water saturation. After two days of feeding, leaf damage was assessed photographically.

2. Results (A) Synthesis of proteins by recombinant viruses

The AaHIT has a protein sequence comprising 70 amino acids (including the first methionine), with a predicted molecular weight of 8000. Analysis of extracts from *S. frugiperda* cells, infected with AcST-1 (AaHIT without secretory signal) or AcST-3 (AaHIT with a secretory signal), in a denaturing 10–30% polyacrylamide gel failed to detect an additional protein of the expected size either by Coomassie blue or silver staining. Virus-infected cells were then radiolabelled with [$^{35}$S] cysteine at various times after infection (FIG. 5). These results showed an additional protein which migrated just below the expected position of the virus p10 protein (the p10 protein lacks cysteine residues). Synthesis of this putative AaHIT was maximal between 18 and 36 hours post-infection. The identity of the protein was confirmed by using Western blot analysis of AcST-1 or AcST-3 infected cell extracts with an antiserum raised to a synthetic AHaIT.

(B) HPLC of AaH total venom and synthetic AaHIT

Figure 6:
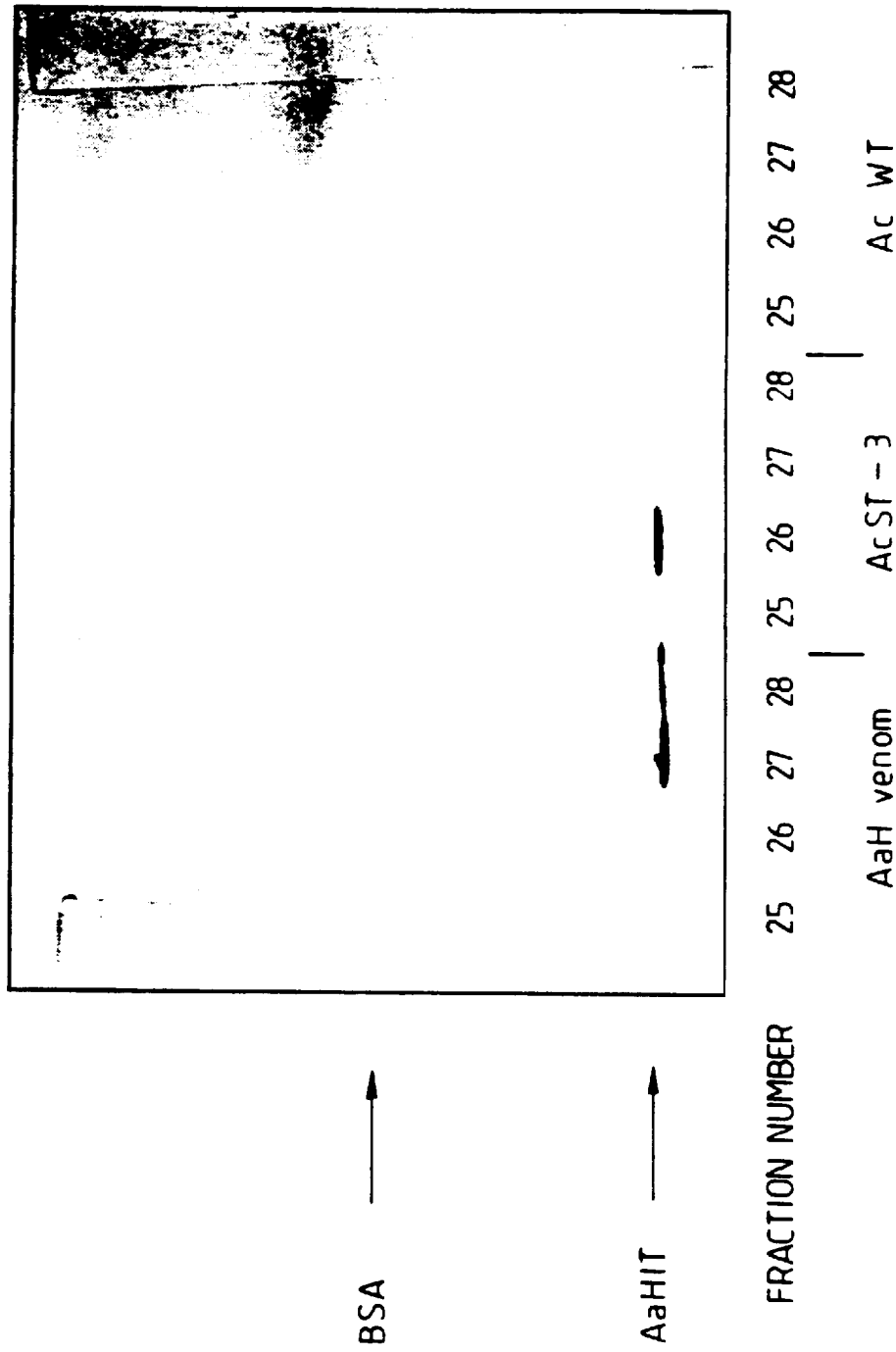
FIG. 6 shows the results of immunoblot analysis of HPLC fraction of AaH total toxin and AcST-3 infected cell medium. Fractions 25–28 from HPLC were separated on a 10–30% polyacrylamide gradient gel and were blotted as described in the text. BSA (present in resuspension buffer) and AaHIT are indicated.

The HPLC traces revealed a peak in the optical density readings at 280 nm around fraction 27/28 which was present in the total venom and the medium of cells infected with AcST-3 but was absent in cells infected with the wild type virus. Western blot analysis of the fractions between 25 and 28 indicate the presence of the AaHIT in fractions 27 and 28 of the crude venom and in 26 and 27 of the supernatants of cells infected with AcST-3 (FIG. 6).

Figure 7:
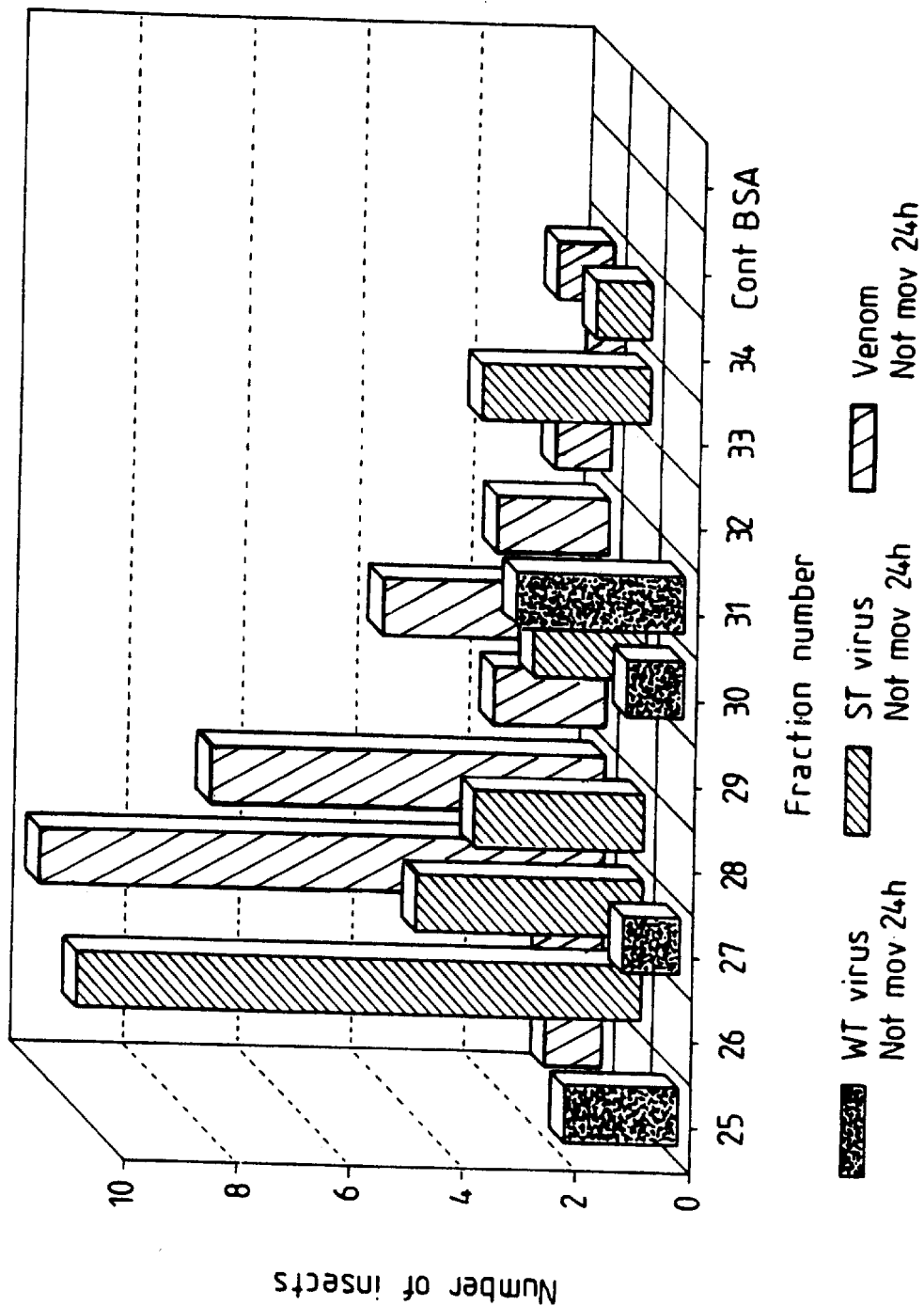
FIG. 7. Total crude AaH venom or the medium from Sf cells infected with AcST-3 were fractionated using HPLC (see Example 1). Analysis of selected fractions was performed by injection of 4 μl into *M. domestica* and observing for paralysis and death.

Injection of *M. domestica* with small volumes of each of these fractions confirmed that the paralytic and lethal activity is found in these fractions. Immobility due to the toxin was evident at 1 hour after injection and deaths were evident at 24 hours post injection (FIG. 7).

(C) Biological activity of haemolymph recovered from infected larvae.

Secretion of the AaHIT from AcST-3-infected cells in vivo was assessed by recovering haemolymph from virus-infected *T. ni* larvae and injecting it into *M. domestica*. 4th instar larvae *T. ni* were infected with $10^5$ PIB's of AcST-3. At 72 hours post infection an incision was made above the terminal proleg and haemolymph was collected (20 µl). To limit melanisation, the pipette used to collect all samples of haemolymph was rinsed in a solution of phenylthiourea. 4 µl of this haemolymph was used to inject test larvae of *M. domestica* and toxicity was assessed. The response was compared with a standard curve prepared using HPLC-purified AaHIT total vemon and the results are shown in Table 2. The response of the *M. domestica* indicated a concentration of toxin within the *T. ni* larvae of around 1.5–2.0 ng/µl of haemolymph at 72 hours post injection.

TABLE 2

Toxic activity of Haemolymph recovered from larvae infected with AcST-3 (72 hours p.i.)

| Dose (ng) | | A | B | C | D |
|---|---|---|---|---|---|
| control (PBS) | | 10 | 0 | 0 | 10 |
| 1.125 | | 7 | 2 | 1 | 10 |
| 2.25 | Dilutions | 2 | 5 | 3 | 10 |
| 4.5 | of | 0 | 4 | 6 | 10 |
| 9.0 | AaHIT | 0 | 4 | 6 | 10 |
| 18.0 | | 0 | 0 | 10 | 10 |
| Haemolymph | AcNPV | 10 | 0 | 0 | 10 |
| Haemolymph | AcST-3 | 0 | 3 | 7 | 10 |

A = Insects capable of flight
B = Insects capable of movement but not flight
C = Insects incapable of any movement
D = Number of insects injected (D) In vivo activity of the recombinant viruses The in vivo activities of the recombinant viruses were assessed by estimation of LD50 values. *T. ni* second instar larvae were infected. Replicate individuals were fed doses of 7, 15, 30, 60 or 120 PIB'S. Following probit analysis, the LD50 values of the unmodified AcMNPV was 44 (95% confidence limits of 35 and 55), AcST-1 was 38 (95% confidence limits of 31 and 46) and for AcST-3 (invention) was 31 (95% confidence limits of 27 and 37). The LD50 values for ACMNPV and AcST-3 are significantly different at α=0.05. The difference in LD50 is relatively small, the increase being 1.4191 with 95% confidence limits of 1.026216–1.9846.

ST50 was assessed after infection of neonates. The ST50 data, however, demonstrated a highly significant decrease in the time taken to kill the larvae. The ST50 for AcMNPV was 113.1 (95% confidence limits of 112–115), AcST-1 was 109.2 (95% confidence limits of 107–110) and for AcST-3 (invention) was 85.8 hours (95% confidence limits of 85–87 hours). The AcST-3 result was significantly different from that of the unmodified virus or AcST1, which contains the toxin coding sequence without a secretory signal (α=0.0001). This means that the AcST-3 virus kills the *T. ni* larvae at least 25% faster than the AcMNPV. These results are summarised in Table 3:

TABLE 3

LD50 and ST50 values for AcST-1, AcST-3 and AcMNPV

| VIRUS   | LD50 (95% CL) | ST50 (95% CL)    |
|---------|---------------|------------------|
| AcMNPV  | 44 (35–55)    | 113.1 (112–115)  |
| AcST-1  | 38 (31–46)    | 109.2 (107–110)  |
| AcST-3  | 31 (27–37)*   | 85.8 (85–87)**   |

*This represents a statistically significant reduction in LD50 relative to the wild-type virus (α = 0.05).
**This represents a statistically significant reduction in LT50 relative to the wild-type virus (α = 0.0001).

(E) Pathology of infection.

The pathology after infection with AcMNPV, AcST-1 or AcST-3 was also examined. The larvae infected with AcST-3 differed from that of those infected with AcST-1 or AcMNPV. Infection with AcST-1 or AcMNPV resulted in massive viral induced tissue damage leading to liquifaction of the larvae producing a creamy colouration. On infection with AcST-3, the larvae maintained their structural integrity and remained a green colour.

(F) Reduction in feeding damage by insects infected with AcST-3

Figure 8:
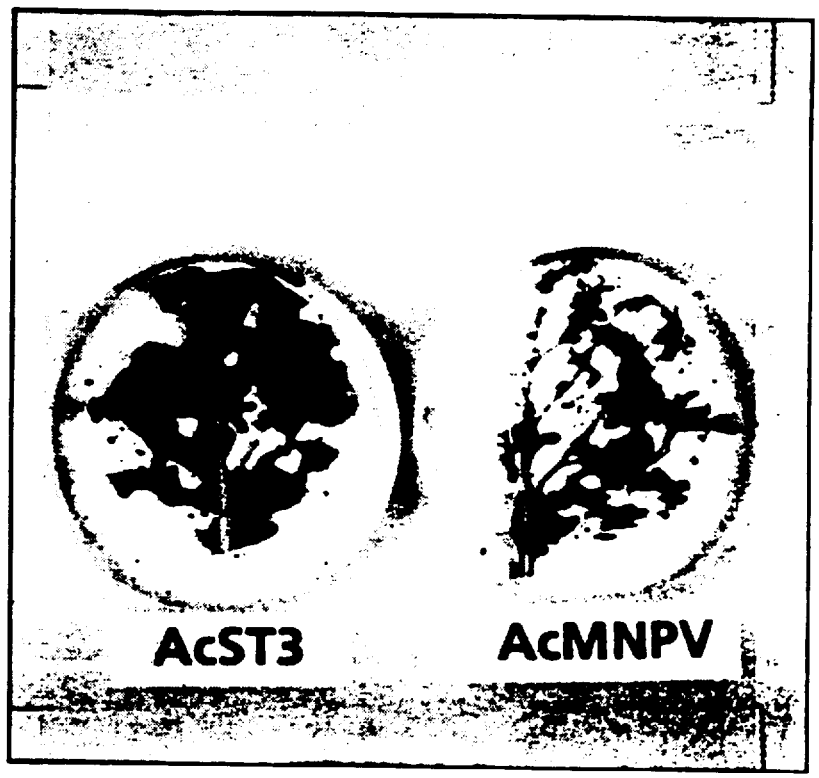
FIG. 8 shows topical leaf damage by larvae infected with AcST-3 and AcMNPV (wild type).

The effectiveness of the AcST-3 recombinant virus in reducing feeding damage of crop plants by *T. ni* larvae is shown in FIG. 8.

(G) Synthesis of proteins by recombinant viruses with alternative signal peptides.

The expression of the toxin gene inserted into each of the recombinant viruses was tested by infecting *Spodoptera frugiperda* cells and radiolabelling individual culture dishes at regular time intervals for 1 hour. The results are shown in FIG. 15*a, b*. AcJHEST produced some toxin at 12 hours post-infection, with a peak synthesis between 18–36 hours post-infection; thereafter, the rate of protein production decreased. Comparable results were observed in AcI12ST-infected cells, although the yield of the toxin in cells infected with this virus may have been slightly lower.

(H) Synthesis of proteins by a recombinant virus with a hybrid gene promoter

Figure 15C:
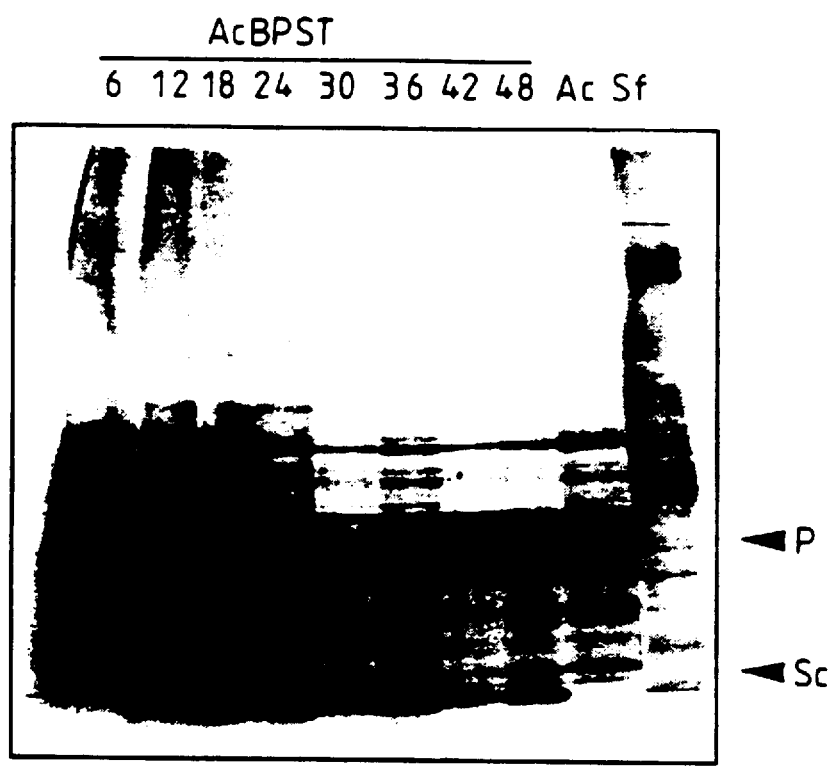

FIG. 15*c* also shows the kinetics of scorpion toxin production in AcBPST-infected cells. It is evident that this virus initiates toxin production in considerable amounts by 12 hours post-infection. The yield is significantly higher than in any of the other cells infected with recombinant viruses having the toxin gene under the control of the p10 gene promoter alone. Toxin production in AcBPST-infected cells continued until 48 hours post-infection.

(I) Biological activity of toxin secreted into the medium from virus-infected cells.

Table 4 shows the biological activity of the AaHIT secreted into the culture medium supporting the growth of virus-infected Sf cells. The medium was assayed using *M. domestica* as described in (C). It is clear that AcST-1 does not release active toxin into the medium.

(J) In vivo activity of the recombinant viruses with alternative secretion signals or a hybrid gene promoter.

The LD50 values for each recombinant virus were estimated as described previously (D). These were found to be very similar. ST50 was assessed after infection of neonates. The ST50 for AcST-3 was 71.4 hours (95% confidence limits of 70.6–72.2), AcJHEST was 77.7 hours (95% confidence limits of 76.7–78.7), AcI12ST was 87.2 hours (95% confidence limits of 86.1–88.3), AcBPST was 73.1 hours (95% confidence limits of 71.8–74.4).

TABLE 4

Toxic activity of medium from cell cultures infected with recombinant viruses containing AaHIT

| | Hours post-infection | | | | | | | | | | | | | | | | | | | |
|---|---|---|---|---|---|---|---|---|---|---|---|---|---|---|---|---|---|---|---|---|
| | 12 | | | | 18 | | | | 24 | | | | 42 | | | | 48 | | | |
| VIRUS | A | B | C | D | A | B | C | D | A | B | C | D | A | B | C | D | A | B | C | D |
| AcST-1  | 10 | 0 | 0 | 10 | 10 | 0 | 0 | 10 | 10 | 0 | 0 | 10 | 10 | 0 | 0 | 10 | 1 | 0 | 0 | 10 |
| AcST-3  | 10 | 0 | 0 | 10 | 8  | 2 | 0 | 10 | 1  | 5 | 4 | 10 | 0  | 4 | 6 | 10 | 1 | 9 | 0 | 10 |
| AcI12ST | 10 | 0 | 0 | 10 | 9  | 1 | 0 | 10 | 10 | 0 | 0 | 10 | 10 | 0 | 0 | 10 | 8 | 2 | 0 | 10 |
| AcJHEST | 10 | 0 | 0 | 10 | 10 | 0 | 0 | 10 | 7  | 3 | 0 | 10 | 4  | 6 | 0 | 10 | 3 | 7 | 0 | 10 |
| AcBPST  | 10 | 0 | 0 | 10 | 0  | 6 | 4 | 10 | 1  | 4 | 5 | 10 | 0  | 1 | 9 | 10 | 0 | 9 | 1 | 10 |

A = Insect capable of flight
B = Insects capable of movement but not flight
C = Insects incapable of any movement
D = Number of insects injected

TABLE 5

LD50 and ST50 values for recombinant baculoviruses containing AaHIT

| Virus   | LD50 (95% CL) | ST50 (95% CL)     |
|---------|---------------|-------------------|
| AcST-3  | —             | 71.4 (70.6–72.2)  |
| AcJHEST | 46 (36–59)    | 77.7 (76.7–78.7)  |
| AcI12ST | —             | 87.2 (86.1–88.3)  |
| AcBPST  | 50 (36–67)    | 73.1 (71.8–74.4)  |
| AcMNPV  | 41 (34–49)    | 108 (106.9–109.1) |

*E. coli* XL-Blue harbouring pAcATM-1, *E. coli* HB101 harbouring pAcUW2B and *E. coli* SURETM harbouring pAcST-3 were deposited at the National Collection of Industrial and Marine Bacteria, Aberdeen, GB on 22 Mar. 1991 under accession numbers NCIMB 40393, NCIMB 40394 and NCIMB 40395 respectively.

References

Adachi, T., Takiya, S., Suzuki, Y., Iwami, M., Kawakami, A., Takahashi, S. Y., Ishizaki, H., Nagasawa, H., Suzuki, A., (1989). CDNA structure and expression of bombyxin, an insulin-like brain secretory peptide of the silkworm *Bombyx mori*. J. Biol. Chem., 264: 7681–7685.

Blissard, G. W., Rohrmann, G. F. (1989). Location, sequence, transcription mapping, and temporal expression of the gp64 envelope glycoprotein gene of the *Orgyia pseudotsugata* multicapsid nuclear polyhedrosis virus. Virology, 170: 537–555.

Bougis, P. E., Rochat, H., Smith, L. A. (1989). Precursors of *Androctonus australis* scorpion neurotoxins. Structures of precursors, processing outcomes, and expression of a functional recombinant toxin II. J. Biol. Chem., 264: 19259–19265.

Brown, M., Faulkner, P. (1977). A plaque assay for nuclear polyhedrosis virus using a solid overlay. J. Gen. Virol., 36: 361–364.

Carbonell, L. F., Hodge, M. R., Tomalski, M. D., Miller, L. K. (1988). Synthesis of a gene coding for an insect-specific scorpion neurotoxin and attempts to express it using baculovirus vectors. Gene, 73: 409–418.

Cook, R. F., Avery, R. J., Dimmock, N. J. (1979). Infection of chicken erythrocytes with influenza and other viruses. Infection and Immunity 25: 396–402.

Cunningham, J. C. (1982). Field trials with baculoviruses: control of forest insect pests. In Microbial and Viral Insecticides, pp. 335–386. Edited by E. Kurstak. Marcel Dekker, New York.

Dente, L., Cesarini, G., and Cortese, R. (1983) Nucl. Acids Res. 11, 645–1655. pEMBL: a new family of single stranded plasmids.

Felgner, P. L., Gadek, T. R., Holm, M., Roman, R., Chan, H. W., Wenz, M., Northrop, J. P., Ringold, G. M., Danielsen, M. (1987). Lipofection: A highly efficient, lipid-mediated DNA-transfection procedure. Proc. Natl. Acad. Sci. (U.S.A.), 84: 7413–7417.

Finney, D. J. (1971). Probit Analysis, 3rd ed. Cambridge University Press, London, England.

Gordon, J. D., Carstens, E. B. (1984). Phenotypic characterization and physical mapping of a temperature-sensitive mutant of *Autographa californica* nuclear polyhedrosis virus defective in DNA synthesis. Virology, 138: 69–81.

Groebe, D. R., Chung, A. E., Ho, C. (1990). Cationic lipid-mediated co-transfection of insect cells. Nucl. Acids Res., 18 (13): 4033.

Hammock, B. D., Bonning, B. C., Possee, R. D., Hanzlik, T. N., Maeda, S. (1990). Expression and effects of the juvenile hormone esterase in a baculovirus vector. Nature, 344: 458–461.

Hanzlik, T. N., Abdel-Aal, Y. A. I., Harshman, L. G., Hammock, B. D. (1989). Isolation and sequencing of the CDNA clones coding for juvenile hormone esterase form *Heliothis viriscens*. J. Biol. Chem., 264: 12419–12425.

Harrap, K. A., Payne, C. C., Robertson, J. S. (1977). The properties of three baculoviruses from closely related hosts. Virology, 79: 14–31.

Hill-Perkins, M. S. and Possee, R. D. (1990). A baculovirus expression vector derived from the basic protein promoter of *Autographa californica* nuclear polyhedrosis virus. J. gen. Virol. 11, 971–976.

Hooft van Iddekinge, B. J. L., Smith, G. E., Summers, M. D. (1983). Nucleotide sequence of the polyhedrin gene of *Autographa californica* nuclear polyhedrosis virus. Virology, 131: 561–565.

Horodyski, F. M., Riddiford, L. M., Truman, J. W., (1989). Isolation and characterization of the eclosion hormone gene from the tobacco hornworm, *Manduca sexta*. Proc. Natl. Acad. Sci. (U.S.A.), 86: 8123–8127.

Hughes, P. R., van Beek, N. A. M., Wood, H. A. (1986). A modified droplet feeding method for rapid assay of Bacillus. thuringiensis ans baculoviruses in noctuid larvae. J. Inverteb. Pathol., 48: 187–192.

Hughes, P. R., Wood, H. A. (1981). A synchronous peroval technique for the bioassay of insect viruses. J. Inverteb. Pathol., 37: 154–159

Hunter, F. R., Crook, N. E., Entwistle, P. F. (1984). Viruses as pathogens for the control of insects. In Microbial Methods for Environmental Biotechnology, pp. 323–347. Edited by J. M. Grainger & J. M. Lynch. New York & London: Academic Press.

Ivell, R., Richter, D. (1984). Structure and comparison of the oxytocin and vasopressin genes from rat. Proc. Natl. Acad. Sci. (U.S.A.), 81: 2006–2010.

Kawakami, A., Kataoka, H., Oka, T., Mizoguchi, A., Kimura-Kawakami, M., Adachi, T., Iwami, M., Nagasawa, H., Suzuki, A.,Ishizaki, H., 1990. Molecular cloning of the *Bombix mori* prothoracicotropic hormone. Science, 247: 1333–1335.

Kitts, P. A., Ayres, D., Possee, R. D. (1990). Linearization of baculovirus DNA enhances the recovery of recombinant expression vectors. Nucl. Acids. Res., 18(19): 5667–5672

Kunkel, T. A., (1985). Rapid and efficient site specific mutagenesis without phenotype selection. Proc. Natl. Acad. Sci. (U.S.A.), 83: 488–492.

Kuzio, J., Rohel, D. Z., Curry, C. J., Krebs, A., Carstens, E. B., Faulkner, P. (1984). Nucleotide sequence of the p10 polypeptide gene of Autographa californica nuclear polyhedrosis virus. Virology, 139: 414–418.

Livingstone, C., Jones, I. (1989). Baculovirus expression vectors with single strand capability. Nucl. Acids Res., 17: 2366.

Loret, E. P., Mansuelle, P., Rochat, H., Granier, C. (1990). Neurotoxins active on insects: Amino acid sequences, chemical modifications, and secondary structure estimations by circular dichroism of toxins from the Scorpion *Androctonous australis* Hector. Biochemistry, 29: 1492–1501

Maeda, S. (1989). Increased insecticidal effect by a recombinant baculovirus carrying a sythetic diuretic hormone gene. Biochem. Biophys. Res. Commun., 165: 1177–1183.

Martnes, J. W. M., Honee, G., Zuidema, D., van Lent, J. W. M., Visser, B., Vlak, J. M. (1990). Insecticidal activity of a bacterial crystal protein expressed by a recombinant baculovirus in insect cells. App. Env. Microb., 56: 2764–2770.

Matsuura, Y., Possee, R. D., Overton, H. A., Bishop, D. H. L. (1987). Baculovirus expression vectors: the requirements for high level expression of proteins, including glycoproteins. J. Gen. Virol., 68: 1233–1250.

Merryweather, A. T. Weyer, U., Harris, M. P. G. Hirst, M., Booth, T., Possee, R. D. (1990). Construction of genetically engineered baculovirus insecticides containing the *Bacillus thuringiensis* subsp. kurstaki HD-73 delta endotoxin. J. Gen. Virol., 71: 1535–1544.

Nojiri, H., Ishida, I., Miyashita, E., Sato, M., Urano, A., Degushi, T. (1987). Cloning and sequence analysis of cDNAs for neurohypophysial hormones vasotocin and mesotocin for the hypothalamus of toad, *Bufo japonicus*. Proc. Natl. Acad. Sci. (U.S.A.), 84: 3043–3046.

Possee, R. D. (1986). Cell-surface expression of influenza virus haemagglutinin in insect cells using a baculovirus vector. Virus Research, 5: 43–59.

Sambrook, J., Fritsch, E. F., Maniatis, T. (1989) Molecular cloning: A laboratory manual. New York, Cold Spring Harbor Press.

Sanger, F., Nicklen, S., Coulson, A. R. (1977). DNA sequencing with chain-terminating inhibitors. Proc. Natl. Acad. Sci. (U.S.A.), 74: 5463–5467.

Smith, G. E., Fraser, M. J., Summers, M. D. (1983). Molecular engineering of the *Autographa californica* nuclear polyhedrosis virus genome: deletions within the polyhedrin gene. J. Virol., 46: 584–593.

Snyder, M., Hunkapiller, M., Yuen, D., Silvert, D., Fristrom, J., Davidson, N. (1982). Cuticle protein genes of Drosophila: Structure, organization and evolution of four clustered genes. Cell, 29: 1027–1040.

Taniguchi, T., Matsui, H., Fujita, T., Takaoka, C., Kashimia, N., Yoshimoto, R., Hamuro, J. (1983). Structure and expression of a cloned cDNA for human interleukin-2. Nature, 302: 305–310.

van Hofsten, P., Faye, I., Kockum, K., Lee, J. Y., Xanthopoulos, K. G., Boman, I. A., Boman, H. G., Engstrom,?., Andreu, D., Merrifield, R. B. (1985). Molecular cloning, cDNA sequencing, and chemical synthesis of cecropin B from *Hyalophora cecropia*. Proc. Natl. Acad. Sci. (U.S.A.), 82: 2240–2243.

Vaughn, J. L., Goodwin, R. H., Tompkins. G. J., McCawley, P. (1977). The establishment of two cell lines from the insect *Spodoptera frugiperda* (Lepidoptera: Noctuidae). In vitro, 13: 213–217.

Weyer, U., Knight, S., Possee, R. D. (1990). Analysis of very late gene expression by *Autographa californica* nuclear polyhedrosis virus and the further development of multiple expression vectors. J. Gen. Virol., 71: 1525–1534.

Whitford, M., Stewart, S., Kuzio, J., Faulkner, P. (1989). Identification and sequence analysis of a gene encoding gp67, an abundant envelope glycoprotein of the baculovirus *Autographa californica* Nuclear Polyhedrosis Virus. J. Virol., 63: 1393–1399.

WHO, (1973). The use of viruses for the control of insect pests and disease vectors. report of a joint FAO/WHO meeting on insect viruses. World Health Organisation Technical Replint Series No 531. Geneva.

Wigley, P. J. (1976). The epizootiology of a nuclear polyhedrosis virus disease of the winter moth *Operophtera brumata* L. at Wistman's Wood, Dartmoor. D. Phil. thesis, University of Oxford, England.

Yanisch-Perron, C., Vieira, J. and Messing, J. (1985). Improved M13 phage cloning vectors and host strains: nucleotide sequences of the M13 mp18 and pUC19 vectors. Gene 33, 103–119.

---

We claim:

1. A stable, occluded recombinant nuclear polyhedrosis virus which has a functional polyhedrin gene and which, in insect cells infected therewith, expresses a foreign protein comprising an insecticidal toxin which is secreted by the cells which normally produce the toxin; the toxin being provided with a signal peptide such that the toxin is secreted from the insect cells.

2. The recombinant virus according to claim 1, which is selected from the group consisting of *Autographa californica* MNPV, *Bombyx mori* NPV, *Heliothis zea* NPV and *Buzura suppressuria* NPV.

3. The recombinant virus according to claim 1, wherein the toxin is selected from the group consisting of scorpion toxins and spider toxins.

4. The recombinant virus according to claim 1, wherein the toxin is AaHIT.

5. The recombinant virus according to claim 1, wherein the signal peptide is selected from the group consisting of mammalian secretory signal sequences and insect secretory signal sequences.

6. The recombinant virus according to claim 1, wherein the signal peptide is a baculovirus signal sequence.

7. The recombinant virus according to claim 1, wherein the signal peptide is the gp67 signal sequence.

8. The recombinant virus according to claim 1 which is *Autographa californica* MNPV which expresses the toxin AaHIT provided with the gp67 signal sequence.

9. A insecticidal composition comprising an inert carrier or diluent and a stable, occluded recombinant nuclear polyhedrosis virus which has a functional polyhedrin gene and which, in insect cells infected therewith, expresses a foreign protein comprising an insecticidal toxin which is secreted by the cells which normally produce the toxin; the toxin being provided with a signal peptide such that the toxin is secreted from the insect cells.

10. The composition according to claim 9 wherein the recombinant virus is selected from the group consisting of *Autographa californica* MNPV, *Bombyx mori* NPV, *Heliothis zea* NPV and *Buzura suppressuria* NPV.

11. The composition according to claim 9 wherein the toxin is selected from the group consisting of scorpion toxins and spider toxins.

12. The composition according to claim 9 wherein the toxin is AaHIT.

13. The composition according to claim 9 wherein the signal peptide is selected from the group consisting of mammalian secretory signal sequences and insect secretory signal sequences.

14. The composition according to claim 9 wherein the signal peptide is a baculovirus signal sequence.

15. The composition according to claim 9 wherein the signal peptide is the gp67 signal sequence.

16. The composition according to claim 9 wherein the recombinant virus is *Autographa californica* MNPV which expresses the toxin AaHIT provided with the gp67 signal sequence.

17. A method of controlling insects at a locus, which method comprises providing at the locus an effective amount of a stable, occluded recombinant nuclear polyhedrosis virus which has a functional polyhedrin gene and which, in insect cells infected therewith, expresses a foreign protein comprising an insecticidal toxin which is secreted by the cells which normally produce the toxin; the toxin being provided with a signal peptide such that the toxin is secreted from the insect cells.

18. The method according to claim 17 wherein the recombinant virus is selected from the group consisting of *Autographa californica* MNPV, *Bombyx mori* NPV, *Heliothis zea* NPV and *Buzura suppressuria* NPV.

19. The method according to claim 17 wherein the toxin is selected from the group consisting of scorpion toxins and spider toxins.

20. The method according to claim 17 wherein the toxin is AaHIT.

21. The method according to claim 17 wherein the signal peptide is selected from the group consisting of mammalian secretory signal sequences and insect secretory signal sequences.

22. The method according to claim 17 wherein the signal peptide is a baculovirus signal sequence.

23. The method according to claim 17 wherein the signal peptide is the gp67 signal sequence.

24. The method according to claim 17 wherein the recombinant virus is *Autographa californica* MNPV which expresses the toxin AaHIT provided with the gp67 signal sequence.

* * * * *

SEQUENCE LISTING ( 1 ) GENERAL INFORMATION:

( i i i ) NUMBER OF SEQUENCES: 73

( 2 ) INFORMATION FOR SEQ ID NO: 1:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 1:

```
Met  Cys  Met  Pro  Cys  Phe  Thr  Thr  Arg  Pro  Asp  Met  Ala  Gln  Gln  Cys
1                  5                            10                           15

Arg  Ala  Cys  Cys  Lys  Gly  Arg  Gly  Lys  Cys  Phe  Gly  Pro  Gln  Cys  Leu
              20                           25                           30

Cys  Gly  Tyr  Asp
              35
```

( 2 ) INFORMATION FOR SEQ ID NO: 2:

( i ) SEQUENCE CHARACTERISTICS:
        ( A ) LENGTH: 59 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 2:

```
Ala  Asp  Gly  Tyr  Val  Lys  Gly  Cys  Lys  Ile  Ser  Cys  Phe  Leu  Asp  Asn
1                  5                            10                           15
```

Asp Leu Cys Asn Ala Asp Cys Lys Tyr Tyr Gly Gly Lys Leu Asn Ser
                      20                  25                      30

Trp Cys Ile Pro Asp Lys Ser Gly Tyr Cys Trp Cys Pro Asn Lys Gly
                  35                  40                  45

Trp Asn Ser Ile Lys Ser Glu Thr Asn Thr Cys
          50                      55

( 2 ) INFORMATION FOR SEQ ID NO: 3:

( i ) SEQUENCE CHARACTERISTICS:
         ( A ) LENGTH: 35 amino acids
         ( B ) TYPE: amino acid
         ( D ) TOPOLOGY: linear ( i i ) MOLECULE TYPE: peptide ( x i ) SEQUENCE DESCRIPTION: SEQ ID NO: 3:

Met Cys Met Pro Cys Phe Thr Thr Asp Pro Asn Met Ala Lys Lys Cys
          1               5                   10                  15

Arg Asp Cys Cys Gly Gly Asn Gly Lys Cys Phe Gly Pro Gln Cys Leu
                      20                  25                  30

Cys Asn Arg
                  35

( 2 ) INFORMATION FOR SEQ ID NO: 4:

( i ) SEQUENCE CHARACTERISTICS:
         ( A ) LENGTH: 61 amino acids
         ( B ) TYPE: amino acid
         ( D ) TOPOLOGY: linear ( i i ) MOLECULE TYPE: peptide ( x i ) SEQUENCE DESCRIPTION: SEQ ID NO: 4:

Asp Gly Tyr Ile Arg Lys Arg Asp Gly Cys Lys Leu Ser Cys Leu Phe
          1               5                   10                  15

Gly Asn Glu Gly Cys Asn Lys Glu Cys Lys Ser Tyr Gly Gly Ser Tyr
                      20                  25                  30

Gly Tyr Cys Trp Thr Trp Gly Leu Ala Cys Trp Cys Glu Gly Leu Pro
                      35                  40                  45

Asp Glu Lys Thr Trp Lys Ser Glu Thr Asn Thr Cys Gly
          50                      55                  60

( 2 ) INFORMATION FOR SEQ ID NO: 5:

( i ) SEQUENCE CHARACTERISTICS:
         ( A ) LENGTH: 62 amino acids
         ( B ) TYPE: amino acid
         ( D ) TOPOLOGY: linear ( i i ) MOLECULE TYPE: peptide ( i x ) FEATURE:
         ( A ) NAME/KEY: Modified-site
         ( B ) LOCATION: 15
         ( D ) OTHER INFORMATION: /note= "This toxin exists in two
               isoforms. Valine may replace isoleucine at
               position 15."

( x i ) SEQUENCE DESCRIPTION: SEQ ID NO: 5:

Asp Gly Tyr Ile Arg Lys Lys Asp Gly Cys Lys Val Ser Cys Ile Ile
          1               5                   10                  15

Ile Gly Asn Glu Gly Cys Arg Lys Glu Cys Val Ala His Gly Gly Ser
                      20                  25                  30

```
              Phe  Gly  Tyr  Cys  Trp  Thr  Trp  Gly  Leu  Ala  Cys  Trp  Cys  Glu  Asn  Leu
                        35                      40                     45

Pro  Asp  Ala  Val  Thr  Trp  Lys  Ser  Ser  Thr  Asn  Thr  Asn  Gly
                        50                      55                     60
```

( 2 ) INFORMATION FOR SEQ ID NO: 6:

( i ) SEQUENCE CHARACTERISTICS:
        ( A ) LENGTH: 60 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 6:

```
              Asp  Gly  Tyr  Ile  Lys  Arg  Arg  Asp  Gly  Cys  Lys  Val  Arg  Cys  Leu  Ile
              1                   5                        10                     15

Gly  Asn  Glu  Cys  Asp  Lys  Glu  Cys  Lys  Ala  Tyr  Gly  Gly  Ser  Tyr  Gly
                             20                      25                     30

Tyr  Cys  Trp  Thr  Trp  Gly  Leu  Ala  Cys  Trp  Cys  Glu  Gly  Leu  Pro  Asp
                        35                      40                     45

Asp  Lys  Thr  Trp  Lys  Ser  Glu  Thr  Asn  Thr  Cys  Gly
                        50                      55                     60
```

( 2 ) INFORMATION FOR SEQ ID NO: 7:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 7:

```
              Ala  Leu  Pro  Leu  Ser  Gly  Glu  Tyr  Glu  Pro  Cys  Val  Arg  Pro  Arg  Lys
              1                   5                        10                     15

Cys  Lys  Pro  Gly  Leu  Val  Cys  Asn  Lys  Gln  Gln  Ile  Cys  Val  Asp  Pro
                             20                      25                     30

Lys
```

( 2 ) INFORMATION FOR SEQ ID NO: 8:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 8:

```
              Asn  Asn  Asn  Arg  Cys  Leu  Cys  Tyr  Pro  Pro  Gln  Ser  Cys  Asn  Cys  Tyr
              1                   5                        10                     15

Tyr  Gly  Asp  Cys  Cys  Asp  Glu  Tyr  Ala  Ser  Arg  Cys  Arg  Gly  Tyr  Glu
                             20                      25                     30

Gly  Val  Cys  Ser
                             35
```

( 2 ) INFORMATION FOR SEQ ID NO: 9:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 9
    ( D ) OTHER INFORMATION: /note= "Lysine replaces arginine
        at position 9 in the CT-III peptide."

( i x ) FEATURE:
    ( A ) NAME/KEY: Modified-site
    ( B ) LOCATION: 14
    ( D ) OTHER INFORMATION: /note= "Phenylalanine replaces
        alanine at position 14 in the CT-III peptide."

( x i ) SEQUENCE DESCRIPTION: SEQ ID NO: 9:

```
Ser  Asp  Ser  Arg  Cys  Arg  Cys  Tyr  Pro  Met  Ser  Arg  Cys  Ser  Cys  Tyr
1                   5                        10                       15

Tyr  Gly  Ser  Cys  Cys  Tyr  Pro  Gly  Ala  Trp  Asp  Ala  Cys  Arg  Gln  Gly
               20                       25                       30

Asp  Gly  Val  Cys  Asp  Ala
               35
```

( 2 ) INFORMATION FOR SEQ ID NO: 10:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 10:

```
Arg  Gln  Asp  Met  Val  Asp  Glu  Ser  Val  Cys  Tyr  Ile  Thr  Asp  Asn  Asn
1                   5                        10                       15

Cys  Asn  Gly  Gly  Lys  Cys  Leu  Arg  Ser  Lys  Ala  Cys  His  Ala  Asp  Pro
               20                       25                       30

Trp  Glu  Leu
          35
```

( 2 ) INFORMATION FOR SEQ ID NO: 11:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 11:

```
Met  Leu  Leu  Val  Asn  Gln  Ser  His  Gln  Gly  Phe  Asn  Lys  Glu  His  Thr
1                   5                        10                       15

Ser  Lys  Met  Val  Ser  Ala  Ile  Val  Leu  Tyr  Val  Leu  Leu  Ala  Ala  Ala
               20                       25                       30

Ala  His  Ser  Ala  Phe  Ala
               35
```

( 2 ) INFORMATION FOR SEQ ID NO: 12:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 12:

```
Met  Thr  Ser  His  Val  Leu  Ala  Leu  Ala  Phe  Leu  Leu  His  Ala  Cys  Thr
1                   5                        10                       15
```

Ala Leu Ala ( 2 ) INFORMATION FOR SEQ ID NO: 13:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 13:

```
Met Ala Gly Lys Val Thr Val Ala Phe Phe Met Phe Ala Met Ile Ala
 1               5                  10                  15
Phe Leu Ala Asn Phe Gly Tyr Val Glu Cys
                20                  25
```

( 2 ) INFORMATION FOR SEQ ID NO: 14:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 14:

```
Met Lys Ile Leu Leu Ala Ile Ala Leu Met Leu Ser Thr Val Met Trp
 1               5                  10                  15
Val Ser Thr
```

( 2 ) INFORMATION FOR SEQ ID NO: 15:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 15:

```
Met Ile Thr Arg Pro Ile Ile Leu Val Ile Leu Cys Tyr Ala Ile Leu
 1               5                  10                  15
Met Ile Val Gln Ser Phe Val Pro Lys Ala Val Ala Leu
                20                  25
```

( 2 ) INFORMATION FOR SEQ ID NO: 16:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 16:

```
Met Asn Phe Ser Arg Ile Phe Phe Phe Val Phe Ala Leu Val Leu Ala
 1               5                  10                  15
Leu Ser Thr Val Ser Ala Ala Pro Glu Pro
                20                  25
```

( 2 ) INFORMATION FOR SEQ ID NO: 17:

( i ) SEQUENCE CHARACTERISTICS:
        ( A ) LENGTH: 16 amino acids
        ( B ) TYPE: amino acid (D) TOPOLOGY: linear (ii) MOLECULE TYPE: peptide (xi) SEQUENCE DESCRIPTION: SEQ ID NO: 17:

```
Met Phe Lys Phe Val Met Ile Leu Ala Val Val Gly Val Ala Thr Ala
1               5                   10                  15
```

(2) INFORMATION FOR SEQ ID NO: 18:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO: 18:

```
Met Lys Phe Leu Leu Leu Phe Leu Val Val Leu Pro Ile Met Gly Val
1               5                   10                  15
Leu Gly
```

(2) INFORMATION FOR SEQ ID NO: 19:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO: 19:

```
Met Ser Tyr Thr Ala Leu Ala Val Thr Phe Phe Gly Trp Leu Ala Leu
1               5                   10                  15
Ser Ser Ala
```

(2) INFORMATION FOR SEQ ID NO: 20:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 20:

```
Met Tyr Arg Met Gln Leu Leu Ser Cys Ile Ala Leu Ser Leu Ala Leu
1               5                   10                  15
Val Thr Asn Ser
            20
```

(2) INFORMATION FOR SEQ ID NO: 21:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO: 21:

```
Met Ala Cys Pro Ser Leu Ala Cys Cys Leu Leu Gly Leu Leu Ala Leu
1               5                   10                  15
Thr Ser Ala
```

(2) INFORMATION FOR SEQ ID NO: 22:

( i ) SEQUENCE CHARACTERISTICS:
    ( A ) LENGTH: 327 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 1..327

( x i ) SEQUENCE DESCRIPTION: SEQ ID NO: 22:

| ATG | CTA | CTA | GTA | AAT | CAG | TCA | CAC | CAA | GGC | TTC | AAT | AAG | GAA | CAC | ACA | 48 |
|---|---|---|---|---|---|---|---|---|---|---|---|---|---|---|---|---|
| Met | Leu | Leu | Val | Asn | Gln | Ser | His | Gln | Gly | Phe | Asn | Lys | Glu | His | Thr | |
| 1 | | | | 5 | | | | | 10 | | | | | 15 | | |
| AGC | AAG | ATG | GTA | AGC | GCT | ATT | GTT | TTA | TAT | GTG | CTT | TTG | GCG | GCG | GCG | 96 |
| Ser | Lys | Met | Val | Ser | Ala | Ile | Val | Leu | Tyr | Val | Leu | Leu | Ala | Ala | Ala | |
| | | | 20 | | | | | 25 | | | | | 30 | | | |
| GCG | CAT | TCT | GCC | TTT | GCG | AAA | AAA | AAC | GGC | TAC | GCG | GTT | GAC | TCG | TCG | 144 |
| Ala | His | Ser | Ala | Phe | Ala | Lys | Lys | Asn | Gly | Tyr | Ala | Val | Asp | Ser | Ser | |
| | | 35 | | | | | 40 | | | | | 45 | | | | |
| GGC | AAA | GCG | CCA | GAA | TGT | CTA | CTA | TCG | AAC | TAC | TGT | AAC | AAC | CAA | TGT | 192 |
| Gly | Lys | Ala | Pro | Glu | Cys | Leu | Leu | Ser | Asn | Tyr | Cys | Asn | Asn | Gln | Cys | |
| | 50 | | | | | 55 | | | | | 60 | | | | | |
| ACT | AAA | GTT | CAC | TAC | GCT | GAC | AAA | GGC | TAC | TGT | TGT | CTA | CTA | AGC | TGT | 240 |
| Thr | Lys | Val | His | Tyr | Ala | Asp | Lys | Gly | Tyr | Cys | Cys | Leu | Leu | Ser | Cys | |
| 65 | | | | 70 | | | | | 75 | | | | | | 80 | |
| TAC | TGT | TTT | GGC | CTA | AAC | GAC | GAC | AAA | AAA | GTT | CTA | GAA | ATT | AGC | GAC | 288 |
| Tyr | Cys | Phe | Gly | Leu | Asn | Asp | Asp | Lys | Lys | Val | Leu | Glu | Ile | Ser | Asp | |
| | | | | 85 | | | | | 90 | | | | | 95 | | |
| ACT | CGT | AAA | AGC | TAC | TGT | GAC | ACT | ACT | ATT | ATT | AAC | TAA | | | | 327 |
| Thr | Arg | Lys | Ser | Tyr | Cys | Asp | Thr | Thr | Ile | Ile | Asn | | | | | |
| | | | 100 | | | | | 105 | | | | | | | | |

( 2 ) INFORMATION FOR SEQ ID NO: 23:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 23:

| Met | Leu | Leu | Val | Asn | Gln | Ser | His | Gln | Gly | Phe | Asn | Lys | Glu | His | Thr |
|---|---|---|---|---|---|---|---|---|---|---|---|---|---|---|---|
| 1 | | | | 5 | | | | | 10 | | | | | 15 | |
| Ser | Lys | Met | Val | Ser | Ala | Ile | Val | Leu | Tyr | Val | Leu | Leu | Ala | Ala | Ala |
| | | | 20 | | | | | 25 | | | | | 30 | | |
| Ala | His | Ser | Ala | Phe | Ala | Lys | Lys | Asn | Gly | Tyr | Ala | Val | Asp | Ser | Ser |
| | | 35 | | | | | 40 | | | | | 45 | | | |
| Gly | Lys | Ala | Pro | Glu | Cys | Leu | Leu | Ser | Asn | Tyr | Cys | Asn | Asn | Gln | Cys |
| | 50 | | | | | 55 | | | | | 60 | | | | |
| Thr | Lys | Val | His | Tyr | Ala | Asp | Lys | Gly | Tyr | Cys | Cys | Leu | Leu | Ser | Cys |
| 65 | | | | 70 | | | | | 75 | | | | | | 80 |
| Tyr | Cys | Phe | Gly | Leu | Asn | Asp | Asp | Lys | Lys | Val | Leu | Glu | Ile | Ser | Asp |
| | | | | 85 | | | | | 90 | | | | | 95 | |
| Thr | Arg | Lys | Ser | Tyr | Cys | Asp | Thr | Thr | Ile | Ile | Asn | | | | |
| | | | 100 | | | | | 105 | | | | | | | |

( 2 ) INFORMATION FOR SEQ ID NO: 24:

( i ) SEQUENCE CHARACTERISTICS:

(A) LENGTH: 60 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 24:

GATCCAAATA TGAAAAAAAA CGGCTACGCG GTTGACTCGT CGGGCAAAGC GCCAGAATGT    60

(2) INFORMATION FOR SEQ ID NO: 25:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

AGACATTCTG GCGCTTTGCC CGACGAGTCA ACCGCGTAGC CGTTTTTTTT CATATTTG    58

(2) INFORMATION FOR SEQ ID NO: 26:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

CTACTATCGA ACTACTGTAA CAACCAATGT ACTAAAGTTC ACTACGCTGA CAAAGGCTAC    60

TGTTGT    66

(2) INFORMATION FOR SEQ ID NO: 27:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

CGACAACAGT AGCCTTTGTC AGCGTAGTGA ACTTTAGTAC ATTGGTTGTT ACAGTAGTTC    60

GATAGT    66

(2) INFORMATION FOR SEQ ID NO: 28:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

GATCCACGTG ACGTGTCTAC TAAGCTGTTA CTGTTTTGGC CTAAACGACG ACAAAAAAGT    60

T    61

(2) INFORMATION FOR SEQ ID NO: 29:

(i) SEQUENCE CHARACTERISTICS:
  (A) LENGTH: 61 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO: 29:

| | | | | | |
|---|---|---|---|---|---|
| CTAGAACTTT | TTTGTCGTCG | TTTAGGCCAA | AACAGTAACA | GCTTAGTAGA | CACGTCACGT | 60 |
| G | | | | | | 61 |

(2) INFORMATION FOR SEQ ID NO: 30:

(i) SEQUENCE CHARACTERISTICS:
  (A) LENGTH: 62 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO: 30:

CTAGAAATTA GCGACACTCG TAAAAGCTAC TGTGACACTA CTATTATTAA CTAAAGATCT    60
GG                                                                  62

(2) INFORMATION FOR SEQ ID NO: 31:

(i) SEQUENCE CHARACTERISTICS:
  (A) LENGTH: 60 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO: 31:

CGCCAGATCT TTAGTTAATA ATAGTAGTGT CACAGTAGCT TTTACGAGTG TCGCTAATTT    60

(2) INFORMATION FOR SEQ ID NO: 32:

(i) SEQUENCE CHARACTERISTICS:
  (A) LENGTH: 578 base pairs
  (B) TYPE: nucleic acid
  (C) STRANDEDNESS: single
  (D) TOPOLOGY: linear (ii) MOLECULE TYPE: DNA (genomic)

(ix) FEATURE:
  (A) NAME/KEY: CDS
  (B) LOCATION: 246..569

(xi) SEQUENCE DESCRIPTION: SEQ ID NO: 32:

```
TCTAGAGTCG AGCAAGAAAA TAAAACGCCA AACGCGTTGG AGTCTTGTGT GCTATTTTAC    60
AAAGATTCAG AAATACGCAT CACTTACAAC AAGGGGGACT ATGAAATTAT GCATTTGAGG   120
ATGCCGGGAC CTTTAATTCA ACCCAACACA ATATATTATA GTTAAATAAG AATTATTATC   180
AAATCATTTG TATATTAATT AAAATACTAT ACTGTAAATT ACATTTATT TACAATCACA    240
GATCT ATG CTA CTA GTA AAT CAG TCA CAC CAA GGC TTC AAT AAG GAA       287
      Met Leu Leu Val Asn Gln Ser His Gln Gly Phe Asn Lys Glu
      1               5                  10
CAC ACA AGC AAG ATG GTA AGC GCT ATT GTT TTA TAT GTG CTT TTG GCG     335
His Thr Ser Lys Met Val Ser Ala Ile Val Leu Tyr Val Leu Leu Ala
15                  20                  25                  30
GCG GCG GCG CAT TCT GCC TTT GCG AAA AAA AAC GGC TAC GCG GTT GAC     383
```

|     |     |     |     |     |     |     |     |     |     |     |     |     |     |     |     |
|-----|-----|-----|-----|-----|-----|-----|-----|-----|-----|-----|-----|-----|-----|-----|-----|
| Ala | Ala | Ala | His | Ser | Ala | Phe | Ala | Lys | Lys | Asn | Gly | Tyr | Ala | Val | Asp |
|     |     |     |     | 35  |     |     |     |     | 40  |     |     |     |     | 45  |     |

| TCG | TCG | GGC | AAA | GCG | CCA | GAA | TGT | CTA | CTA | TCG | AAC | TAC | TGT | AAC | AAC | 431 |
|-----|-----|-----|-----|-----|-----|-----|-----|-----|-----|-----|-----|-----|-----|-----|-----|-----|
| Ser | Ser | Gly | Lys | Ala | Pro | Glu | Cys | Leu | Leu | Ser | Asn | Tyr | Cys | Asn | Asn |     |
|     |     |     | 50  |     |     |     |     | 55  |     |     |     |     | 60  |     |     |     |

| CAA | TGT | ACT | AAA | GTT | CAC | TAC | GCT | GAC | AAA | GGC | TAC | TGT | TGT | CTA | CTA | 479 |
|-----|-----|-----|-----|-----|-----|-----|-----|-----|-----|-----|-----|-----|-----|-----|-----|-----|
| Gln | Cys | Thr | Lys | Val | His | Tyr | Ala | Asp | Lys | Gly | Tyr | Cys | Cys | Leu | Leu |     |
|     |     | 65  |     |     |     |     | 70  |     |     |     |     | 75  |     |     |     |     |

| AGC | TGT | TAC | TGT | TTT | GGC | CTA | AAC | GAC | GAC | AAA | AAA | GTT | CTA | GAA | ATT | 527 |
|-----|-----|-----|-----|-----|-----|-----|-----|-----|-----|-----|-----|-----|-----|-----|-----|-----|
| Ser | Cys | Tyr | Cys | Phe | Gly | Leu | Asn | Asp | Asp | Lys | Lys | Val | Leu | Glu | Ile |     |
|     | 80  |     |     |     |     | 85  |     |     |     |     | 90  |     |     |     |     |     |

| AGC | GAC | ACT | CGT | AAA | AGC | TAC | TGT | GAC | ACT | ACT | ATT | ATT | AAC |     |     | 569 |
|-----|-----|-----|-----|-----|-----|-----|-----|-----|-----|-----|-----|-----|-----|-----|-----|-----|
| Ser | Asp | Thr | Arg | Lys | Ser | Tyr | Cys | Asp | Thr | Thr | Ile | Ile | Asn |     |     |     |
| 95  |     |     |     |     | 100 |     |     |     |     | 105 |     |     |     |     |     |     |

TAAAGATCT    578

( 2 ) INFORMATION FOR SEQ ID NO: 33:

( i ) SEQUENCE CHARACTERISTICS:
  ( A ) LENGTH: 108 amino acids
  ( B ) TYPE: amino acid
  ( D ) TOPOLOGY: linear ( i i ) MOLECULE TYPE: protein ( x i ) SEQUENCE DESCRIPTION: SEQ ID NO: 33:

| Met | Leu | Leu | Val | Asn | Gln | Ser | His | Gln | Gly | Phe | Asn | Lys | Glu | His | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Lys | Met | Val | Ser | Ala | Ile | Val | Leu | Tyr | Val | Leu | Leu | Ala | Ala | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | His | Ser | Ala | Phe | Ala | Lys | Lys | Asn | Gly | Tyr | Ala | Val | Asp | Ser | Ser |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Gly | Lys | Ala | Pro | Glu | Cys | Leu | Leu | Ser | Asn | Tyr | Cys | Asn | Asn | Gln | Cys |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Thr | Lys | Val | His | Tyr | Ala | Asp | Lys | Gly | Tyr | Cys | Cys | Leu | Leu | Ser | Cys |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Tyr | Cys | Phe | Gly | Leu | Asn | Asp | Asp | Lys | Lys | Val | Leu | Glu | Ile | Ser | Asp |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Thr | Arg | Lys | Ser | Tyr | Cys | Asp | Thr | Thr | Ile | Ile | Asn |
|-----|-----|-----|-----|-----|-----|-----|-----|-----|-----|-----|-----|
|     |     |     | 100 |     |     |     |     | 105 |     |     |     |

( 2 ) INFORMATION FOR SEQ ID NO: 34:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: CDS
  ( B ) LOCATION: 1..15

( i x ) FEATURE:
  ( A ) NAME/KEY: CDS
  ( B ) LOCATION: 27..41

( x i ) SEQUENCE DESCRIPTION: SEQ ID NO: 34:

| CAT | TCT | GCC | TTT | GCG | GATCAAATAT G | AAA | AAA | AAC | GGC | TAC | 41 |
|-----|-----|-----|-----|-----|--------------|-----|-----|-----|-----|-----|----|
| His | Ser | Ala | Phe | Ala |              | Lys | Lys | Asn | Gly | Tyr |    |
| 1   |     |     |     | 5   |              | 1   |     |     |     | 5   |    |

( 2 ) INFORMATION FOR SEQ ID NO: 35:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 35:

```
His  Ser  Ala  Phe  Ala
 1                    5
```

( 2 ) INFORMATION FOR SEQ ID NO: 36:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 36:

```
Lys  Lys  Asn  Gly  Tyr
 1                    5
```

( 2 ) INFORMATION FOR SEQ ID NO: 37:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 37:

```
CATTCTGCCT  TTGCGAAAAA  AAACGGCTAC                                         30
```

( 2 ) INFORMATION FOR SEQ ID NO: 38:

( i ) SEQUENCE CHARACTERISTICS:
        ( A ) LENGTH: 232 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 38:

```
GAGCAAGAAA  ATAAAACGCC  AAACGCGTTG  GAGTCTTGTG  TGCTATTTTA  CAAAGATTCA      60
GGAAATACGC  ATCACTTACA  ACAAGGGGGA  CTATGAAATT  ATGCATTTGA  GGATGCCGGG     120
GACCTTTAAT  TCAACCCAAC  ACAATATATT  ATAGTTAAAT  AAGAATTATT  ATCAAATCAT     180
TGTATTATTA  ATTAAAATAC  TATACTGTAA  ATTACATTTT  ATTTACAATC  AC             232
```

( 2 ) INFORMATION FOR SEQ ID NO: 39:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 7..120

(x i) SEQUENCE DESCRIPTION: SEQ ID NO: 39:

| AGATCT | ATG | CTA | CTA | GTA | AAT | CAG | TCA | CAC | CAA | GGC | TTC | AAT | AAG | GAA | 48 |
|  | Met | Leu | Leu | Val | Asn | Gln | Ser | His | Gln | Gly | Phe | Asn | Lys | Glu |  |
|  | 1 |  |  |  | 5 |  |  |  |  | 10 |  |  |  |  |  |

| CAC | ACA | AGC | AAG | ATG | GTA | AGC | GCT | ATT | GTT | TTA | TAT | GTG | CTT | TTG | GCG | 96 |
| His | Thr | Ser | Lys | Met | Val | Ser | Ala | Ile | Val | Leu | Tyr | Val | Leu | Leu | Ala |  |
| 15 |  |  |  | 20 |  |  |  |  | 25 |  |  |  |  | 30 |  |  |

| GCG | GCG | GCG | CAT | TCT | GCC | TTT | GCG | 120 |
| Ala | Ala | Ala | His | Ser | Ala | Phe | Ala |  |
|  |  |  | 35 |  |  |  |  |  |

(2) INFORMATION FOR SEQ ID NO: 40:

(i) SEQUENCE CHARACTERISTICS:
  (A) LENGTH: 38 amino acids
  (B) TYPE: amino acid
  (D) TOPOLOGY: linear (ii) MOLECULE TYPE: peptide (x i) SEQUENCE DESCRIPTION: SEQ ID NO: 40:

| Met | Leu | Leu | Val | Asn | Gln | Ser | His | Gln | Gly | Phe | Asn | Lys | Glu | His | Thr |
| 1 |  |  |  | 5 |  |  |  |  | 10 |  |  |  |  | 15 |  |

| Ser | Lys | Met | Val | Ser | Ala | Ile | Val | Leu | Tyr | Val | Leu | Leu | Ala | Ala | Ala |
|  |  |  | 20 |  |  |  |  | 25 |  |  |  |  | 30 |  |  |

| Ala | His | Ser | Ala | Phe | Ala |
|  |  | 35 |  |  |  |

(2) INFORMATION FOR SEQ ID NO: 41:

(i) SEQUENCE CHARACTERISTICS:
  (A) LENGTH: 219 base pairs
  (B) TYPE: nucleic acid
  (C) STRANDEDNESS: single
  (D) TOPOLOGY: linear (ii) MOLECULE TYPE: cDNA (i x) FEATURE:
  (A) NAME/KEY: CDS
  (B) LOCATION: 1..210

(x i) SEQUENCE DESCRIPTION: SEQ ID NO: 41:

| AAA | AAA | AAC | GGC | TAC | GCG | GTT | GAC | TCG | TCG | GGC | AAA | GCG | CCA | GAA | TGT | 48 |
| Lys | Lys | Asn | Gly | Tyr | Ala | Val | Asp | Ser | Ser | Gly | Lys | Ala | Pro | Glu | Cys |  |
| 1 |  |  |  | 5 |  |  |  |  | 10 |  |  |  |  | 15 |  |  |

| CTA | CTA | TCG | AAC | TAC | TGT | AAC | AAC | CAA | TGT | ACT | AAA | GTT | CAC | TAC | GCT | 96 |
| Leu | Leu | Ser | Asn | Tyr | Cys | Asn | Asn | Gln | Cys | Thr | Lys | Val | His | Tyr | Ala |  |
|  |  |  | 20 |  |  |  |  | 25 |  |  |  |  | 30 |  |  |  |

| GAC | AAA | GGC | TAC | TGT | TGT | CTA | CTA | AGC | TGT | TAC | TGT | TTT | GGC | CTA | AAC | 144 |
| Asp | Lys | Gly | Tyr | Cys | Cys | Leu | Leu | Ser | Cys | Tyr | Cys | Phe | Gly | Leu | Asn |  |
|  |  | 35 |  |  |  |  | 40 |  |  |  |  | 45 |  |  |  |  |

| GAC | GAC | AAA | AAA | GTT | CTA | GAA | ATT | AGC | GAC | ACT | CGT | AAA | AGC | TAC | TGT | 192 |
| Asp | Asp | Lys | Lys | Val | Leu | Glu | Ile | Ser | Asp | Thr | Arg | Lys | Ser | Tyr | Cys |  |
|  | 50 |  |  |  |  | 55 |  |  |  |  | 60 |  |  |  |  |  |

| GAC | ACT | ACT | ATT | ATT | AAC | TAAAGATCT | 219 |
| Asp | Thr | Thr | Ile | Ile | Asn |  |  |
| 65 |  |  |  |  | 70 |  |  |

(2) INFORMATION FOR SEQ ID NO: 42:

(i) SEQUENCE CHARACTERISTICS:
  (A) LENGTH: 70 amino acids
  (B) TYPE: amino acid
  (D) TOPOLOGY: linear (  i i  ) MOLECULE TYPE: peptide (  x i  ) SEQUENCE DESCRIPTION: SEQ ID NO: 42:

Lys Lys Asn Gly Tyr Ala Val Asp Ser Ser Gly Lys Ala Pro Glu Cys
 1               5                  10                 15

Leu Leu Ser Asn Tyr Cys Asn Asn Gln Cys Thr Lys Val His Tyr Ala
            20                  25                  30

Asp Lys Gly Tyr Cys Cys Leu Leu Ser Cys Tyr Cys Phe Gly Leu Asn
        35                  40                  45

Asp Asp Lys Lys Val Leu Glu Ile Ser Asp Thr Arg Lys Ser Tyr Cys
    50                  55                  60

Asp Thr Thr Ile Ile Asn
65                  70

( 2 ) INFORMATION FOR SEQ ID NO: 43:

( i ) SEQUENCE CHARACTERISTICS:
                ( A ) LENGTH: 69 base pairs
                ( B ) TYPE: nucleic acid
                ( C ) STRANDEDNESS: single
                ( D ) TOPOLOGY: linear ( i i ) MOLECULE TYPE: cDNA ( i x ) FEATURE:
                ( A ) NAME/KEY: CDS
                ( B ) LOCATION: 7..69

( x i ) SEQUENCE DESCRIPTION: SEQ ID NO: 43:

GGATCC ATG TAC AGG ATG CAA CTC CTG TCT TGC ATT GCA CTA AGT CTT         4 8
       Met Tyr Arg Met Gln Leu Leu Ser Cys Ile Ala Leu Ser Leu
        1               5                   10

GCA CTT GTC ACA AAC AGT GCA                                            6 9
Ala Leu Val Thr Asn Ser Ala
 15                  20

( 2 ) INFORMATION FOR SEQ ID NO: 44:

( i ) SEQUENCE CHARACTERISTICS:
                ( A ) LENGTH: 21 amino acids
                ( B ) TYPE: amino acid
                ( D ) TOPOLOGY: linear ( i i ) MOLECULE TYPE: peptide ( x i ) SEQUENCE DESCRIPTION: SEQ ID NO: 44:

Met Tyr Arg Met Gln Leu Leu Ser Cys Ile Ala Leu Ser Leu Ala Leu
 1               5                  10                  15

Val Thr Asn Ser Ala
            20

( 2 ) INFORMATION FOR SEQ ID NO: 45:

( i ) SEQUENCE CHARACTERISTICS:
                ( A ) LENGTH: 67 base pairs
                ( B ) TYPE: nucleic acid
                ( C ) STRANDEDNESS: single
                ( D ) TOPOLOGY: linear ( i i ) MOLECULE TYPE: cDNA ( i x ) FEATURE:
                ( A ) NAME/KEY: CDS
                ( B ) LOCATION: 11..67

( x i ) SEQUENCE DESCRIPTION: SEQ ID NO: 45:

AGATCTAAAT ATG ACT TCA CAC GTA CTC GCG CTC GCC TTC CTT CTA CAC         4 9

```
                Met  Thr  Ser  His  Val  Leu  Ala  Leu  Ala  Phe  Leu  Leu  His
                 1                  5                       10
GCG  TGT  ACA  GCG  CTG  GCA                                                              67
Ala  Cys  Thr  Ala  Leu  Ala
      15
```

( 2 ) INFORMATION FOR SEQ ID NO: 46:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 46:

```
Met  Thr  Ser  His  Val  Leu  Ala  Leu  Ala  Phe  Leu  Leu  His  Ala  Cys  Thr
 1                  5                       10                       15

Ala  Leu  Ala
```

( 2 ) INFORMATION FOR SEQ ID NO: 47:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 7..60

( x i ) SEQUENCE DESCRIPTION: SEQ ID NO: 47:

```
GGATCC  ATG  AAA  TTT  CTC  CTA  TTG  TTT  CTC  GTA  GTC  CTT  CCA  ATA  ATG        48
        Met  Lys  Phe  Leu  Leu  Leu  Phe  Leu  Val  Val  Leu  Pro  Ile  Met
         1                  5                       10

GGG  GTG  CTT  GGC                                                                   60
Gly  Val  Leu  Gly
 15
```

( 2 ) INFORMATION FOR SEQ ID NO: 48:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 48:

```
Met  Lys  Phe  Leu  Leu  Leu  Phe  Leu  Val  Val  Leu  Pro  Ile  Met  Gly  Val
 1                  5                       10                       15

Leu  Gly
```

( 2 ) INFORMATION FOR SEQ ID NO: 49:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 7..54

( x i ) SEQUENCE DESCRIPTION: SEQ ID NO: 49:

```
GGATCC  ATG  TTT  AAA  TTC  GTT  ATG  ATT  CTA  GCG  GTT  GTT  GGC  GTT  GCC        48
        Met  Phe  Lys  Phe  Val  Met  Ile  Leu  Ala  Val  Val  Gly  Val  Ala
         1             5                        10

ACA  GCG                                                                             54
Thr  Ala
 15
```

( 2 ) INFORMATION FOR SEQ ID NO: 50:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 50:

```
Met  Phe  Lys  Phe  Val  Met  Ile  Leu  Ala  Val  Val  Gly  Val  Ala  Thr  Ala
 1              5                        10                       15
```

( 2 ) INFORMATION FOR SEQ ID NO: 51:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 7..63

( x i ) SEQUENCE DESCRIPTION: SEQ ID NO: 51:

```
GGATCC  ATG  GCC  TGC  CCC  AGT  CTC  GCT  TGC  TGC  CTG  CTT  GGC  CTA  CTG        48
        Met  Ala  Cys  Pro  Ser  Leu  Ala  Cys  Cys  Leu  Leu  Gly  Leu  Leu
         1             5                        10

GCT  CTG  ACC  TCC  GCC                                                              63
Ala  Leu  Thr  Ser  Ala
 15
```

( 2 ) INFORMATION FOR SEQ ID NO: 52:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 52:

```
Met  Ala  Cys  Pro  Ser  Leu  Ala  Cys  Cys  Leu  Leu  Gly  Leu  Leu  Ala  Leu
 1              5                        10                       15

Thr  Ser  Ala
```

( 2 ) INFORMATION FOR SEQ ID NO: 53:

( i ) SEQUENCE CHARACTERISTICS:
        ( A ) LENGTH: 328 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 53:

```
CCAAATTCCG  TTTTGCGACG  ATGCAGAGTT  TTTGAACAGG  CTGCTCAAAC  ACATAGATCC        60

GTACCCGCTC  AGTCGGATGT  ATTACAATGC  AGCCAATACC  ATGTTTTACA  CGACTATGGA       120

AAACTATGCC  GTGTCCAATT  GCAAGTTCAA  CATTGAGGAT  ACAATAACA   TATTTAAGGT       180

GATGGAAAAT  ATTAGGAAAC  ACAGCAACAA  AAATTCAAAC  GACCAAGACG  AGTTAAACAT       240

ATATTTGGGA  GTTCAGTCGT  CGAATGCAAA  GCGTAAAAAA  TATTAATAAG  GTAAAAATTA       300

CAGCTACATA  AATTACACAA  TTTAAACG                                             328
```

( 2 ) INFORMATION FOR SEQ ID NO: 54:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 54:

```
GATCTGATAA  GAATTATTAT  CAAATCATTT  GTATATTAAT  TAAAATACTA  TACTGTAAAT        60

TACATTTTAT  TTACAATCAC                                                        80
```

( 2 ) INFORMATION FOR SEQ ID NO: 55:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 7..120

( x i ) SEQUENCE DESCRIPTION: SEQ ID NO: 55:

```
AGATCT  ATG  CTA  CTA  GTA  AAT  CAG  TCA  CAC  CAA  GGC  TTC  AAT  AAG  GAA        48
        Met  Leu  Leu  Val  Asn  Gln  Ser  His  Gln  Gly  Phe  Asn  Lys  Glu
        1                  5                       10

CAC  ACA  AGC  AAG  ATG  GTA  AGC  GCT  ATT  GTT  TTA  TAT  GTG  CTT  TTG  GCG    96
His  Thr  Ser  Lys  Met  Val  Ser  Ala  Ile  Val  Leu  Tyr  Val  Leu  Leu  Ala
15                  20                       25                       30

GCG  GCG  GCG  CAT  TCT  GCC  TTT  GCG                                           120
Ala  Ala  Ala  His  Ser  Ala  Phe  Ala
                35
```

( 2 ) INFORMATION FOR SEQ ID NO: 56:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 56:

```
Met  Leu  Leu  Val  Asn  Gln  Ser  His  Gln  Gly  Phe  Asn  Lys  Glu  His  Thr
1                  5                       10                       15

Ser  Lys  Met  Val  Ser  Ala  Ile  Val  Leu  Tyr  Val  Leu  Leu  Ala  Ala
                20                       25                       30

Ala  His  Ser  Ala  Phe  Ala
          35
```

( 2 ) INFORMATION FOR SEQ ID NO: 57:

( i ) SEQUENCE CHARACTERISTICS:
    ( A ) LENGTH: 228 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 7..228

( x i ) SEQUENCE DESCRIPTION: SEQ ID NO: 57:

```
AGATCT ATG CTA CTA GTA AAT CAG TCA CAC CAA GGC TTC AAT AAG GAA            48
       Met Leu Leu Val Asn Gln Ser His Gln Gly Phe Asn Lys Glu
         1               5                  10

CAC ACA AGC AAG ATG GTA AGC GCT ATT GTT TTA TAT GTG CTA CTA GCG           96
His Thr Ser Lys Met Val Ser Ala Ile Val Leu Tyr Val Leu Leu Ala
 15              20                  25                  30

GCG GCG GCG CAT TCT GCC TTT GCA CGT CAA GAC ATG GTT GAC GAG AGC          144
Ala Ala Ala His Ser Ala Phe Ala Arg Gln Asp Met Val Asp Glu Ser
             35                  40                  45

GTT TGT TAC ATT ACT GAC AAC AAC TGC AAC GGC GGC AAA TGC TTG CGT          192
Val Cys Tyr Ile Thr Asp Asn Asn Cys Asn Gly Gly Lys Cys Leu Arg
             50                  55                  60

AGC AAA GCA TGC CAC GCG GAC CCA TGG GAG CTA TAG                          228
Ser Lys Ala Cys His Ala Asp Pro Trp Glu Leu
             65                  70
```

( 2 ) INFORMATION FOR SEQ ID NO: 58:

( i ) SEQUENCE CHARACTERISTICS:
    ( A ) LENGTH: 73 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 58:

```
Met Leu Leu Val Asn Gln Ser His Gln Gly Phe Asn Lys Glu His Thr
  1               5                  10                  15

Ser Lys Met Val Ser Ala Ile Val Leu Tyr Val Leu Leu Ala Ala Ala
             20                  25                  30

Ala His Ser Ala Phe Ala Arg Gln Asp Met Val Asp Glu Ser Val Cys
             35                  40                  45

Tyr Ile Thr Asp Asn Asn Cys Asn Gly Gly Lys Cys Leu Arg Ser Lys
             50                  55                  60

Ala Cys His Ala Asp Pro Trp Glu Leu
 65                  70
```

( 2 ) INFORMATION FOR SEQ ID NO: 59:

( i ) SEQUENCE CHARACTERISTICS:
    ( A ) LENGTH: 61 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 59:

```
CCGTCAAGAC ATGGTTGACG AGAGCGTTTG TTACATTACT GACAACAACT GCAACGGCGG    60

C                                                                    61
```

( 2 ) INFORMATION FOR SEQ ID NO: 60:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 60:

```
AAATGCTTGC GTAGCAAAGC ATGCCACGCG GACCCATGGG AGCTATAG                48
```

( 2 ) INFORMATION FOR SEQ ID NO: 61:

( i ) SEQUENCE CHARACTERISTICS:
    ( A ) LENGTH: 65 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 61:

```
GCCGCCGTTG CAGTTGTTGT CAGTAATGTA ACAAACGCTC TCACTAACCA TGTCTTGACG    60

GCATG                                                                65
```

( 2 ) INFORMATION FOR SEQ ID NO: 62:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 62:

```
TTTACGAACG CATCGTTTCG TACGGTGCGC CTGGGTACCC TCGATATCCT AG            52
```

( 2 ) INFORMATION FOR SEQ ID NO: 63:

( i ) SEQUENCE CHARACTERISTICS:
    ( A ) LENGTH: 467 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 246..464

( x i ) SEQUENCE DESCRIPTION: SEQ ID NO: 63:

```
TCTAGAGTCG AGCAAGAAAA TAAAACGCCA AACGCGTTGG AGTCTTGTGT GCTATTTTAC    60

AAAGATTCAG AAATACGCAT CACTTACAAC AAGGGGACT  ATGAAATTAT GCATTTGAGG   120

ATGCCGGGAC CTTTAATTCA ACCCAACACA ATATATTATA GTTAAATAAG AATTATTATC   180

AAATCATTTG TATATTAATT AAAATACTAT ACTGTAAATT ACATTTTATT TACAATCACA   240

GATCT ATG CTA CTA GTA AAT CAG TCA CAC CAA GGC TTC AAT AAG GAA       287
      Met Leu Leu Val Asn Gln Ser His Gln Gly Phe Asn Lys Glu
       1               5                  10

CAC ACA AGC AAG ATG GTA AGC GCT ATT GTT TTA TAT GTG CTA CTA GCG    335
His Thr Ser Lys Met Val Ser Ala Ile Val Leu Tyr Val Leu Leu Ala
 15              20                 25                  30
```

```
GCG GCG GCG CAT TCT GCC TTT GCA CGT CAA GAC ATG GTT GAC GAG AGC         383
Ala Ala Ala His Ser Ala Phe Ala Arg Gln Asp Met Val Asp Glu Ser
            35                  40                  45

GTT TGT TAC ATT ACT GAC AAC AAC TGC AAC GGC GGC AAA TGC TTG CGT         431
Val Cys Tyr Ile Thr Asp Asn Asn Cys Asn Gly Gly Lys Cys Leu Arg
            50                  55                  60

AGC AAA GCA TGC CAC GCG GAC CCA TGG GAG CTA TAG                         467
Ser Lys Ala Cys His Ala Asp Pro Trp Glu Leu
            65                  70
```

(2) INFORMATION FOR SEQ ID NO: 64:

(i) SEQUENCE CHARACTERISTICS:
        (A) LENGTH: 73 amino acids
        (B) TYPE: amino acid
        (D) TOPOLOGY: linear (ii) MOLECULE TYPE: protein (xi) SEQUENCE DESCRIPTION: SEQ ID NO: 64:

```
Met Leu Leu Val Asn Gln Ser His Gln Gly Phe Asn Lys Glu His Thr
 1            5                  10                  15

Ser Lys Met Val Ser Ala Ile Val Leu Tyr Val Leu Leu Ala Ala
            20                  25                  30

Ala His Ser Ala Phe Ala Arg Gln Asp Met Val Asp Glu Ser Val Cys
            35                  40                  45

Tyr Ile Thr Asp Asn Asn Cys Asn Gly Gly Lys Cys Leu Arg Ser Lys
            50                  55                  60

Ala Cys His Ala Asp Pro Trp Glu Leu
 65                  70
```

(2) INFORMATION FOR SEQ ID NO: 65:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 65:

```
GATCTATGCT ACTAGTAAAT CAGTCACACC AAGGCTTCAA TAAGGAACAC ACAAGCAAGA      60
TGGTAAGCGC TATTGTTTTA TATGTGCTAC TAGCGGCGGC GGCGCATTCT GCCTTT         116
```

(2) INFORMATION FOR SEQ ID NO: 66:

(i) SEQUENCE CHARACTERISTICS:
        (A) LENGTH: 107 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 66:

```
CGTCAAGAAT GGTTGACGAG AGCGTTTGTT ACATTACTGA CAACAACTGC AACGGCGGCA      60
AATGCTTGCG TAGCAAAGCA TGCCACGCGG ACCCATGGGA GCTATAG                   107
```

(2) INFORMATION FOR SEQ ID NO: 67:

(i) SEQUENCE CHARACTERISTICS:
        (A) LENGTH: 92 base pairs
        (B) TYPE: nucleic acid (C) STRANDEDNESS: single
(D) TOPOLOGY: linear (ii) MOLECULE TYPE: DNA (genomic)

(ix) FEATURE:
(A) NAME/KEY: CDS
(B) LOCATION: 13..66

(xi) SEQUENCE DESCRIPTION: SEQ ID NO: 67:

```
TATATAAGAT CT ATG AAA TTT CTC CTA TTG TTT CTC GTA GTC CTT CCA        48
              Met Lys Phe Leu Leu Leu Phe Leu Val Val Leu Pro
               1               5                  10

ATA ATG GGG GTG CTT GGC AAAAAAAACG GCTACGCGGT TGACTC                 92
Ile Met Gly Val Leu Gly
             15
```

(2) INFORMATION FOR SEQ ID NO: 68:

(i) SEQUENCE CHARACTERISTICS:
(A) LENGTH: 18 amino acids
(B) TYPE: amino acid
(D) TOPOLOGY: linear (ii) MOLECULE TYPE: peptide (xi) SEQUENCE DESCRIPTION: SEQ ID NO: 68:

```
Met Lys Phe Leu Leu Leu Phe Leu Val Val Leu Pro Ile Met Gly Val
 1               5                  10                  15

Leu Gly
```

(2) INFORMATION FOR SEQ ID NO: 69:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 69:

```
TATATAAGAT CTTTAGTTAA TAATAGTAGT GT                                  32
```

(2) INFORMATION FOR SEQ ID NO: 70:

(i) SEQUENCE CHARACTERISTICS:
(A) LENGTH: 95 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 13..69

(xi) SEQUENCE DESCRIPTION: SEQ ID NO:70:

```
TATATAAGAT CT ATG GCC TGC CCC AGT CTC GCT TGC TGC CTG CTT GGC        48
              Met Ala Cys Pro Ser Leu Ala Cys Cys Leu Leu Gly
               1               5                  10

CTA CTG GCT CTG ACC TCC GCC AAAAAAAACG GCTACGCGGT TGACTC             95
Leu Leu Ala Leu Thr Ser Ala
             15
```

(2) INFORMATION FOR SEQ ID NO: 71:

(i) SEQUENCE CHARACTERISTICS:

( A ) LENGTH: 19 amino acids
( B ) TYPE: amino acid
( D ) TOPOLOGY: linear ( i i ) MOLECULE TYPE: peptide ( x i ) SEQUENCE DESCRIPTION: SEQ ID NO: 71:

| Met | Ala | Cys | Pro | Ser | Leu | Ala | Cys | Cys | Leu | Leu | Gly | Leu | Leu | Ala | Leu |
|---|---|---|---|---|---|---|---|---|---|---|---|---|---|---|---|
| 1 | | | | 5 | | | | | 10 | | | | | 15 | |

| Thr | Ser | Ala |
|---|---|---|

( 2 ) INFORMATION FOR SEQ ID NO: 72:

( i ) SEQUENCE CHARACTERISTICS:
( A ) LENGTH: 86 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 13..60

( x i ) SEQUENCE DESCRIPTION: SEQ ID NO: 72:

TATATAAGAT CT ATG TTT AAA TTC GTT ATG ATT CTA GCG GTT GTT GGC           48
             Met Phe Lys Phe Val Met Ile Leu Ala Val Val Gly
              1               5                   10

GTT GCC ACA GCG AAAAAAAACG GCTACGCGGT TGACTC                            86
Val Ala Thr Ala
         15

( 2 ) INFORMATION FOR SEQ ID NO: 73:

( i ) SEQUENCE CHARACTERISTICS:
( A ) LENGTH: 16 amino acids
( B ) TYPE: amino acid
( D ) TOPOLOGY: linear ( i i ) MOLECULE TYPE: peptide ( x i ) SEQUENCE DESCRIPTION: SEQ ID NO: 73:

| Met | Phe | Lys | Phe | Val | Met | Ile | Leu | Ala | Val | Val | Gly | Val | Ala | Thr | Ala |
|---|---|---|---|---|---|---|---|---|---|---|---|---|---|---|---|
| 1 | | | | 5 | | | | | 10 | | | | | 15 | |